US006992081B2

(12) United States Patent
Hom et al.

(10) Patent No.: US 6,992,081 B2
(45) Date of Patent: Jan. 31, 2006

(54) COMPOUNDS TO TREAT ALZHEIMER'S DISEASE

(75) Inventors: Roy Hom, San Francisco, CA (US); Shumeye Mamo, Oakland, CA (US); Jay Tung, Belmont, CA (US); Andrea Gailunas, San Francisco, CA (US); Varghese John, San Francisco, CA (US); Lawrence Fang, Foster City, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 365 days.

(21) Appl. No.: 09/960,634

(22) Filed: Sep. 21, 2001

(65) Prior Publication Data

US 2003/0013881 A1 Jan. 16, 2003

Related U.S. Application Data

(63) Continuation-in-part of application No. 09/815,960, filed on Mar. 23, 2001, now Pat. No. 6,737,420, and a continuation-in-part of application No. 09/816,876, filed on Mar. 23, 2001
(60) Provisional application No. 60/191,528, filed on Mar. 23, 2000.

(51) Int. Cl.
| | |
|---|---|
| *A01N 43/46* | (2006.01) |
| *A01N 43/58* | (2006.01) |
| *A61K 31/55* | (2006.01) |
| *A61K 31/54* | (2006.01) |
| *A61K 31/535* | (2006.01) |

(52) U.S. Cl. .............. 514/217.11; 514/217.12; 514/227.5; 514/237.8; 514/239.5; 514/247; 514/248; 514/252.12; 514/255.01; 514/275; 514/310; 514/313; 514/329; 514/331; 514/352; 514/357; 514/371; 514/377; 514/419; 514/426; 514/427; 514/447; 514/456; 514/459; 514/470; 514/471; 544/58.2; 544/59; 544/168; 544/169; 544/382; 544/400

(58) Field of Classification Search ........... 544/168, 544/169, 58.2, 59, 382, 400; 514/237.8, 217.11, 514/217.12, 227.5, 239.5, 247, 248, 252.12, 514/255.01, 275, 310, 313, 329, 331, 352, 514/357, 371, 377, 419, 426, 427, 447, 456, 514/459, 470, 471; 540/575; 546/309, 159, 546/169, 146, 237, 244; 548/195, 204, 233, 548/236, 483, 495, 557, 561; 549/69, 77, 549/404, 407, 424, 427, 469, 480, 496
See application file for complete search history.

(56) References Cited

U.S. PATENT DOCUMENTS

| | | | |
|---|---|---|---|
| 4,224,179 A | 9/1980 | Schneider | ............ 252/316 |
| 4,231,877 A | 11/1980 | Yamauchi et al. | ....... 210/321 |

(Continued)

FOREIGN PATENT DOCUMENTS

| | | |
|---|---|---|
| DE | 3610593 A1 (98) | 10/1987 |
| DE | 3721 855 A1 (93) | 9/1988 |

(Continued)

OTHER PUBLICATIONS

Abbenante, et al., *Biochemical and Biophysical Research Communications*, 2000, 268,pp. 133135 Inhibitors of β–Amyloid Formation Based on the β–Secretase Cleavage Site [439].

(Continued)

*Primary Examiner*—Richard L. Raymond
*Assistant Examiner*—Zachary G. Tucker
(74) *Attorney, Agent, or Firm*—McDonnell Boehnen; Hulbert & Berghoff LLP

(57) ABSTRACT

The present invention is directed toward substituted hydroxyethylene compounds of formulas (XII) (XIII), and (XIV)

(XII)

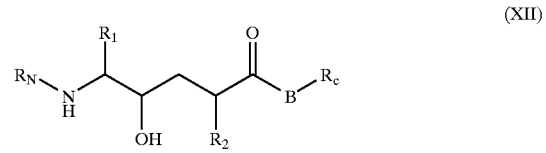

(XIII)

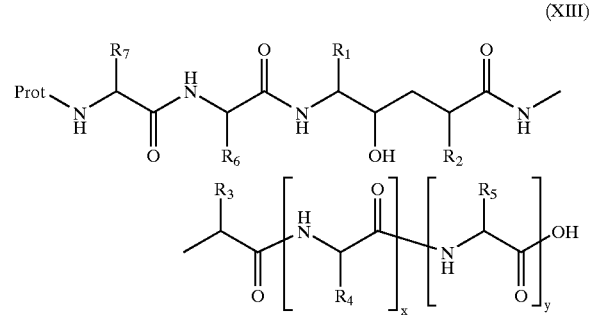

(XIV)

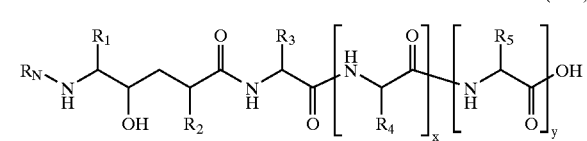

useful in treating Alzheimer's disease and other similar diseases.

8 Claims, No Drawings

U.S. PATENT DOCUMENTS

| | | | |
|---|---|---|---|
| 4,235,871 A | 11/1980 | Papahadjopoulos et al. | 424/19 |
| 4,247,411 A | 1/1981 | Vanlerberghe et al. | 252/316 |
| 4,394,448 A | 7/1983 | Szoka, Jr. et al. | 435/172 |
| 4,399,216 A | 8/1983 | Axel et al. | 435/6 |
| 4,522,811 A | 6/1985 | Eppstein et al. | 514/2 |
| 4,616,088 A | 10/1986 | Ryono et al. | 546/336 |
| 4,636,491 A | 1/1987 | Bock et al. | 514/16 |
| 4,665,193 A | 5/1987 | Ryono et al. | 548/344 |
| 4,668,770 A | 5/1987 | Boger et al. | 530/331 |
| 4,673,567 A | 6/1987 | Jizomoto | 424/38 |
| 4,676,980 A | 6/1987 | Segal et al. | 424/85 |
| 4,736,866 A | 4/1988 | Leder et al. | 800/1 |
| 4,749,792 A | 6/1988 | Natarajan et al. | 546/312 |
| 4,753,788 A | 6/1988 | Gamble | 424/1.1 |
| 4,814,270 A | 3/1989 | Piran | 435/7 |
| 4,816,567 A | 3/1989 | Cabilly et al. | 530/387 |
| 4,870,009 A | 9/1989 | Evans et al. | 435/70 |
| 4,880,781 A | 11/1989 | Hester, Jr. et al. | 514/18 |
| 4,897,355 A | 1/1990 | Eppstein et al. | 435/240.2 |
| 5,010,182 A | 4/1991 | Brake et al. | 536/227.2 |
| 5,122,523 A * | 6/1992 | Morishima et al. | 514/227.5 |
| 5,142,056 A | 8/1992 | Kempe et al. | 546/265 |
| 5,145,684 A | 9/1992 | Liversidge et al. | 424/489 |
| 5,162,538 A | 11/1992 | Voges et al. | 546/336 |
| 5,175,281 A | 12/1992 | McCall et al. | 540/94 |
| 5,250,565 A | 10/1993 | Brooks et al. | 514/443 |
| 5,364,934 A | 11/1994 | Drayna et al. | 536/23.2 |
| 5,374,652 A | 12/1994 | Buzzetti et al. | 514/418 |
| 5,376,542 A | 12/1994 | Schlegal | 435/172.2 |
| 5,387,742 A | 2/1995 | Cordell | 800/2 |
| 5,441,870 A | 8/1995 | Seubert et al. | 435/7.21 |
| 5,461,067 A | 10/1995 | Norbeck et al. | 514/333 |
| 5,475,138 A | 12/1995 | Pal et al. | 564/342 |
| 5,481,011 A | 1/1996 | Chen et al. | 549/514 |
| 5,482,947 A | 1/1996 | Talley et al. | 514/311 |
| 5,502,061 A | 3/1996 | Hui et al. | 514/311 |
| 5,502,187 A | 3/1996 | Ayer et al. | 544/117 |
| 5,508,294 A | 4/1996 | Vazquez et al. | 514/357 |
| 5,510,349 A | 4/1996 | Talley et al. | 514/237.5 |
| 5,510,388 A | 4/1996 | Vazquez et al. | 514/604 |
| 5,516,784 A | 5/1996 | Bennett et al. | 514/311 |
| 5,521,219 A | 5/1996 | Vazquez et al. | 514/604 |
| 5,545,640 A | 8/1996 | Beaulieu et al. | 514/311 |
| 5,593,846 A | 1/1997 | Schenk et al. | 435/7.9 |
| 5,602,169 A | 2/1997 | Hewawasam et al. | 514/487 |
| 5,602,175 A | 2/1997 | Talley et al. | 514/418 |
| 5,604,102 A | 2/1997 | McConlogue et al. | 435/7.1 |
| 5,610,190 A | 3/1997 | Talley et al. | 514/595 |
| 5,612,486 A | 3/1997 | McConlogue et al. | 800/2 |
| 5,625,031 A | 4/1997 | Webster et al. | 530/300 |
| 5,631,405 A | 5/1997 | Pal et al. | 564/342 |
| 5,639,769 A | 6/1997 | Vazquez et al. | 514/357 |
| 5,648,511 A | 7/1997 | Ng et al. | 558/345 |
| 5,663,200 A | 9/1997 | Bold et al. | 514/487 |
| 5,703,129 A | 12/1997 | Felsenstein et al. | 514/613 |
| 5,708,004 A | 1/1998 | Talley et al. | 514/311 |
| 5,720,936 A | 2/1998 | Wadsworth et al. | 424/9.1 |
| 5,721,130 A | 2/1998 | Seubert et al. | 435/240 |
| 5,733,882 A | 3/1998 | Carr et al. | 514/19 |
| 5,744,346 A | 4/1998 | Chrysler et al. | 435/226 |
| 5,753,652 A | 5/1998 | Fässler et al. | 514/227.5 |
| 5,760,064 A | 6/1998 | Vazquez et al. | 514/357 |
| 5,760,076 A | 6/1998 | Vazquez et al. | 514/539 |
| 5,766,846 A | 6/1998 | Schlossmacher et al. | 435/6 |
| 5,807,870 A | 9/1998 | Anderson et al. | 514/318 |
| 5,807,891 A | 9/1998 | Bold et al. | 514/487 |
| 5,811,633 A | 9/1998 | Wadsworth et al. | 800/2 |
| 5,827,891 A | 10/1998 | Dressman et al. | 514/616 |
| 5,830,897 A | 11/1998 | Vazquez et al. | 514/256 |
| 5,831,117 A | 11/1998 | Ng et al. | 562/84 |
| 5,847,169 A | 12/1998 | Nummy et al. | 549/521 |
| 5,849,911 A | 12/1998 | Fässler et al. | 544/335 |
| 5,850,003 A | 12/1998 | McLonlogue et al. | 800/2 |
| 5,863,902 A | 1/1999 | Munoz et al. | 514/19 |
| 5,872,101 A | 2/1999 | Munoz et al. | 514/18 |
| 5,877,015 A | 3/1999 | Hardy et al. | 435/325 |
| 5,877,399 A | 3/1999 | Hsiao et al. | 800/2 |
| 5,886,046 A | 3/1999 | Hirschmann et al. | 514/617 |
| 5,912,410 A | 6/1999 | Cordell | 800/2 |
| 5,922,770 A | 7/1999 | Peschke et al. | 514/619 |
| 5,935,976 A | 8/1999 | Bold et al. | 514/346 |
| 5,942,400 A | 8/1999 | Anderson et al. | 435/7.1 |
| 5,962,419 A | 10/1999 | McDonald et al. | 514/19 |
| 5,965,588 A | 10/1999 | Vazquez et al. | 514/357 |
| 6,001,813 A | 12/1999 | Gyorkos et al. | 514/18 |
| 6,013,658 A | 1/2000 | Lau et al. | 514/364 |
| 6,022,872 A | 2/2000 | Vazquez et al. | 514/231.2 |
| 6,045,829 A | 4/2000 | Liversidge et al. | 424/489 |
| 6,051,684 A | 4/2000 | McDonald et al. | 530/331 |
| 6,060,476 A | 5/2000 | Vazquez et al. | 514/256 |
| 6,150,344 A | 11/2000 | Carroll et al. | 514/119 |
| 6,153,652 A | 11/2000 | Wu et al. | 514/619 |
| 6,191,166 B1 | 2/2001 | Audia et al. | 514/534 |
| 6,221,670 B1 | 4/2001 | Cordell et al. | 436/63 |

FOREIGN PATENT DOCUMENTS

| | | |
|---|---|---|
| DE | 40 03 575 A1 | 8/1991 |
| EP | 0 036776 A2 (471) | 9/1981 |
| EP | 0 073 657 B1 (476) | 3/1983 |
| EP | 0 117 058 B1 (473) | 8/1984 |
| EP | 0 117 060 A2 (472) | 8/1984 |
| EP | 0 173 441 A1 (557) | 5/1986 |
| EP | 0 209 897 A2 (90) | 1/1987 |
| EP | 0 212 903 B1 (100) | 3/1987 |
| EP | 0 264 106 B1 (101) | 4/1988 |
| EP | 0 274 259 A2 (89) | 7/1988 |
| EP | 0 320 205 A2 (102) | 6/1989 |
| EP | 0 337 714 (8) | 10/1989 |
| EP | 0 362 179 A2 (449) | 4/1990 |
| EP | 0 372 537 A2 (96) | 6/1990 |
| EP | 0 437 729 A2 (21) | 7/1991 |
| EP | 0 609 625 A1 (567) | 8/1994 |
| EP | 0 652 009 A1 (709) | 5/1995 |
| GB | 2 203 740 A (544) | 10/1988 |
| GB | 2 211 504 A (475) | 7/1989 |
| JP | 7-126286 (97) | 5/1995 |
| WO | WO 87/02986 (551) | 5/1987 |
| WO | WO 87/04349 (10) | 7/1987 |
| WO | WO 87/05330 (454) | 9/1987 |
| WO | WO 89/00161 (15) | 1/1989 |
| WO | WO 89/01488 (12) | 2/1989 |
| WO | WO 89/05859 (453) | 6/1989 |
| WO | WO 90/13646 (452) | 11/1990 |
| WO | WO 91/00360 (451) | 1/1991 |
| WO | WO 92/00750 (537) | 1/1992 |
| WO | WO 92/17490 (14) | 10/1992 |
| WO | WO 92/20373 (455) | 11/1992 |
| WO | WO 93/02057 (11) | 2/1993 |
| WO | WO 93/08829 (450) | 5/1993 |
| WO | WO 93/17003 (7) | 9/1993 |
| WO | WO 94/04492 (848) | 3/1994 |
| WO | WO 95/06030 (839) | 3/1995 |
| WO | WO 96/35414 (999) | 11/1996 |
| WO | WO 97/30072 (22) | 8/1997 |
| WO | WO 98/22597 (170) | 5/1998 |
| WO | WO 98/29401 (562) | 7/1998 |
| WO | WO 98/33795 (546) | 8/1998 |
| WO | WO 98/38167 (987) | 9/1998 |
| WO | WO 98/50342 (550) | 11/1998 |
| WO | WO 99/41266 (568) | 8/1999 |
| WO | WO 99/54293 (635) | 10/1999 |

| WO | WO 00/17369 (169) | 3/2000 |
| --- | --- | --- |
| WO | WO 00/47618 (364) | 8/2000 |
| WO | WO 00/56335 (314) | 9/2000 |
| WO | WO 00/61748 (302) | 10/2000 |
| WO | WO 00/69262 (272) | 11/2000 |
| WO | WO 00/77030 (256) | 12/2000 |
| WO | WO 01/00663 (159) | 1/2001 |
| WO | WO 01/00665 A2 (20) | 1/2001 |
| WO | WO 01/10387 A2 (443) | 2/2001 |
| WO | WO 01/19797 A2 (381) | 3/2001 |
| WO | WO 01/23533 A2 (289) | 4/2001 |
| WO | WO 01/29563 A1 (479) | 4/2001 |
| WO | WO 01/51659 A2 (790) | 7/2001 |

OTHER PUBLICATIONS

Alterman et al., *J. Med. Chem*, 1998, 41, 3782–3792 Design and Synthesis of New Potent $C_2$–Symmetric HIV–1 Protease Inhibitors. Use of L–Mannaric Acid as a Peptidomimetic Scaffold [868].

Arnblard et al., *J. Med. Chem.*, 1999, 42:20, pp. 4193–4201 Synthesis and Characterization fo Bradykinin $B_2$ Receptor Agonists Containing Constrained Dipeptide Mimics [730 ].

Arrowsmith et al., *Tetrahedron Letters*, 1987, 28:45, pp. 5569–5572 Amino–Alcohol Dipeptide Analogues: A Synthesis of a Versatile Isostere for the Development of Proteinase Inhibitors [584].

Askin et al., *The Journal of Organic Chemistry*, 1992, 57:10, pp. 2771–2773 Highly Disastrous Alkylations of Chiral Amide Enolates: New Routes to Hydroxyethylene Dipeptide Isostere Inhibitors of HIV–1 Protease [561].

Balicki et al., *Synth. Comm.*, 1993, 23(22), pp. 3149–3155 Mild and Efficient Conversions of Nitriles to Amides with Basic Urea–Hydrogen Peroxide Adduct [874].

Barton, *Protective Groups in Organic Chemistry*, 1976, Chpt. 2, pp. 43–93 Protection of N–H Bonds and $NR_3$ [718].

Basu et al., *Tetrahedron Letters*, 1998, 39, pp. 3005–3006 Efficient Transformation of Nitrile into Amide under Mild Condition [881].

Bennett et al., *Synlett*, 1993, 9, pp. 703–704 The Synthesis of Novel HIV–Protease Inhibitors via Silica Gel Asisted Addition of Amines to Epoxides [744].

Berge et al., *Journal of Pharmaceutical Sciences*, Jan. 1977, 66:1, pp. 1–19 Pharmaceutical Salts [735].

Blatt, *Organic Syntheses*, Collective vol. 2, pp. 312–315 Heptaldoxime [883].

Bodendorf et al., *The Journal of Biological Chemistry*, 2001, 276:15, pp. 12019–12023 A Splice Variant of β–Secretase Deficient in the Amyloidogenic Processing of the Amyloid Precursor Protein [493].

Bose et al., *Synth. Comm.*, 1997, 27(18), pp. 3119–3123 A Facile Hydration of Nitriles by Dimethyldioxirane [876].

Calderwood et al., *Tetrahedron Letters*, 1997, 38:7, pp. 1241–1244 Organocerium Reactions of Benzamides and Thiobenzamides: A Direct Synthesis of Tertiary Carbinamines [741].

Chen et al., *Tetrahedron –Mannaric Acid Letters*, 1997, 38:18, pp. 3175–3178 A Practical Method for the Preparation of α'–Chloroketones of N–Carbamate Protected–α–Aminoacids [885].

Ciganek, *J. Org. Chem.*, 1992, 57:16, pp. 4521–4527 Tertiary Carbinamines by Addition of Organocerium Reagents to Nitriles and Ketimines [721].

Citron et al., *Nature*, 1992, 360:6405, pp. 672–674 Mutation of the β–amyloid Precursor Protein in Familial Alzheimer's Disease Increases β–Protein Production [722].

Cushman et al., *J. Med. Chem.*, 1997, 40:15, pp. 2323–2331 Synthesis of Analogs of 2–Methoxyestradiol with Enhanced Inhibitory Effects on Tubulin Polymerization and Cancer Cell Groth [734].

Deno, et al., *J. Am. Chem. Soc.*, 1970, 92:7, pp. 3700–3703 Protonated Cyclopropane Intermediates in the Reactions of Cyclopropanecarboxylic Acids [727].

Diedrich et al., *Tetrahedron Letters*, 1993, 34:39, pp. 6169–6172 Stereoselective Synthesis of A Hydroxyethylene Dipeptide Isostere [559].

Diercks et al., *J. Am. Chem. Soc.*, 1986, 108:11, pp. 3150–3152 Tris(benzocyclobutadieno)benzene, the Triangular [4]Phenylene with a Completely Bond–Fixed Cyclohexatriene Ring: Cobalt–Catalyzed Synthesis from Hexaethynlbenzene and Thermal Ring Opening to 1,2:5,6:9,10–Tribenzo–3,4,7,8,11,12 hexadehydro[12]–annulene [728].

Dovey et al., *Journal of Neurochemistry*, 2001, 76, pp. 173–181 Functional Gamma–Secretase Inhibitors Reduce Beta–Amyloid Peptide Levels in Brain 396.

Dragovich et al., *Journal of Medicinal Chemistry*, 1999, 42:7, pp. 1203–1212 Structure–Based Desing, Synthesis, and Biological Evaluation of Irrevirible Human Rhinovirus 3C Protease Inhibitors [553].

Emilien, et al., *Neurological Review*, 2000, 57, pp. 454–459 Prospects for Pharmacological Intervention in Alzheimer Disease [723].

Felman et al., *J. Med. Chem.* 1992, 35:7, pp. 1183–1190 Synthesis and Antiulcer Activity of Novel 5–(2–Ethenyl Substituted)–3(2H)furanones [724].

Games et al., *Letters to Nature*, Feb. 9, 1995, 373:6514, pp. 523–527 Alzheimer–type Neuropathology in Transgenic Mice Overexpressing V717Fβ–amyloid Precursor Protein [441].

Gao et al., *Tetrahedron Letters*, 1994, 50:4, pp. 979–988 Asymmetric Hetero Diels–Alder Reaction Catalyzed by Stable and Easily Prepared CAB Catalysts [882].

Getman et al., *J. Med. Chem.*, 1993, 36:2, pp. 288–291. Discovery of a Novel Class of Potent TUV T Protease Inhibitors Containing the (R)–(Hydroxyethyl)urea Isostere [732].

Ghosh et al., *J. Am. Chem. Soc.*, 2000, 122, pp. 3522–3523 Design of Potent Inhibitors of Human Brain Memapsin 2 β–Secretase). [588 ].

Ghosh et al., *J. Med. Chem.*, 1993, 36, pp. 2300–2310 Potent HIV Protease Inhibitors: The Development of Tetrahydrofuranylglycines as Novel $P_3$–Ligangs [869].

Gould, *International Journal of Pharmaceutics*, 1986, 33:1–3, pp. 201–217 Salt Selection for Basic Drugs [566].

Greene et al., *Protective Groups in Organic Synthesis: 2nd Ed.*, 1991, Chpt. 7, pp. 309–405 Protection for the Amino Group [747].

Greene, *Protective Groups in Organic Synthesis*, 1981, Chpt. 7, pp. 218–287 Protection for the Amino Group [719].

Hardy, *Nature Genetics*, 1992, 1, pp. 233–234 Framing β–Amyloid [725].

Heck, *Palladium Reagents in Organic Syntheses*, 1985, Chpt. 8.2, pp. 342–365 Carbonylatin of Aromatic Compounds to Acids, Acid Derivatives, Aldehydes and Ketones [870].

Henning, *Organic Synthesis Highlights II*, 1995, pp. 251–259 A. Synthetic Routes to Different Classes of Natural Products and Analogs Thereof—Synthesis of Hydroxyethylene Isoteric Dipeptides [565].

Hon et al., *Heterocycles,* 1990, 31:10, pp. 1745–1750 The Studies of Metal Ion Catalyzed Carbon–Hydrogen Insertion of α–Alkoxy–α'–Diazoketones Derived from Mandelic and Lactic Acids [539].

Hong et al., *Science,* 2000, 290:5489, pp. 150–153 Structure of the Protease Domain of Memapsin 2 (β–Secretase) Complexed with Inhibitor [440].

Hussain et al., *Molecular and Cellular Neuroscience,* 1999, 14, pp. 419–427 Identification of a Novel Aspartic Protease (Asp 2) as β–Secretase [726].

Kabalka et al., *Synth. Comm.,* 1990, 20(10), pp. 1445–1451 The Transformation of Nitriles into Amides [875].

Kaldor et al., *Bioorganic and Medicinal Chemistry Letters,* 1995, 5:7, pp. 721–726 Isophthalic Acid Derivatives: Amino Acid Surrogates for the Inhibition of HIV–1 Protease [587].

Kang et al., *Nature,* 1987, 327:6106, pp. 733–736 The Precursor of Alzheimer's Disease Amyloid A4 Portein Resembles a Cell–Surface Receptor [505].

Kitaguchi et al., *Nature,* Feb. 11, 1988, 331:6156, pp. 530–532 Novel Precursor of Alzheimer's Disease Amyloid Protein Shows Protease Inhibitory Activity [736].

Klumpp et al., *J. Am. Chem. Soc.,* 1979, 101:23 Lithiation of Cyclopropylcarbinols [871].

Lakouraj et al., *Indian Journal of Chemistry,* 1999, 38B, pp. 974–975 Selective Conversion of Nitriles to Amides by Amberlyst A–26 Supported Hydroperoxide [879].

Larock, *Comprehensive Organic Transformations,* 1986, Chpt 4, pp. 972–985.

Carboxylic Acids to Amildes [555].

Li et al., *Nature,* 2000, 405, pp. 689–694 Photoactivated V–secretase Inhibitors Directed to the Active Ste Covalently Label Presenilin 1 [24].

Li et al., *Nature,* 2000, 405:6787, pp. 689694 Photoactivated Gamma–Secretase Inhibitors Directed to the Active Site Covalently Label Presenilin 1. [585].

Lin et al., *PNAS,* 2000, 97:4, pp. 1456–1460 Human Aspartic Protease Memapsin 2 Cleaves the β–Amyloid Precursor Protein [687].

Luly et al., *Journal of Organic Chemistry,* 1987, 52:8, pp. 14871492 A Synthesis of Protected Aminoalkyl Epoxides from Alpha Amino Acids [558].

Luo et al., *Nature Neuroscience,* Mar. 2001, 4:3, pp. 231–232 Mice Deficient in BACE1, the Alzheimer's β–secretase, have Normal Phenotype and Abolishedβ–amyloid Generation [210].

March, *Advanced Organic Chemistry: Reactions, Mechanisms, and Structure,* 3d Ed., pp. 380–381 Aliphatic Nucleophilic Substitution [729].

Martin et al., *Tetrahedron Letters,* 1998, 39, pp. 1517–1520 Application of Almez–Mediated Amidation Reactions to Solution Phase Peptide Synthesis [540].

Mashraqui et al., *J. Am. Chem. Soc.,* 1982, 104, pp. 4461–4465 Cyclophanes. 14. Synthesis, Structure Assignment, and Conformational Properties of [2,2](2,5)Oxazolo– and Thiazolophanes [872].

McLendon et al., *The FASEB Journal,* 2000, 14:15, pp. 2383–2386 Cell–Free Assays for Gamma–Secretase Activity [359].

Miyaura et al., *Chem. Rev.,* 1995, 95, pp. 2457–2483 Palladium–Catalyzed Cross–Coupling Reactions of Organoboron Compounds [720].

Moersch et al., *Synthesis,* 1971, 12, pp. 647–649 The Synthesis of Alpha–Hydroxycarboxylic Acids by Aeration of Lithiated Carboxylic Acids in Tetrahydrofuran Solution [564].

Murahashi et al., *J. Org. Chem.,* 1992, 57:9, pp. 2521–2523 Ruthenium–Catalyzed Hydration of Nitriles and Transformation of δ–Keto Nitriles to Ene–Lactams [877].

Norman et al., *J. Med. Chem.,* 2000, 43, pp. 4288–4312 Structure–Activity Relationships of a Series of Pyrrolo[3, 2–d]pyrimidine Derivatives and Related Compounds as Neuropeptide Y5 Receptor Antagonists [867].

Owa et al., *J. Med. Chem.,* 1999, 42, pp. 3789–3799 Discovery of Novel Antitumor Sulfonamides Targeting G1 Phase of the Cell Cycle [866].

Pirttila et al., *Neuroscience Letter,* 1998, 249, pp. 21–24 Longitudinal Study of Cerebrospinal Fluid Amyloid Proteins and Apolipoprotein E in Patients with Probable Alzheimer's Disease [738].

Reetz et al., *Tetrahedron Letters,* 30:40, pp. 5425–5428 Protective Group Tuning in the Stereoselective Conversion of α–Amino Aldehydes into Aminoalkyl Epoxides [884].

Sabbagh et al., *Alzheimer's Disease Review,* 1997, 3, 1–19 β–Amyloid and Treatment Opportunities for Alzheimer's Disease [589].

Sakurai et al., *Chemical & Pharmaceutical Bulletin,* 1993, 41:8, pp. 1378–1386 Studies of HIV–1 Protease Inhibitors, II, Incorporation of Four Types of Hydroxyethylene Dipeptide Isosteres at the Scissile Site of Substrate Sequences [549].

Sakurai et al., *Tetrahedron Letters,* 1993, 34:10, pp. 5939–5942 A New Synthetic Route for the Gamma–Lactone Precursors of Hydroxyethylene Dipeptide Isosteres [563].

Sebti et al., *Tetrahedron Letters,* 1996, 37:36, pp. 6555–6556 Catalyse Heterogene de L'Hydratation des Nitriles en Amides par le Phosphate Naturel Dope par KF et le Phosphate Trisodique [878].

Selkoe, *Nature,* 1999, 399:6738, pp. A23–A31 Translating Cell Biology into Therapeutic Advances in Alzheimer's Disease [541].

Selkoe, *Neuron,* 1991, 6:4, pp. 487–498 The Molecular Pathology of Alzheimer's Disease [742].

Seubert, et al., *Nature,* Sep. 1992, 359:6393, pp. 325–327 Isolation and Quantification of Soluble Alzheimer'sβ–peptide from Biological Fluids [503].

Shearman et al., *Biochemistry,* 2000, 39, pp. 8698–9704 L685, 458, an Aspartyl Protease Transition State Mimic, is a Potent Inhibitor of Amyloidβ–Protein Precursor γ–Secretase Activity [394].

Shibata et al., *Tetrahedron Letters,* 1997, 38:4, pp. 619–620 An Expeditious Synthesis of (2R, 3S)–3–tertButoxycarbonylamino–1–isobutylamino– 4–phenyl–2–butanol, a Key Building Block of HIV Protease Inhibitors [583].

Sinha, et al., *Nature,* Dec. 2, 1999, 402:6761, pp. 537–540 Purification and Cloning of Amyloid Precursor Proteinβ–secretase from Human Brain [743].

Smith et al., *Advanced Organic Chemistry—Reactions, Mechanisms and Structure,* 2001, 5ed., Chpt. 19, pp. 1552–1554 Reduction of Carboxylic Acids and Esters to Alkanese [919].

Snyder et al., *J. Am. Chem. Soc.,* Jan.–Jun. 1938, pp. 105–111 Organoboron Coimpounds, and the Study of Reaction Mechanisms. Primary Aliphatic Boronic Acids [873].

Thurkauf et al., *J. Med. Chem.,* 1990, 33, 1452–1458 Synthesis and Anticonvulsant Activity of 1–Phenylcyclohexylamine Analogues [749].

Tucker et al., *J. Med. Chem.,* 1992, 35:14, pp. 2525–2533 A Series of Potent HIV–1 Protease Inhibitors Containing a Hydroxyethyl Secondary Amine Transition State Isostere: Synthesis, Enzyme Inhibition, and Antiviral Activity [731].

Vassar et al., *Science,* Oct. 22, 1999, 286:5440, pp. 735–741 β–Secretase Cleavage of Alzheimer's Amyloid Precurosor Protein by the Transmembrane Aspartic Protease BACE [750].

Vazquez et al., *J. of Med. Chem.,* 1995, 38:4, pp. 581–584 Inhibitors of HIV–1 Protease Containing the Novel and Potent ®–Hydroxyethyl)sulfonamide Isostere [582 ].

Wang et al., *Synlett,* Jun. 2000, 6, pp. 902–904 Preparation of α–Chloroketones by the Chloroacetate Claisen Reaction [886].

Werner et al., *Organic Syntheses,* 1973, Collective vol. 5, pp. 273–276 Cyclobutylamine* [752].

Wilgus, et al., *Tetrahedron Letters,* 1995, 36:20, pp. 3469–3472 The Acid–Catalyzed and Uncatalyzed Hydrolysis of Nitriles on Unactivated Alumina [880].

Yan et al., *Nature,* Dec. 1999, 402:6761, pp. 533–537 Membrane–anchored Aspartyl Protease with Alzheimer's Diseaseβ–secretase Activity [753].

Copy of PCT International Search Report dated Oct. 17, 2001 [986].

Shugo et al., Chemical and Pharmaceutical Bulletin, vol. 40, No. 2, 1992 XP002178294—Abstract [989].

Raddatz, J. of Med. Chem., vol. 34, No. 11, 1991, pp. 3267–3280 XP002178295—Abstract [990].

Nishi et al., Chemistry Letters, 1989, pp. 1993–1996 XP002178296—Abstract [991].

Harbeson et al., J. of Med. Chem., vol. 32, No. 6, 1989, pp. 13781392 XP002178297—Abstract [992].

Thaisrivongs et al., J. Med. Chem., vol. 31, No. 7, 1988, pp. 1369–1376 XP002178298—Abstract [993].

Nakano et al., Bulletin of the Chemical Society of Japan, vol. 63, No. 8, 1990, pp. 22242232 XP002178299—Abstract [994].

Kaltenbronn et al., J. Med. Chem., vol. 33, No. 2, 1990, pp. 838845 XP002178300—Abstract [995].

Ping et al., J. Med. Chem., vol. 39, No. 10, 1996, pp. 1991–2007 XP002178301—Abstract [996].

Plummer et al., Bioorganic & Midicinal Chemistry Letters, vol. 9, No. 6, 1999, pp. 835–840 XP002178302—Abstract [997].

* cited by examiner

COMPOUNDS TO TREAT ALZHEIMER'S DISEASE

CROSS-REFERENCE TO RELATED APPLICATIONS

This application is a continuation-in-part of U.S. patent application Ser. Nos. 09/815,960 and 09/816,876 filed Mar. 23, 2001, each of which claim priority of invention under 35 U.S.C. §119(e) from U.S. provisional application No. 60/191,528, filed Mar. 23, 2000, the disclosures of which are incorporated herein by reference. U.S. patent application Ser. No. 09/815,960 is now U.S. Pat. No. 6,737,420.

FIELD OF THE INVENTION

The present invention is directed to compounds useful in treatment of Alzheimer's disease and more specifically to compounds that are capable of inhibiting beta-secretase, an enzyme that cleaves amyloid precursor protein to produce amyloid beta peptide (A beta), a major component of the amyloid plaques found in the brains of Alzheimer's sufferers.

BACKGROUND OF THE INVENTION

Alzheimer's Disease (AD) is a degenerative brain disorder presented clinically by progressive loss of memory, cognition, reasoning, judgement, and emotional stability that gradually leads to profound mental deterioration and ultimately death. Individuals with AD exhibit characteristic beta amyloid deposits in the brain (beta amyloid plaques) and in cerebral blood vessels (beta amyloid angiopathy) as well as neurofibrillary tangles. On autopsy of AD patients, large numbers of these lesions are generally found in areas of the human brain important for memory and congnitive function. Smaller numbers are found in the brains of most aged humans not showing clinical symptoms of AD. Beta amyloid plaques and beta amyloid angiopathy also characterize the brains of individuals with Down's Syndrome (Trisomy 21) and Hereditary Cerebral Hemorrhage with Beta amyloidosis of the Dutch-Type, and other such disorders.

Beta amyloid plaques are a defining feature of AD, now believed to be a causative precursor or factor in the development of disease. Beta amyloid plaques are predominantly composed of beta amyloid beta peptide (A beta, also sometimes designated betaA4).

Several isotypes of APP are known to date, including "normal" APP-695, APP-751, and APP770, having a sequence of 695, 751, and 770 amino acids, respectively. The identification of mutations in the beta amyloid precursor protein gene that cause familial, early onset AD implicate beta amyloid metabolism in the pathology of the disease. Such reported mutations include the double Swedish mutation (SW), changing $Lys^{595}$ and $Met^{596}$ to $Asp^{595}$-$Leu^{596}$, and mutations altering $Val^{717}$ to Gly, Ile, or Phe.

A beta peptide is derived by proteolysis of the beta amyloid precursor protein (APP) and is comprised of 39–42 amino acids. Several proteases called secretases are involved in the processing of APP, Deposition of Aβ in areas of the brain responsible for cognitive activities is a major factor in the development of AD. Cleavage of APP at the N-terminus of the beta A4 peptide by beta-secretase and at the C-terminus by one or more gamma-secretases constitutes the beta amyloidogenic pathway, i.e. the pathway by which A beta is formed. Cleavage of APP by alpha-secretase and the same or a different gamma-secretase produces alpha-sAPP, a secreted form of APP that does not result in beta amyloid plaque formation. This alternate I-sAPP pathway precludes the formation of A beta peptide. It has been proposed that A beta accumulates as a result of processing of APP by beta-secretase, and that therefore inhibition of the activity of this enzyme is desireable for the treatment of AD. In vivo processing of APP at the beta-secretase site is thought to be the rate-limiting step in A beta production, and is thus a therapeutic target for the treatment of AD. See, for example, Sabbagh et. al., 1997, *Alz.Dis.Rev.* 3:1–19). A description of the proteolytic processing fragments of APP can be found, for example, in U.S. Pat. Nos. 5,441,870, 5,721,130, and 5,942,400.

Several lines of evidence indicate that progressive cerebral deposition of particular beta amyloidogenic peptides, beta-amyloid peptides, (A beta), play a seminal role in the pathogenesis of AD and can precede cognitive symptoms by years or decades. See, for example, Selkoe, 1991, *Neuron* 6:487. Recently, it has been shown that A beta is released from neuronal cells grown in culture and is present in cerebrospinal fluid (CSF) of both normal individuals and AD patients. See, for example, Seubert et al., 1992, *Nature* 359:325–327.

An aspartyl protease has been identified as the enzyme responsible for processing of APP at the beta-secretase cleavage site. The beta-secretase enzyme has been disclosed using varied nomenclature, including BACE and Asp. See, for example, Sindha et. al., 1999, *Nature* 402:537–554 (p501) and published PCT application WO00/17369 (hAsp2a and hAsp2b).

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce beta amyloid beta deposits or plaques are needed for the treatment and prevention of disease characterized by beta amyloid beta deposits or plaques, such as AD.

SUMMARY OF INVENTION

The present invention is the compounds of the formula (XII), formula (XIII), and formula (XIV) below, compositions thereof, and methods useful in the treatment of Alzheimer's disease and more specifically compounds that are capable of inhibiting beta-secretase, an enzyme that cleaves amyloid precursor protein to produce A beta peptide, a major component of the amyloid plaques found in the brains of Alzheimer's sufferers.

The present invention is compounds of formula (XII):

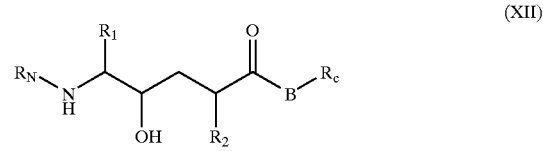

(XII)

where $R_1$ is:
(I) $C_1$–$C_6$ alkyl,
(II) $C_1$–$C_6$ alkyl-S-alkyl
(III) $C_1$–$C_6$ alkyl-($C_2$–$C_6$ alkenyl),
(IV) —$(CH_2)_{0-6}$-alkyl-$(R_{1-aryl})$ where $R_{1-aryl}$ is phenyl, 1-naphthyl, 2-naphthyl, indanyl, indenyl, dihydronaphthyl, or tetralinyl and is unsubstituted or substituted with:
(A) $C_1$–$C_6$ alkyl,
(B) —$CF_3$,
(C) —F, Cl, —Br or —I,
(D) $C_1$–$C_3$ alkoxy,
(E) —O—$CF_3$,
(F) —$NH_2$,
(G) —OH, or
(H) —CN, (V) —$(CH_2)_{0-6}$-alkyl-$(R_{1\text{-}heteroaryl})$ where $R_{1\text{-}heteroaryl}$ is:
(A) pyridinyl,
(B) pyrimidinyl,
(C) quinolinyl,
(D) indenyl,
(E) indanyl,
(F) benzothiophenyl,
(G) indolyl,
(H) indolinyl,
(I) pyridazinyl,
(J) pyrazinyl,
(K) isoindolyl,
(L) isoquinolyl,
(M) quinazolinyl,
(N) quinoxalinyl,
(O) phthalazinyl,
(P) imidazolyl,
(Q) isoxazolyl,
(R) pyrazolyl,
(S) oxazolyl,
(T) thiazolyl,
(U) indolizinyl,
(V) indazolyl,
(W) benzothiazolyl,
(X) benzimidazolyl,
(Y) benzofuranyl,
(Z) furanyl,
(AA) thienyl,
(BB) pyrrolyl,
(CC) oxadiazolyl,
(DD) thiadiazolyl,
(EE) triazolyl,
(FF) tetrazolyl,
(GG) 1,4-benzodioxan
(HH) purinyl,
(II) oxazolopyridinyl,
(JJ) imidazopyridinyl,
(KK) isothiazolyl,
(LL) naphthyridinyl,
(MM) cinnolinyl,
(NN) carbazolyl,
(OO) β-carbolinyl,
(PP) isochromanyl,
(QQ) chromanyl,
(RR) furazanyl,
(SS) tetrahydroisoquinoline,
(TT) isoindolinyl,
(UU) isobenzotetrahydrofuranyl,
(VV) isobenzotetrahydrothienyl,
(WW) isobenzothiophenyl,
(XX) benzoxazolyl, or
(YY) pyridopyridinyl,
where the $R_{1\text{-}heteroaryl}$ group is bonded to -alkyl by any ring atom of the parent $R_{1\text{-}heteroaryl}$ group substituted by hydrogen such that the new bond to the $R_{1\text{-}heteroaryl}$ group replaces the hydrogen atom and its bond, where $R_{1\text{-}heteroaryl}$ is unsubstituted or substituted with:
(1) $C_1$–$C_3$ alkyl,
(2) —$CF_3$,
(3) —F, Cl, —Br, or I,
(4) $C_1$–$C_3$ alkoxy,
(5) —O—$CF_3$,
(6) —$NH_2$,
(7) —OH, or
(8) —C≡N, (VI) —$(R_{1\text{-}heteroaryl})$ where $R_{1\text{-}heteroaryl}$ is as defined above, (VII) —$C_1$–$C_5$ alkyl-$(R_{1\text{-}heterocycle})$ where $R_{1\text{-}heterocycle}$ is:
(A) morpholinyl,
(B) thiomorpholinyl,
(C) thiomorpholinyl S-oxide,
(D) thiomorpholinyl S,S-dioxide,
(E) piperazinyl,
(F) homopiperazinyl,
(G) pyrrolidinyl,
(H) pyrrolinyl,
(I) tetrahydropyranyl,
(J) piperidinyl,
(K) tetrahydrofuranyl, or
(L) tetrahydrothiophenyl,
where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where $R_{1\text{-}heterocycle}$ is unsubstituted or substituted with:
(1) =O,
(2) $C_1$–$C_3$ alkyl,
(3) —$CF_3$,
(4) —F, Cl, —Br or —I,
(5) $C_1$–$C_3$ alkoxy,
(6) —O—$CF_3$,
(7) —$NH_2$,
(8) —OH, or
(9) —C≡N, or (VIII) —$R_{1\text{-}heterocycle}$, where $R_{1\text{-}heterocycle}$ is as defined above;
where $R_2$ is:
(I) —H,
(II) alkyl, or
(III) —$C_1$–$C_5$ alkyl-$R_{2-1}$ where $R_{2-1}$ is cycloalkyl, $R_{1\text{-}aryl}$ or $R_{1\text{-}heteroayl}$ where $R_{1\text{-}aryl}$ and $R_{1\text{-}heteroaryl}$ are as defined above;
where $R_N$ is:
(I) $R_{N-1}$—$X_N$— where $X_N$ is:
(A) —CO—,
(B) —$SO_2$—,
(C) —$(CR'R'')_{1-6}$ where R' and R'' are the same or different and are —H or $C_1$–$C_4$ alkyl,
(D) —CO—$(CR'R'')_{1-6}$—$X_{N-1}$ where $X_{N-1}$ is —O—, —S— or —NR'R''— and where R' and R'' are as defined above, or
(E) a single bond;
where $R_{N-1}$ is:
(A) $R_{N\text{-}aryl}$ where $R_{N\text{-}aryl}$ is phenyl, biphenyl, 1-naphthyl, 2-naphthyl, indanyl, indenyl, dihydronaphthyl, or tetralinyl and is unsubstituted or substituted with:
(1) $C_1$–$C_6$ alkyl,
(2) —F, —Cl, —Br, or —I,
(3) —OH,
(4) —$NO_2$,
(5) —CO—OH,
(6) —C≡N, (7) —CO—NR$_{N-2}$R$_{N-3}$ where R$_{N-2}$ and R$_{N-3}$ are the same or different and are:
  (a) —H,
  (b) —C$_1$–C$_6$ alkyl unsubstituted or substituted with
    (i) —OH, or
    (ii) —NH$_2$,
  (c) —C$_1$–C$_6$ alkyl unsubstituted or substituted with —F, —Cl, —Br, or —I,
  (d) —C$_3$–C$_7$ cycloalkyl,
  (e) —(C$_1$–C$_2$ alkyl)—(C$_3$–C$_7$ cycloalkyl).
  (f) —(C$_1$–C$_6$ alkyl)—O—(C$_1$–C$_3$ alkyl),
  (g) —C$_1$–C$_6$ alkenyl with one or two double bonds,
  (h) —C$_1$–C$_6$ alkynyl with one or two triple bonds,
  (i) —C$_1$–C$_6$ alkyl chain with one double bond and one triple bond,
  (j) —R$_{1-aryl}$ where R$_{1-aryl}$ is as defined above, or
  (k) —R$_{1-heteroaryl}$ where R$_{1-heteroaryl}$ is as defined above,
(8) —CO—(C$_3$–C$_{12}$ alkyl),
(9) —CO—(C$_3$–C$_6$ cycloalkyl),
(10) —CO—R$_{1-heteroaryl}$ where R$_{1-heteroaryl}$ is as defined above,
(11) —CO—R$_{1-heterocycle}$ where R$_{1-heterocycle}$ is as defined above,
(12) —CO—R$_{N-4}$ where R$_{N-4}$ is morpholinyl, thiomorpholinyl, piperazinyl, piperidinyl or pyrrolidinyl where each group is unsubstituted or substituted with C$_1$–C$_3$ alkyl,
(13) —CO—O—R$_{N-5}$ where R$_{N-5}$ is:
  (a) alkyl, or
  (b) —(CH$_2$)$_{0-2}$—(R$_{1-aryl}$) where R$_{1-aryl}$ is as defined above,
(14) —SO$_2$—NR$_{N-2}$R$_{N-3}$ where R$_{N-2}$ and R$_{N-3}$ are as defined above,
(15) —SO—(C$_1$–C$_8$ alkyl),
(16) —SO$_2$(C$_3$–C$_{12}$ alkyl),
(17) —NH—CO—O—R$_{N-5}$ where R$_{N-5}$ is as defined above,
(18) —NH—CO—N(C$_1$–C$_3$ alkyl)$_2$,
(19) —N—CS—N(C$_1$–C$_3$ alkyl)$_2$,
(20) —N(C$_1$–C$_3$ alkyl)—CO—R$_{N-5}$ where R$_{N-5}$ is as defined above,
(21) —NR$_{N-2}$R$_{N-3}$ where R$_{N-2}$ and R$_{N-3}$ can be the same or different and are as defined above,
(22) —R$_{N-4}$ where R$_{N-4}$ is as defined above,
(23) —O—CO—(C$_1$–C$_6$ alkyl),
(24) —O—CO—N(C$_1$–C$_3$ alkyl)$_2$,
(25) —O—CS—N(C$_1$–C$_3$ alkyl)$_2$,
(26) —O—(C$_1$–C$_6$ alkyl),
(27) —O—(C$_2$–C$_5$ alkyl)—COOH,
(28) —S—(C$_1$–C$_6$ alkyl),
(29) C$_1$–C$_6$ alkyl unsubstituted or substituted with halo,
(30) —O—(C$_1$–C$_6$ alkyl unsubstituted or substituted with halo), or
(31) —O-phenyl,
(32) (C$_1$–C$_6$ alkyl) substituted with —CO—NH—C(=O)—, (B) —R$_{N1-heteroaryl}$ where R$_{N-heteroaryl}$ is:
  (1) pyridinyl,
  (2) pyrimidinyl,
  (3) quinolinyl,
  (4) indenyl,
  (5) indanyl,
  (6) benzothiophenyl,
  (7) indolyl,
  (8) indolinyl,
  (9) pyridazinyl,
  (10) pyrazinyl,
  (11) isoindolyl,
  (12) isoquinolyl,
  (13) quinazolinyl,
  (14) quinoxalinyl,
  (15) phthalazinyl,
  (16) imidazolyl,
  (17) isoxazolyl,
  (18) pyrazolyl,
  (19) oxazolyl,
  (20) thiazolyl,
  (21) indolizinyl,
  (22) indazolyl,
  (23) benzothiazolyl,
  (24) benzimidazolyl,
  (25) benzofuranyl,
  (26) furanyl,
  (27) thienyl,
  (28) pyrrolyl,
  (29) oxadiazolyl,
  (30) thiadiazolyl,
  (31) triazolyl,
  (32) tetrazolyl,
  (33) 1,4-benzodioxan
  (34) purinyl,
  (35) oxazolopyridinyl,
  (36) imidazopyridinyl,
  (37) isothiazolyl,
  (38) naphthyridinyl,
  (39) cinnolinyl,
  (40) carbazolyl,
  (41) β-carbolinyl,
  (42) isochromanyl,
  (43) chromanyl,
  (44) furazanyl,
  (45) tetrahydroisoquinoline,
  (46) isoindolinyl,
  (47) isobenzotetrahydrofiiranyl,
  (48) isobenzotetrahydrothienyl,
  (49) isobenzothiophenyl,
  (50) benzoxazolyl, or
  (51) pyridopyridinyl,
  where the R$_{N-heteroaryl}$ group is bonded by any atom of the parent R$_{N-heteroaryl}$ group substituted by hydrogen such that the new bond to the R$_{N-heteroaryl}$ group replaces the hydrogen atom and its bond, where R$_{N-heteroaryl}$ is unsubstituted or substituted with:
  (1) C$_1$–C$_6$ alkyl,
  (2) —F, —Cl, —Br, or —I,
  (3) —OH,
  (4) —NO$_2$,
  (5) —CO—OH,
  (6) —C≡N,
  (7) —CO—NR$_{N-2}$R$_{N-3}$ where R$_{N-2}$ and R$_{N-3}$ are as defined above,
  (8) —CO—(C$_3$–C$_{12}$ alkyl),
  (9) —CO—(C$_3$–C$_6$ cycloalkyl),
  (10) —CO—R$_{1-heteroaryl}$ where R$_{1-heteroaryl}$ is as defined above,
  (11) —CO—R$_{1-heterocycle}$ where R$_{1-heterocycle}$ is as defined above,
  (12) —CO—R$_{N-4}$ where R$_{N-4}$ is as defined above,

(13) —CO—O—$R_{N-5}$ where $R_{N-5}$ is as defined above,
(14) —SO$_2$—NR$_{N-2}$R$_{N-3}$ where $R_{N-2}$ and $R_{N-3}$ are as defined above,
(15) —SO—(C$_1$–C$_8$ alkyl),
(16) —SO$_2$—(C$_3$–C$_{12}$ alkyl),
(17) —NH—CO —O—$R_{N-5}$ where $R_{N-5}$ is as defined above,
(18) —NH—CO—N(C$_1$–C$_3$ alkyl)$_2$,
(19) —N—CS—N(C$_1$–C$_3$ alkyl)$_2$,
(20) —N(C$_1$–C$_3$ alkyl)—CO—$R_{N-5}$ where $R_{N-5}$ is as defined above,
(21) —NR$_{N-2}$R$_{N-3}$ where $R_{N-2}$ and $R_{N-3}$ can be the same or different and are as defined above,
(22) —R$_{N-4}$ where $R_{N-4}$ is as defined above,
(23) —O—CO—(C$_1$–C$_6$ alkyl),
(24) —O—CO—N(C$_1$–C$_3$ alkyl)$_2$,
(25) —O—CS—N(C$_1$–C$_3$ alkyl)$_2$,
(26) —O—(C$_1$–C$_6$ alkyl),
(27) —O—(C$_2$–C$_5$ alkyl)—COOH, or
(28) —S—(C$_1$–C$_6$ alkyl),
(29) (C$_1$–C$_6$ alkyl) substituted with —CO—OH and —NH—C(=O)—,
(C) $R_{N-aryl}R_{N-aryl}$ where $R_{N-aryl}$ is as defined above,
(D) —$R_{N-aryl}$—$R_{N-heteroaryl}$ where —$R_{N-aryl}$ and —$R_{N-heteroaryl}$ are as defined above,
(E) —$R_{N-heteroaryl}$—$R_{N-aryl}$ where —$R_{N-aryl}$ and $R_{N-heteroaryl}$ are as defined above,
(F) —$R_{N-heteroaryl}$—$R_{N-heteroaryl}$ where $R_{N-heteroaryl}$ is as defined above,
(G) —$R_{N-aryl}$—O—$R_{N-aryl}$ where —$R_{N-aryl}$ is as defined above,
(H) —$R_{N-aryl}$—S—$R_{N-aryl}$ where —$R_{N-aryl}$ is as defined above,
(I) —$R_{N-heteroaryl}$—O—$R_{N-heteroaryl}$ where $R_{N-heteroaryl}$ is as defined above,
(J) —$R_{N-heteroaryl}$—S-13 $R_{N-heteroaryl}$ where $R_{N-heteroaryl}$ is as defined above
(K) —$R_{N-aryl}$—CO—$R_{N-aryl}$ where —$R_{N-aryl}$ is as defined above,
(L) —$R_{N-aryl}$—$R_{N-heteroaryl}$ where —$R_{N-aryl}$ and $R_{N-heteroaryl}$ are as defined above,
(M) —$R_{N-aryl}$—SO$_2$—$R_{N-aryl}$ where —$R_{N-aryl}$ is as defined above,
(N) —$R_{N-heteroaryl}$—CO—$R_{N-heteroaryl}$ where $R_{N-heteroaryl}$ is as defined above,
(O) —$R_{N-heteroaryl}$—SO$_2$R$_{N-heteroaryl}$ where $R_{N-heteroaryl}$ is as defined above,
(P) —$R_{N-aryl}$—O—(C$_1$–C$_8$ alkyl)-phenyl, where R$N$-aryl is as defined above,
(Q) —$R_{N-aryl}$—S—(C$_1$–C$_8$ alkyl)-phenyl, where $R_{N-aryl}$ is as defined above,
(R) —$R_{N-heteroaryl}$—O—(C$_1$–C$_8$ alkyl)-phenyl, where $R_{N-heteroaryl}$ is as defined above, or
(S) —$R_{N-heteroaryl}$—S(C$_1$–C$_8$ alkyl)-phenyl, where $R_{N-heteroaryl}$ is as defined above, or
(II) —CO—(C$_1$–C$_6$ alkyl) where alkyl is unsubstituted or substituted with:
(A) —OH,
(B) —C$_1$–C$_6$ alkoxy,
(C) —C$_1$–C$_6$ thioalkoxy,
(D) —CO—O—$R_{N-8}$ where $R_{N-8}$ is —H, C$_1$–C$_6$ alkyl or -phenyl,
(E) —CO—NR$_{N-2}$R$_{N-3}$ where $R_{N-2}$ and $R_{N-3}$ are the same or different and are as defined above,
(F) —CO—R$_{N-4}$ where $R_{N-4}$ is as defined above,
(G) —SO$_2$—(C$_1$–C$_8$ alkyl),
(H) —SO$_2$—NR$_{N-2}$R$_{N-3}$ where $R_{N-2}$ and $R_{N-3}$ are the same or different and are as defined above,
(I) —NH—CO—(C$_1$–C$_6$ alkyl),
(J) —NH—CO—O—$R_{N-8}$ where $R_{N-8}$ is as defined above,
(K) —NR$_{N-2}$R$_{N-3}$ where $R_{N-2}$ and $R_{N-3}$ are the same or different and are as defined above,
(L) —R$_{N-4}$ where $R_{N-4}$ is as defined above,
(M) —O—CO—(C$_1$–C$_6$ alkyl),
(N) —O—CO—NR$_{N-8}$R$_{N-8}$ where $R_{N-8}$ are the same or different and are as defined above, or
(O) —O—(C$_1$–C$_5$ alkyl)—COOH;
where B is —O—, —NH—, or —N(C$_1$–C$_6$ alkyl)—; and
where $R_C$ is:
(I) C$_1$–C$_8$ alkyl unsubstituted or substituted with —OH, —O-phenyl, halo, or (C$_1$–C$_6$ alkoxy unsubstituted or substituted with halo), or
(II) —C($R_{C-1}$)($R_{C-2}$)—CO—NH—$R_{C-3}$ where $R_{C-1}$ and $R_{C-2}$ are the same or different and are:
(A) —H,
(B) —C$_1$–C$_6$ alkyl,
(C) —(C$_1$–C$_4$ alkyl)—$R_{C'-aryl}$, where $R_{C'-aryl}$ is as defined for $R_{N-aryl}$,
(D) —(C$_1$–C$_4$ alkyl)—$R_{C-heteroaryl}$, where $R_{C-heteroaryl}$ is as defined for $R_{N-heteroaryl}$, and $R_{N-heteroaryl}$ is as defined above,
(E) —(C$_1$–C$_4$ alkyl)—$R_{C-heterocycle}$, where $R_{C-heterocycle}$ is as defined for $R_{N-heterocycle}$, and $R_{N-heterocycle}$ is as defined above,
(F) —$R_{C-heteroaryl}$, where $R_{C-heteroaryl}$ is as defined above,
(G) —$R_{C-heterocycle}$, where $R_{C-heterocycle}$ is as defined above,
(H) —(CH$_2$)$_{1-4}$—OH,
(I) —(CH$_2$)$_{1-4}$—R$_{C-4}$—(CH$_2$)$_{1-4}$-R$_{C'-aryl}$, where $R_{C-4}$ is —O—, —S—, —NH—, or —NR$_{C-5}$— where $R_{C-5}$ is C$_1$–C$_6$ alkyl, and where $R_{C'-aryl}$ is as defined above,
(J) —(CH$_2$)$_{1-4}$—R$_{C-4}$—(CH$_2$)$_{1-4}$—R$_{C-heteroaryl}$, where $R_{C-4}$ and $R_{C-heteroaryl}$ are as defined above, or
(K) —$R_{C'-aryl}$, where $R_{C'-aryl}$ is as defined above,
and where $R_{C-3}$ is:
(A) —H,
(B) —C$_1$–C$_6$ alkyl, substituted or unsubstituted with:
(1) —H,
(2) —C$_1$–C$_6$ alkyl,
(3) —(C$_1$–C$_4$ alkyl)—$R_{C'-aryl}$ where $R_{C'-aryl}$ is as defined for $R_{N-aryl}$,
(4) —(C$_1$–C$_4$ alkyl)—$R_{C-heteroaryl}$ where $R_{C-heteroaryl}$ is as defined for $R_{N-heteroaryl}$, and $R_{N-heteroaryl}$ is as defined above,
(5) —(C$_1$–C$_4$ alkyl)-$R_{C-heterocycle}$ where $R_{C-heterocycle}$ is as defined for $R_{N-heterocycle}$, and $R_{N-heterocycle}$ is as defined above,
(6) —$R_{C-heteroaryl}$ where $R_{C-heteroary}$ is as defined above,
(7) —$R_{C-heterocycle}$ where $R_{C-heterocycle}$ is as defined above,
(8) —(CH$_2$)$_{1-4}$—OH,
(9) —(CH$_2$)$_{1-4}$—R$_{C-4}$—(CH$_2$)$_{1-4}$—R$_{C'-aryl}$ where $R_{C-4}$ is —O—, —S—, —NH—, or —NRC$_5$— where $R_{C-5}$ is C$_1$–C$_6$ alkyl, and where $R_{C'-aryl}$ is as defined above,
(10) —(CH$_2$)$_{1-4}$—R$_{C-4}$—(CH$_2$)$_{1-4}$-R$_{C-heteroaryl}$ where $R_{C-4}$ and $R_{C-heteroaryl}$ are as defined above, or

(11) —R$_{C'\text{-}aryl}$ where R$_{C'\text{-}aryl}$ is as defined above,
(12) —CO—OH and —NH—C (=O)—,
(C) —R$_{C\text{-}aryl}$ where R$_{C'\text{-}aryl}$ is as defined above,
(D) —R$_{C\text{-}heteroaryl}$ where R$_{C\text{-}heteroaryl}$ is as defined above,
(E) —R$_{C\text{-}heterocycle}$ where R$_{C\text{-}heterocycle}$ is as defined above,
(F) —(C$_1$–C$_4$ alkyl)—R$_{C'\text{-}aryl}$ where R$_{C'\text{-}aryl}$ is as defined above,
(G) —(C$_1$–C$_4$ alkyl)—R$_{C\text{-}heteroaryl}$ where R$_{C\text{-}heteroaryl}$ is as defined above,
(H) —(C$_1$–C$_4$ alkyl)—R$_{C\text{-}heterocycle}$ where R$_{C\text{-}heterocycle}$ is as defined above, or
(J) —C(R$_{C\text{-}5}$)(R$_{C\text{-}6}$)—CO—NH—C(R$_{C\text{-}7}$)(R$_{C\text{-}8}$)—COOH, where R$_{C\text{-}5}$, R$_{C\text{-}6}$ R$_{C\text{-}7}$, and R$_{C\text{-}8}$ are the same or different, and are as defined for R$_{C\text{-}1}$ and R$_{C\text{-}2}$ and where R$_{C\text{-}1}$ and R$_{C\text{-}2}$ are as defined above;

or pharmaceutically acceptable salts thereof.

The present invention also includes compounds of the formula (XIII)

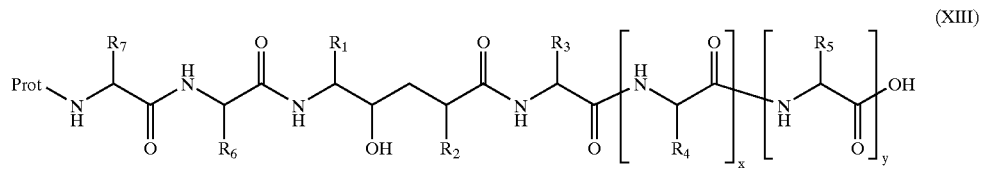

(XIII)

wherein R$_1$ is:
(I) C$_1$–C$_6$ alkyl,
(II) C$_1$–C$_6$ alkyl-S-alkyl
(III) C$_1$–C$_6$ alkyl-(C$_2$–C$_6$ alkenyl),
(IV) —(CH$_2$)$_{0\text{-}6}$-alkyl-(R$_{1\text{-}aryl}$) where R$_{1\text{-}aryl}$ is phenyl, 1-naphthyl, 2-naphthyl, indanyl, indenyl, dihydronaphthyl, or tetralinyl and is unsubstituted or substituted with:
(A) C$_1$–C$_6$ alkyl,
(B) —CF$_3$,
(C) —F, Cl, —Br or —I,
(D) C$_1$–C$_3$ alkoxy,
(E) —O—CF$_3$,
(F) —NH$_2$,
(G) —OH, or
(H) —C≡N,
(V) —(CH$_2$)$_{0\text{-}6}$-alkyl -(R$_{1\text{-}heteroaryl}$) where R$_{1\text{-}heteroaryl}$ is:
(A) pyridinyl,
(B) pyrimidinyl,
(C) quinolinyl,
(D) indenyl,
(E) indanyl,
(F) benzothiophenyl,
(G) indolyl,
(H) indolinyl,
(I) pyridazinyl,
(J) pyrazinyl,
(K) isoindolyl,
(L) isoquinolyl,
(M) quinazolinyl,
(N) quinoxalinyl,
(O) phthalazinyl,
(P) imidazolyl,
(Q) isoxazolyl,
(R) pyrazolyl,
(S) oxazolyl,
(T) thiazolyl,
(U) indolizinyl,
(V) indazolyl,
(W) benzothiazolyl,
(X) benzimidazolyl,
(Y) benzofuranyl,
(Z) furanyl,
(AA) thienyl,
(BB) pyrrolyl,
(CC) oxadiazolyl,
(DD) thiadiazolyl,
(EE) triazolyl,
(FF) tetrazolyl,
(GG) 1,4-benzodioxan
(HH) purinyl,
(II) oxazolopyridinyl,
(JJ) imidazopyridinyl,
(KK) isothiazolyl,
(LL) naphthyridinyl,
(MM) cinnolinyl,
(NN) carbazolyl,
(OO) β-carbolinyl,
(PP) isochromanyl,
(QQ) chromanyl,
(RR) furazanyl,
(SS) tetrahydroisoquinoline,
(TT) isoindolinyl,
(UU) isobenzotetrahydrofuranyl,
(VV) isobenzotetrahydrothienyl,
(WW) isobenzothiophenyl,
(XX) benzoxazolyl, or
(YY) pyridopyridinyl,
where the R$_{1\text{-}heteroaryl}$ group is bonded to -alkyl- by any ring atom of the parent R$_{1\text{-}heteroaryl}$ group substituted by hydrogen such that the new bond to the R$_{1\text{-}heteroaryl}$ group replaces the hydrogen atom and its bond, where R$_{1\text{-}heteroaryl}$ is unsubstituted or substituted with:
(1) C$_1$–C$_3$ alkyl,
(2) —CF$_3$,
(3) —F, Cl, —Br, or I,
(4) C$_1$–C$_3$ alkoxy,
(5) —O—CF$_3$,
(6) —NH$_2$,
(7) —OH, or
(8) —C≡N,
(VI) —(R$_{1\text{-}heteroaryl}$) where R$_{1\text{-}heteroaryl}$ is as defined above,
(VII) —C$_1$–C$_5$ alkyl-(R$_{1\text{-}heterocycle}$) where R$_{1\text{-}heterocycle}$ is:
(A) morpholinyl,
(B) thiomorpholinyl,
(C) thiomorpholinyl S-oxide,
(D) thiomorpholinyl S,S-dioxide,
(E) piperazinyl,
(F) homopiperazinyl,
(G) pyrrolidinyl, (H) pyrrolinyl,
(I) tetrahydropyranyl,
(J) piperidinyl,
(K) tetrahydrofuranyl, or
(L) tetrahydrothiophenyl,
where the $R_{1-heterocycle}$ group is bonded by any atom of the parent $R_{1-heterocycle}$ group substituted by hydrogen such that the new bond to the $R_{1-heterocycle}$ group replaces the hydrogen atom and its bond, where $R_{1-heterocycle}$ is unsubstituted or substituted with:
(1) =O,
(2) $C_1$–$C_3$ alkyl,
(3) —$CF_3$,
(4) —F, Cl, —Br or —I,
(5) $C_1$–$C_3$ alkoxy,
(6) —O—$CF_3$,
(7) —$NH_2$,
(8) —OH, or
(9) —CN, or
(VIII) —$R_{1-heterocycle}$, where $R_{1-heterocycle}$ is as defined above;
where $R_2$ is:
(I) —H,
(II) $C_1$–$C_6$ alkyl, or
(III) —$(CH_2)_{0-4}$—$R_{2-1}$ where $R_{2-1}$ is $(C_3$–$C_6)$cycloalkyl, $R_{1-aryl}$ or $R_{1-heteroaryl}$ where $R_{1-aryl}$ and $R_{1-heteroaryl}$ are as defined above;
where $R_3$, $R_4$, $R_5$, $R_6$, and $R_7$, are each independently —H, —$CH_3$, —$CH(CH_3)_2$, —$CH_2CH(CH_3)_2$, —CH(CH)$CH_2CH_3$, —$CH_2CH_2$*$CH_2$, wherein the *$CH_2$ is bonded to the adjacent NH to form a five membered heterocycle, —$CH_2$-phenyl, —$CH_2$(phenol), —$CH_2$—(3-indole), —$CH_2SH$, —$CH_2CH_2SCH_3$, —$CH_2OH$, —CH(OH)$CH_3$, —CH2CH2CH2CH2NH3$^+$, —$CH_2CH_2CH_2(NH)C(=NH_2^+)NH_2$, —$CH_2$—(5-(3H-imidazol-1-ium)), —$CH_2COO^-$, —$CH_2CH_2COO^-$, $CH_2CONH_2$, or —$CH_2CH_2CONH_2$;
where x is 1 or 0;
where y is 1 or 0; and
where Prot is t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-Chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl and 1-piperidyloxycarbonyl, 9-fluorenylmethyl carbonate, —CH—CH=$CH_2$, or phenyl —C(=N—)—H, or pharmaceutically acceptable salts thereof.

Also included in the present invention are compounds of formula (XIV)

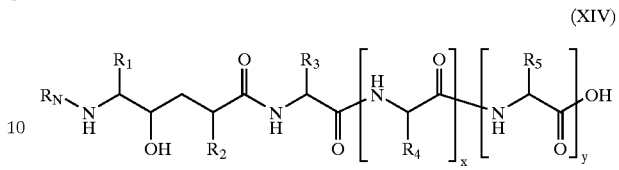

(XIV)

wherein $R_N$ is:
(I) $R_{N-1}$—$X_N$— where $X_N$ is:
(A) —CO—,
(C) —$(CR'R'')_{1-6}$ where R' and R'' are the same or different and are —H or $C_1$–$C_4$ alkyl,
(D) —CO—$(CR'R'')_{1-6}$—$X_{N-1}$ where $X_{N-1}$ is —O—, —S— or —NR'R'' and where R' and R'' are as defined above,
where $R_{N-1}$ is:
(A) $R_{N-aryl}$ where $R_{N-aryl}$ is phenyl, biphenyl, 1-naphthyl, 2-naphthyl, indanyl, indenyl, dihydronaphthyl, or tetralinyl and is unsubstituted or substituted with:
(1) $C_1$–$C_6$ alkyl,
(2) —F, —Cl, —Br, or —I,
(3) —OH,
(4) —$NO_2$,
(5) —CO—OH,
(6) —C≡N,
(7) —CO—$NR_{N-2}R_{N-3}$ where $R_{N-2}$ and $R_{N-3}$ are the same or different and are:
(a) —H,
(b) —$C_1$–$C_6$ alkyl unsubstituted or substituted with
(i) —OH, or
(ii) —$NH_2$,
(c) —$C_1$–$C_6$ alkyl unsubstituted or substituted with —F, —Cl, —Br, or —I,
(d) —$C_3$–$C_7$ cycloalkyl,
(e) —($C_1$–$C_2$ alkyl)—($C_3$–$C_7$ cycloalkyl),
(f) —($C_1$–$C_6$ alkyl)—O—($C_1$–$C_3$ alkyl),
(g) —$C_1$–$C_6$ alkenyl with one or two double bonds,
(h) —$C_1$–$C_6$ alkynyl with one or two triple bonds,
(i) —$C_1$–$C_6$ alkyl chain with one double bond and one triple bond,
(j) —$R_{1-aryl}$ where $R_{1-aryl}$ is as defined above, or
(k) —$R_{1-heteroaryl}$ where $R_{1-heteroaryl}$ is as defined above,
(8) —CO—($C_3$–$C_{12}$ alkyl),
(9) —CO—($C_3$–$C_6$ cycloalkyl),
(10) —CO—$R_{1-heteroaryl}$ where $R_{1-heteroaryl}$ is as defined above,
(11) —CO—$R_{1-heterocycle}$ where $R_{1-heterocycle}$ is as defined above,
(12) —CO—$R_{N-4}$ where $R_{N-4}$ is morpholinyl, thiomorpholinyl, piperazinyl, piperidinyl or pyrrolidinyl where each group is unsubstituted or substituted with $C_1$–$C_3$ alkyl,
(13) —CO—O—$R_{N-5}$ where $R_{N-5}$ is:
(a) alkyl, or
(b) —$(CH_2)_{0-2}$—$(R_{1-aryl})$ where $R_{1-aryl}$ is as defined above,
(14) —$SO_2$-$NR_{N-2}R_{N-3}$ where $R_{N-2}$ and $R_{N-3}$ are as defined above,

(15) —SO—($C_1$–$C_8$ alkyl),
(16) —$SO_2$($C_3$–$C_{12}$ alkyl),
(17) —NH—CO—O—$R_{N-5}$ where $R_{N-5}$ is as defined above,
(18) —NH—CO—N($C_1$–$C_3$ alkyl)$_2$,
(19) —N—CS—N($C_1$–$C_3$ alkyl)$_2$,
(20) —N($C_1$–$C_3$ alkyl)—CO—$R_{N-5}$ where $R_{N-5}$ is as defined above,
(21) —$NR_{N-2}R_{N-3}$ where $R_{N-2}$ and $R_{N-3}$ can be the same or different and are as defined above,
(22) —$R_{N-4}$ where $R_{N-4}$ is as defined above,
(23) —O—CO—($C_1$–$C_6$ alkyl),
(24) —O—CO—N($C_1$–$C_3$ alkyl)$_2$,
(25) —O—CS—N($C_1$–$C_3$ alkyl)$_2$,
(26) —O—($C_1$–$C_6$ alkyl),
(27) —O—($C_2$–$C_5$ alkyl)—COOH,
(28) —S—($C_1$–$C_6$ alkyl),
(29) $C_1$–$C_6$ alkyl unsubstituted or substituted with halo,
(30) —O—($C_1$–$C_6$ alkyl unsubstituted or substituted with halo), or
(31) —O-phenyl,
(32) ($C_1$–$C_6$ alkyl) substituted with —CO—NH—C(=O)—, (B) —$R_{N\text{-}heteroaryl}$ where $R_{N\text{-}heteroaryl}$ is:
(1) pyridinyl,
(2) pyrimidinyl,
(3) quinolinyl,
(4) indenyl,
(5) indanyl,
(6) benzothiophenyl,
(7) indolyl,
(8) indolinyl,
(9) pyridazinyl,
(10) pyrazinyl,
(11) isoindolyl,
(12) isoquinolyl,
(13) quinazolinyl,
(14) quinoxalinyl,
(15) phthalazinyl,
(16) imidazolyl,
(17) isoxazolyl,
(18) pyrazolyl,
(19) oxazolyl,
(20) thiazolyl,
(21) indolizinyl,
(22) indazolyl,
(23) benzothiazolyl,
(24) benzimidazolyl,
(25) benzofuranyl,
(26) furanyl,
(27) thienyl,
(28) pyrrolyl,
(29) oxadiazolyl,
(30) thiadiazolyl,
(31) triazolyl,
(32) tetrazolyl,
(33) 1,4-benzodioxan,
(34) purinyl,
(35) oxazolopyridinyl,
(36) imidazopyridinyl,
(37) isothiazolyl,
(38) naphthyridinyl,
(39) cinnolinyl,
(40) carbazolyl,
(41) β-carbolinyl,
(42) isochromanyl,
(43) chromanyl,
(44) furazanyl,
(45) tetrahydroisoquinoline,
(46) isoindolinyl,
(47) isobenzotetrahydrofuranyl,
(48) isobenzotetrahydrothienyl,
(49) isobenzothiophenyl,
(50) benzoxazolyl, or
(51) pyridopyridinyl,
where the $R_{N\text{-}heteroaryl}$ group is bonded by any atom of the parent $R_{N\text{-}heteroaryl}$ group substituted by hydrogen such that the new bond to the $R_{N\text{-}heteroaryl}$ group replaces the hydrogen atom and its bond, where $R_{N\text{-}heteroaryl}$ is unsubstituted or substituted with:
(1) $C_1$–$C_6$ alkyl,
(2) —F, —Cl, —Br, or —I,
(3) —OH,
(4) —$NO_2$,
(5) —CO—OH,
(6) —C≡N,
(7) —CO—$NR_{N-2}R_{N-3}$ where $R_{N-2}$ and $R_{N-3}$ are as defined above,
(8) —CO—($C_3$–$C_{12}$ alkyl),
(9) —CO—($C_3$–$C_6$ cycloalkyl),
(10) —CO—$R_{1\text{-}heteroaryl}$ where $R_{1\text{-}heteroaryl}$ is as defined above,
(11) —CO—$R_{1\text{-}heterocycle}$ where $R_{1\text{-}heterocycle}$ is as defined above,
(12) —CO—$R_{N-4}$ where $R_{N-3}$ is as defined above,
(13) —CO—O—$R_{N-5}$ where $R_{N-4}$ is as defined above,
(14) —$SO_2$—$NR_{N-2}R_{N-3}$ where $R_{N-2}$ and $R_{N-3}$ are as defined above,
(15) —SO—($C_1$–$C_8$ alkyl),
(16) —$SO_2$—($C_3$–$C_{12}$ alkyl),
(17) —NH—CO—O—$R_{N-5}$ where $R_{N-5}$ is as defined above,
(18) —NH—CO—N($C_1$–$C_3$ alkyl)$_2$,
(19) —N—CS—N($C_1$–$C_3$ alkyl)$_2$,
(20) —N($C_1$–$C_3$ alkyl)—CO—$R_{N-5}$ where $R_{N-5}$ is as defined above,
(21) —$NR_{N-2}R_{N-3}$ where $R_{N-2}$ and $R_{N-3}$ can be the same or different and are as defined above,
(22) —$R_{N-4}$ where $R_{N-4}$ is as defined above,
(23) —O—CO—($C_1$–$C_6$ alkyl),
(24) —O—CO—N($C_1$–$C_3$ alkyl)$_2$,
(25) —O—CS—N($C_1$–$C_3$ alkyl)$_2$,
(26) —O—($C_1$–$C_6$ alkyl),
(27) —O—($C_2$–$C_5$ alkyl)—COOH, or
(28) —S—($C_1$–$C_6$ alkyl),
(29) ($C_1$–$C_6$ alkyl) substituted with —CO—OH and —NH—C(=O)—, (C) —$R_{N\text{-}aryl}$—$R_{N\text{-}aryl}$ where —$R_{N\text{-}aryl}$ is as defined above,
(D) —$R_{N\text{-}aryl}$—$R_{N\text{-}heteroaryl}$ where —$R_{N\text{-}aryl}$ and —$R_{N\text{-}heteroaryl}$ are as defined above,
(E) —$R_{N\text{-}heteroaryl}$—$R_{N\text{-}aryl}$ where —$R_{N\text{-}aryl}$ and —$R_{N\text{-}heteroaryl}$ are as defined above,
(F) —$R_{N\text{-}heteroaryl}$—$R_{N\text{-}heteroaryl}$ where —$R_{N\text{-}heteroaryl}$ is as defined above, (II) —CO—($C_1$–$C_6$ alkyl) where alkyl is unsubstituted or substituted with:
(A) —OH,
(B) —$C_1$–$C_6$ alkoxy,
(C) —$C_1$–$C_6$ thioalkoxy,
(D) —CO—O—$R_{N-8}$ where $R_{N-8}$ is —H, $C_1$–$C_6$ alkyl or -phenyl, (E) —CO—NR$_{N-2}$R$_{N-3}$ where R$_{N-2}$ and R$_{N-3}$ are the same or different and are as defined above,
(F) —CO—R$_{N-4}$ where R$_{N-4}$ is as defined above,
(G) —SO$_2$—(C$_1$–C$_8$ alkyl),
(H) —SO$_2$—NR$_{N-2}$R$_{N-3}$ where R$_{N-2}$ and R$_{N-3}$ are the same or different and are as defined above,
(I) —NH—CO—(C$_1$–C$_6$ alkyl),
(J) —NH—CO—O—R$_{N-8}$ where R$_{N-8}$ is as defined above,
(K) —NR$_{N-2}$R$_{N-3}$ where R$_{N-2}$ and R$_{N-3}$ are the same or different and are as defined above,
(L) —R$_{N-4}$ where R$_{N-4}$ is as defined above,
(M) —O—CO—(C$_1$–C$_6$ alkyl),
(N) —O—CO—NR$_{N-8}$R$_{N-8}$ where R$_{N-8}$ are the same or different and are as defined above, or
(O) —O—(C$_1$–C$_5$ alkyl)—COOH;
wherein R$_1$ is:
(I) C$_1$–C$_6$ alkyl,
(II) C$_1$–C$_6$ alkyl-S-alkyl
(III) C$_1$–C$_6$ alkyl-(C$_2$–C$_6$ alkenyl),
(IV) —(CH$_2$)$_{0-6}$-alkyl-(R$_{1-aryl}$) where R$_{1-aryl}$ is phenyl, 1-naphthyl, 2-naphthyl, indanyl, indenyl, dihydronaphthyl, or tetralinyl and is unsubstituted or substituted with:
　(A) C$_1$–C$_6$ alkyl,
　(B) —CF$_3$,
　(C) —F, Cl, —Br or —I,
　(D) C$_1$–C$_3$ alkoxy,
　(E) —O—CF$_3$,
　(F) —NH$_2$,
　(G) —OH, or
　(H) —C≡N,
(V) —(CH$_2$)$_{0-6}$-alkyl —(R$_{1-heteroaryl}$) where R$_{1-heteroaryl}$ is:
　(A) pyridinyl,
　(B) pyrimidinyl,
　(C) quinolinyl,
　(D) indenyl,
　(E) indanyl,
　(F) benzothiophenyl,
　(G) indolyl,
　(H) indolinyl,
　(I) pyridazinyl,
　(J) pyrazinyl,
　(K) isoindolyl,
　(L) isoquinolyl,
　(M) quinazolinyl,
　(N) quinoxalinyl,
　(O) phthalazinyl,
　(P) imidazolyl,
　(Q) isoxazolyl,
　(R) pyrazolyl,
　(S) oxazolyl,
　(T) thiazolyl,
　(U) indolizinyl,
　(V) indazolyl,
　(W) benzothiazolyl,
　(X) benzimidazolyl,
　(Y) benzofuranyl,
　(Z) furanyl,
　(AA) thienyl,
　(BB) pyrrolyl,
　(CC) oxadiazolyl,
　(DD) thiadiazolyl,
　(EE) triazolyl,
　(FF) tetrazolyl,
　(GG) 1,4-benzodioxan
　(HH) purinyl,
　(II) oxazolopyridinyl,
　(JJ) imidazopyridinyl,
　(KK) isothiazolyl,
　(LL) naphthyridinyl,
　(MM) cinnolinyl,
　(NN) carbazolyl,
　(OO) β-carbolinyl,
　(PP) isochromanyl,
　(QQ) chromanyl,
　(RR) furazanyl,
　(SS) tetrahydroisoquinoline,
　(TT) isoindolinyl,
　(UU) isobenzotetrahydrofuranyl,
　(VV) isobenzotetrahydrothienyl,
　(WW) isobenzothiophenyl,
　(XX) benzoxazolyl, or
　(YY) pyridopyridinyl,
　where the R1-heteroaryl group is bonded to -alkyl by any ring atom of the parent R$_{1-heteroaryl}$ group substituted by hydrogen such that the new bond to the R$_{1-heteroaryl}$ group replaces the hydrogen atom and its bond, where R$_{1-heteroaryl}$ is unsubstituted or substituted with:
　　(1) C$_1$–C$_3$ alkyl,
　　(2) —CF$_3$,
　　(3) —F, Cl, —Br, or I,
　　(4) C$_1$–C$_3$ alkoxy,
　　(5) —O—CF$_3$,
　　(6) —NH$_2$,
　　(7) —OH, or
　　(8) —C≡N,
(VI) —(R$_{1-heteroaryl}$) where R$_{1-heteroaryl}$ is as defined above,
(VII) —C$_1$–C$_5$ alkyl-(R$_{1-heterocycle}$) where R$_{1-heterocycle}$ is:
　(A) morpholinyl,
　(B) thiomorpholinyl,
　(C) thiomorpholinyl S-oxide,
　(D) thiomorpholinyl S,S-dioxide,
　(E) piperazinyl,
　(F) homopiperazinyl,
　(G) pyrrolidinyl,
　(H) pyrrolinyl,
　(I) tetrahydropyranyl,
　(J) piperidinyl,
　(K) tetrahydrofuranyl, or
　(L) tetrahydrothiophenyl,
　where the R$_{1-heterocycle}$ group is bonded by any atom of the parent R$_{1-heterocycle}$ group substituted by hydrogen such that the new bond to the R$_{1-heterocycle}$ group replaces the hydrogen atom and its bond, where R$_{1-heterocycle}$ is unsubstituted or substituted with:
　　(1) =O
　　(2) C$_1$–C$_3$ alkyl,
　　(3) —CF$_3$,
　　(4) —F, Cl, —Br or —I,
　　(5) C$_1$–C$_3$ alkoxy,
　　(6) —OCF$_3$,
　　(7) —NH$_2$,
　　(8) —OH, or
　　(9) —C≡N, or (VIII) —$R_{1\text{-}heterocycle}$, where $R_{1\text{-}heterocycle}$ is as defined above;

where $R_2$ is:

(I) —H, (II) $C_1$–$C_6$ alkyl, or (III) —$(CH_2)_{0-4}$—$R_{2-1}$ where $R_{2-1}$ is $(C_3$–$C_6)$cycloalkyl, $R_{1\text{-}aryl}$ or $R_{1\text{-}heteroaryl}$ where $R_{1\text{-}aryl}$ and $R_{1\text{-}heteroaryl}$ are as defined above;

where $R_3$, $R_4$, and $R_5$, are each independently —H, —$CH_3$, —$CH(CH_3)_2$, —$CH_2CH(CH_3)_2$, —CH(CH)$CH_2CH_3$, —$CH_2CH_2$*$CH_2$, wherein the *$CH_2$ is bonded to the adjacent NH to form a five membered heterocycle, —$CH_2$-phenyl, —$CH_2$(phenol), —$CH_2$—(3-indole), —$CH_2SH$, —$CH_2CH_2SCH_3$, —$CH_2OH$, —$CH(OH)CH_3$, —CH2CH2CH2NH$_3^+$, —$CH_2CH_2CH_2(NH)C(=NH_2^+)NH_2$, —$CH_2$—(5-(3H-imidazol-1-ium)), —$CH_2COO^-$, —$CH_2CH_2COO^-$, $CH_2CONH_2$, or —$CH_2CH_2CONH_2$;

where x is 1 or 0; and where y is 1 or 0, or pharmaceutically acceptable salts thereof.

The present invention also includes a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which includes administration of a therapeutically effective amount of a compound of formula (XII), (XIII), or (XIV)

Disclosed is the use of compounds of formula (XII), (XIII), or (XIV)

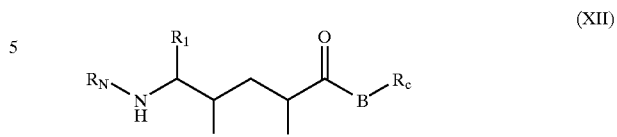

(XII)

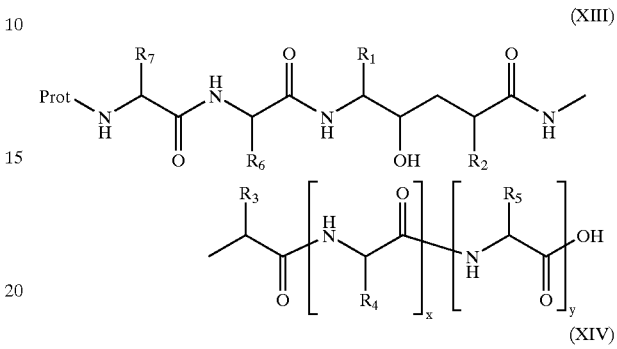

(XIII)

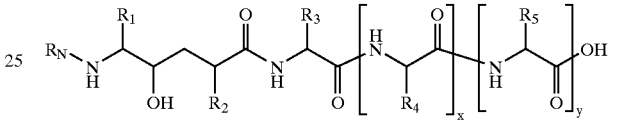

(XIV)

and pharmaceutically acceptable salts thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humnans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and

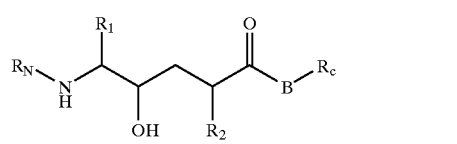

(XII)

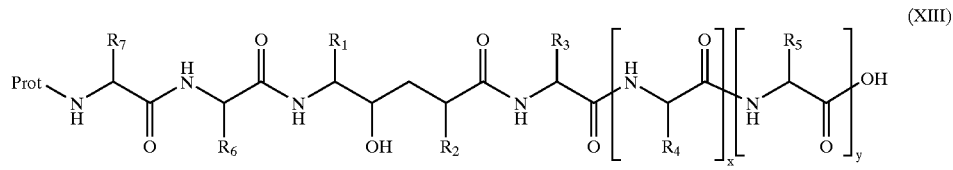

(XIII)

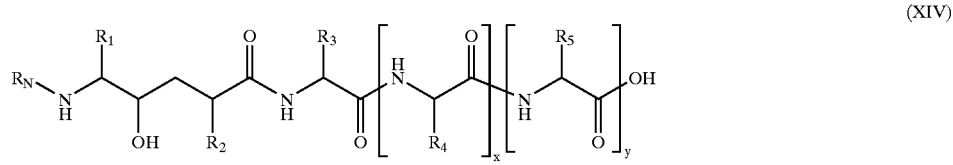

(XIV)

degenerative origin, dementia associated with Parkinson's disease, dementia associated with progressive supranuclear palsy, dementia associated with cortical basal degeneration, diffuse Lewy body type of Alzheimer's disease and who is in need of such treatment.

The present invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain. These methods each include administration of a therapeutically effective amount of compounds of formula (XII), (XIII), or (XIV):

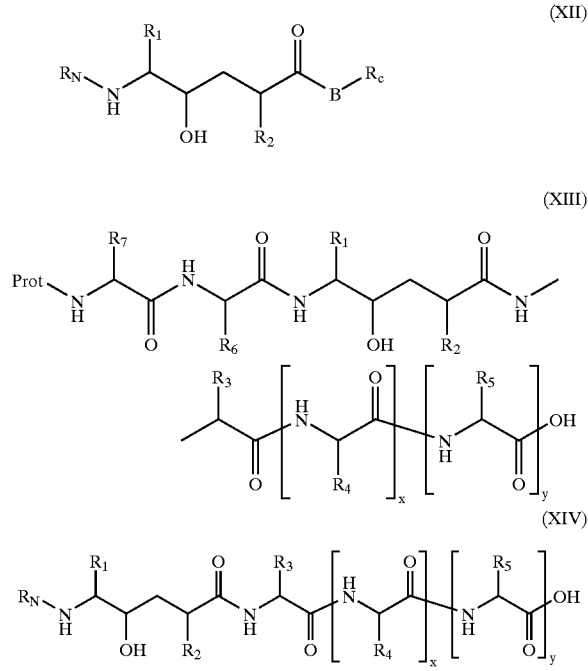

or a pharmaceutically acceptable salt thereof.

The present invention also includes a method for inhibiting beta-secretase activity, including exposing said beta-secretase to an effective inhibitory amount of compounds of formula (XII), (XIII), or (XIV):

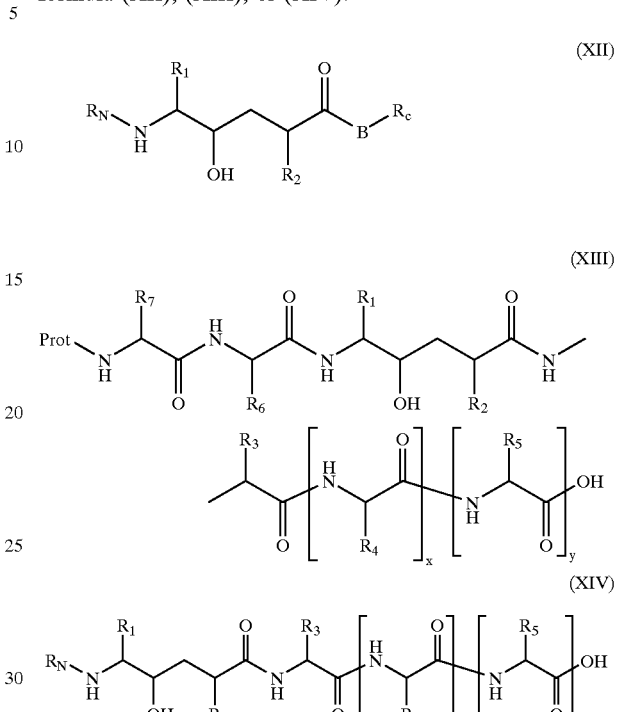

or a pharmaceutically acceptable salt thereof.

The present invention also includes a method for inhibiting cleavage of amyloid precursor protein (APP), in a reaction mixture, at a site between Met596 and Asp597, numbered for the APP-695 amino acid isotype; or at a corresponding site of an isotype or mutant thereof, including exposing said reaction mixture to an effective inhibitory amount of compounds of formula (XII), (XIII), or (XIV):

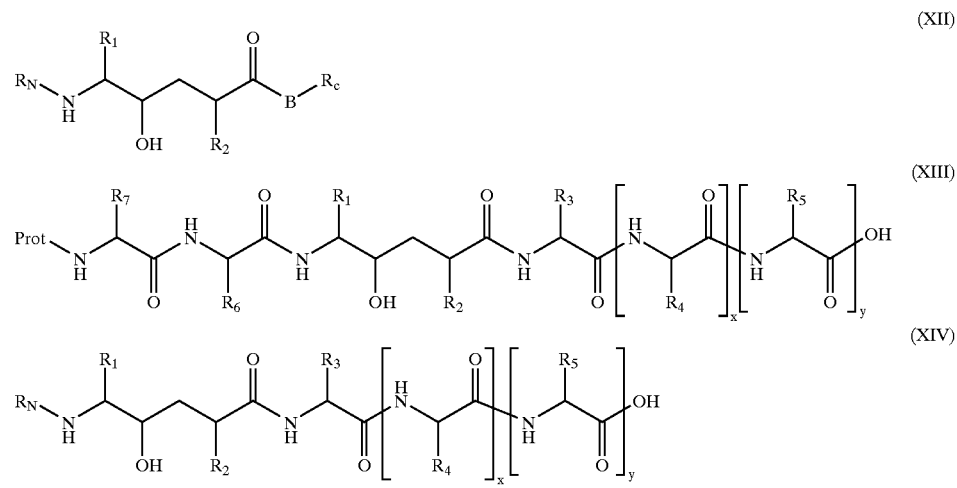

or a pharmaceutically acceptable salt thereof.

The present invention also includes a method for inhibiting production of amyloid beta peptide (A beta) in a cell, including administering to said cell an effective inhibitory amount of compounds of formula (XII), (XIII), or (XIV):

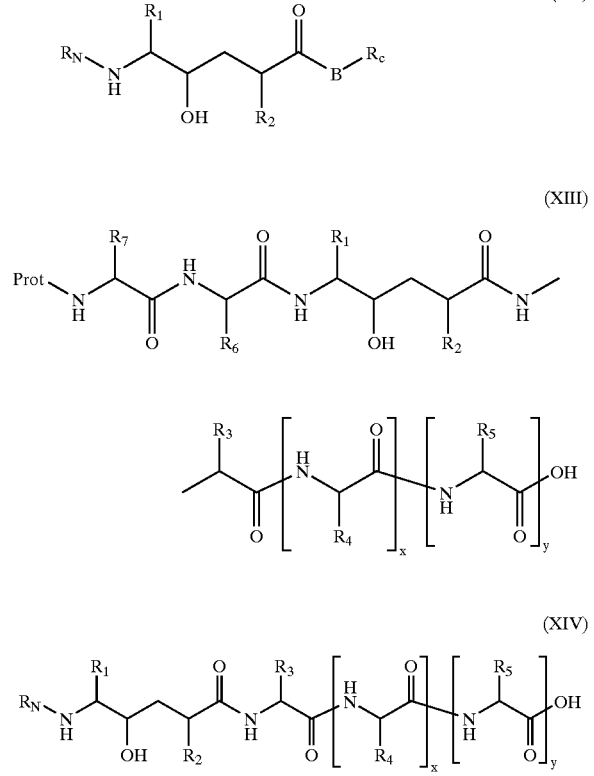

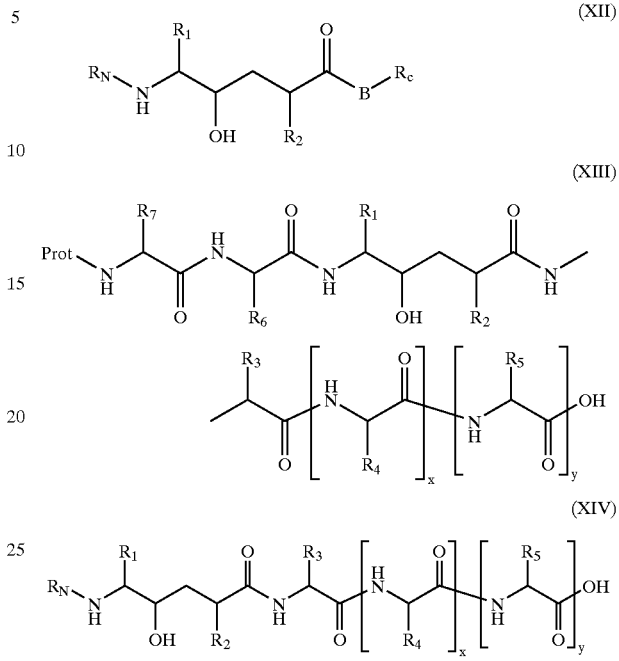

or a pharmaceutically acceptable salt thereof.

The present invention also includes a method for inhibiting the production of beta-amyloid plaque in an animal, including administering to said animal an effective inhibitory amount of compounds of formula (XII), (XIII), or (XIV):

or a pharmaceutically acceptable salt thereof.

The present invention also includes a method for treating or preventing a disease characterized by beta-amyloid deposits in the brain including administering to a patient an effective therapeutic amount of compounds of formula (XII), (XJII), or (XIV):

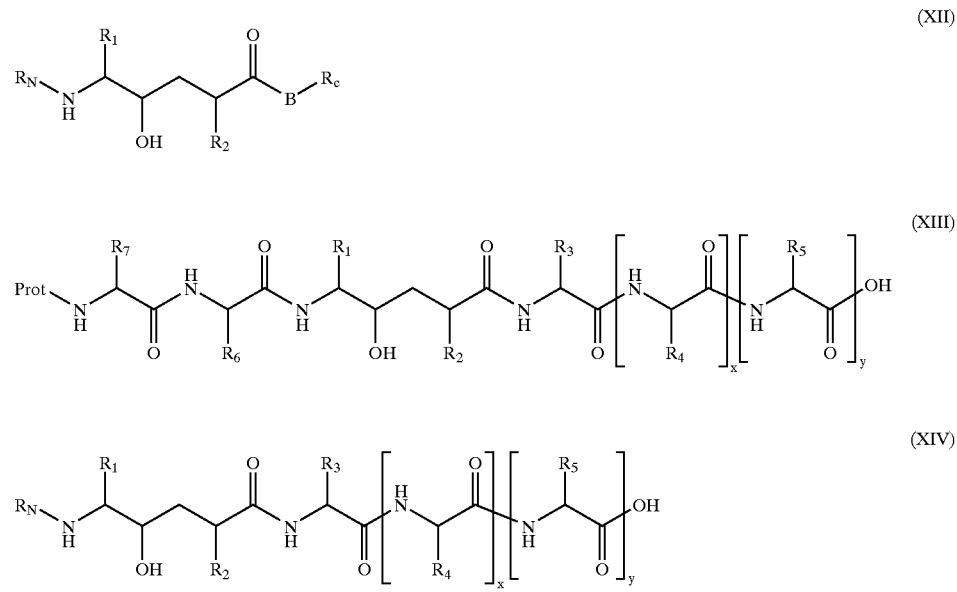

or a pharmaceutically acceptable salt thereof.

The present invention also includes a composition including beta-secretase complexed with compounds of formula (XII), (XIII), or (XIV):

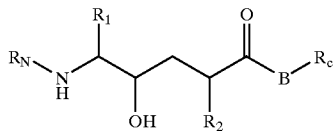
(XII)

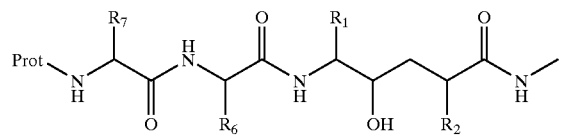
(XIII)

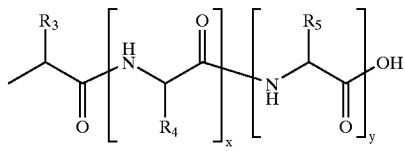

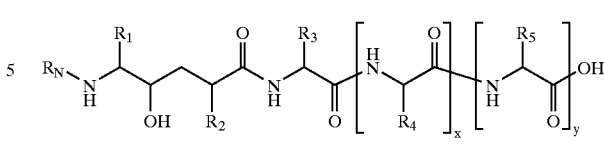
(XIV)

or a pharmaceutically acceptable salt thereof.

The present invention also includes a method for producing a beta-secretase complex including exposing beta-secretase to a compound of formula (I):

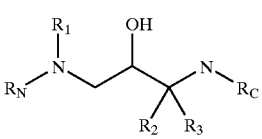
(I)

where $R_1$, $R_2$, $R_3$, $R_C$, and $R_N$ are as defined above, or a pharmaceutically acceptable salt thereof, in a reaction mixture under conditions suitable for the production of said complex.

The present invention also includes a component kit including component parts capable of being assembled, in which at least one component part includes compounds of formula (XII), (XIII), or (XIV) enclosed in a container.

The present invention also includes a container kit including a plurality of containers, each container including one or more unit dose of compounds of formula (XII), (XIII), or (XIV):

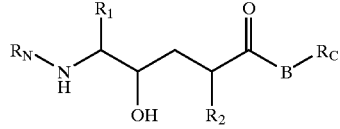
(XII)

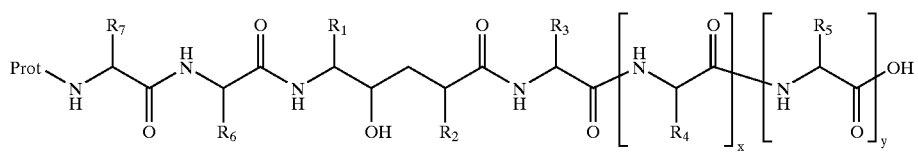
(XIII)

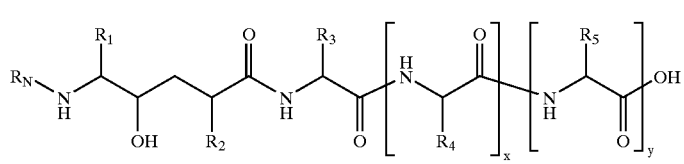
(XIV)

or a pharmaceutically acceptable salt thereof.

The present invention also includes an agent kit including compounds of formula (XII), (XIII), or (XIV):

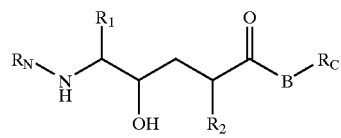

(XII)

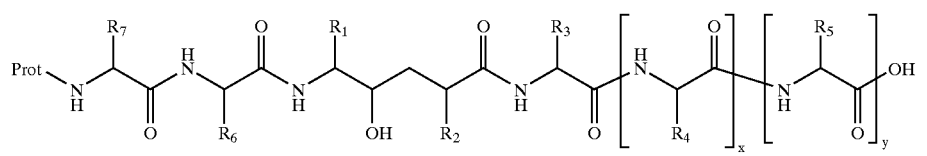

(XIII)

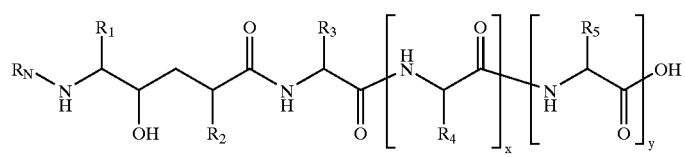

(XIV)

or a pharmaceutically acceptable salt thereof; and one or more therapeutic agents selected from the group consisting of an antioxidant, an anti-inflammatory, a gamma secretase inhibitor, a neurotrophic agent, an acetyl cholinesterase inhibitor, a stalin, an A beta peptide, and an anti-A beta antibody.

The present invention also includes a composition including: compounds of formula (XII), (XIII), or (XIV):

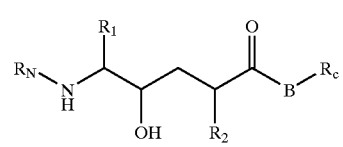

(XII)

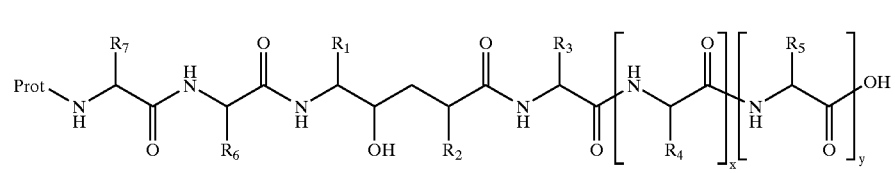

(XIII)

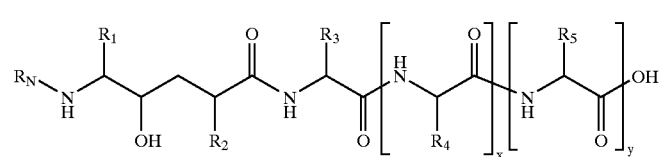

(XIV)

or a pharmaceutically acceptable salt thereof; and an inert diluent or edible carrier.

The present invention also includes a composition including: compounds of formula (XII), (XIII), or (XIV):

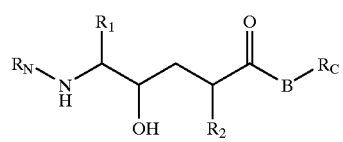
(XII)

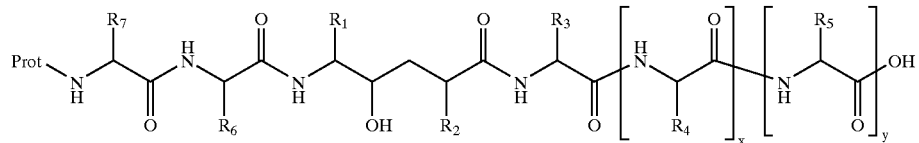
(XIII)

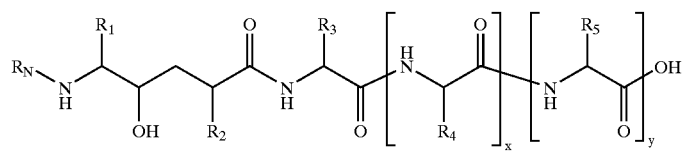
(XIV)

or a pharmaceutically acceptable salt thereof; and a binder, excipient, disintegrating agent, lubricant, or glidant.

The present invention also includes a composition including: compounds of formula (XII), (XIII), or (XIV):

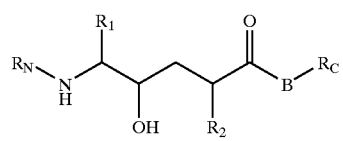
(XII)

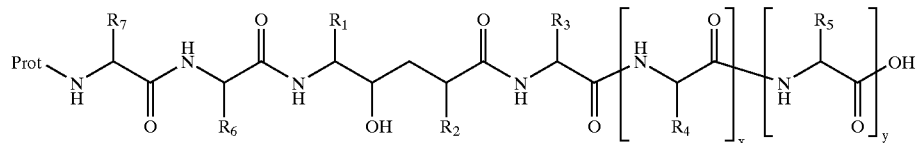
(XIII)

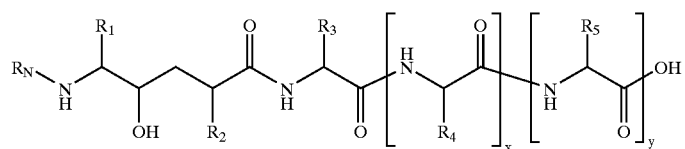
(XIV)

or a pharmaceutically acceptable salt thereof; disposed in a cream, ointment, or patch.

The present invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity. The inhibitory activities of the compounds of the invention are readily demonstrated, for example, using one or more of the assays described herein or known in the art.

DETAILED DESCRIPTION OF THE INVENTION

The present invention provides hydroxyethylene compounds of formula (XII) which are useful in treating and preventing Alzheimer's disease. The anti-Alzheimer's hydroxyethylene compounds of formula (XII) are made by methods well known to those skilled in the art from starting compounds known to those skilled in the art. The process chemistry is well known to those skilled in the art. The most general process to prepare the hydroxyethylene compounds of formula (XII) is set forth in CHART A, as defined within. The chemistry is straight forward and in summary involves the steps of N-protecting an amino acid (I) starting material to produce the corresponding protected amino acid (II), amino-dehydroxylation of the protected amino acid (II) with the appropriate amine in the presence of a coupling agent to produce the corresponding protected amide (III), reduction of the protected amide to the corresponding aldehyde (IV), formation of the terminal olefin as described (V), peracid epoxidation of the olefin (V) to produce the corresponding epoxide (VI), opening of the epoxide (VI) with an amide (VII) to produce the corresponding protected alcohol (VIII), cyclization of the protected alcohol (VIII) to produce the protected lactone (IX) which then has the nitrogen protecting group removed to produce the corresponding amine (X), which is then reacted with an amide forming agent of the formula $(R_{N-1}-X_N)_2O$ or $R_{N-1}-X_N-X_2$ or $R_{N-1}-X_N-OH$, for example, to produce the lactone (XI), opening of the lactone (XI) with a C-terminal amine, $R_C-NH_2$ to produce the anti-Alzheimer hydroxyethylene compounds of formula (XII). One skilled in the art will appreciate that these are all well known reactions in organic chemistry. A chemist skilled in the art, knowing the chemical structure of the biologically active hydroxyethylene compounds of formula (XII) would be able to prepare them by known methods from known starting materials without any additional information. The explanation below therefore is not necessary but is deemed helpful to those skilled in the art who desire to make the compounds of the present invention.

The backbone of the compounds of the present invention is a hydroxyethylene moiety. It can be readily prepared by methods disclosed in the literature and known to those skilled in the art. For example, Henning, R. "Synthetic Routes to Different Classes of Natural Products and Analogs Thereof. Synthesis of Hydroxyethylene Isosteric Dipeptides." In Organic Synthesis Highlights II; VCH: Weinheim, Germany, 1995; pp 251–259 discloses processes to prepare hydroxyethylene type compounds.

CHART A, as defined within, sets forth a general method used in the present invention to prepare the appropriately substituted hydroxyethylene compounds of formula (XII). The anti-Alzheimer hydroxyethylene compounds of formula (XII) are prepared by starting with the corresponding amino acid (I). The amino acids (I) are well known to those skilled in the art or can be readily prepared from known compounds by methods well known to those skilled in the art. The hydroxyethylene compounds of formula (XII) have at least three enantiomeric centers which give 8 enantiomers, the S, S, R stereochemistry being preferred. The first of these enantiomeric centers derives from the amino acid starting material (I). It is preferred to commercially obtain or produce the desired enantiomer (S) rather than produce an enantiomerically impure mixture and then have to separate out the desired enantiomer (S). It is preferred to start the process with enantiomerically pure (S)-amino acid (I) of the same configuration as that of the hydroxyethylene product. For the amino acids (I), $R_1$ is:

(I) $C_1$–$C_6$ alkyl,
(II) $C_1$–$C_6$ alkyl-S-alkyl
(III) $C_1$–$C_6$ alkyl-($C_2$–$C_6$ alkenyl),
(IV) —$(CH_2)_{0-6}$-alkyl-($R_{1-aryl}$) where $R_{1-aryl}$ is phenyl, 1-naphthyl, 2-naphthyl, indanyl, indenyl, dihydronaphthyl, or tetralinyl and is unsubstituted or substituted with:
(A) $C_1$–$C_6$ alkyl,
(B) —$CF_3$,
(C) —F, Cl, —Br or —I,
(D) $C_1$–$C_3$ alkoxy,
(E) —O—$CF_3$,
(F) —$NH_2$,
(G) —OH, or
(H) —CN,
(V) —$(CH_2)_{0-6}$-alkyl —($R_{1-heteroaryl}$) where $R_{1-heteroaryl}$ is:
(A) pyridinyl,
(B) pyrimidinyl,
(C) quinolinyl,
(D) indenyl,
(E) indanyl,
(F) benzothiophenyl,
(G) indolyl,
(H) indolinyl,
(I) pyridazinyl,
(J) pyrazinyl,
(K) isoindolyl,
(L) isoquinolyl,
(M) quinazolinyl,
(N) quinoxalinyl,
(O) phthalazinyl,
(P) imidazolyl,
(Q) isoxazolyl,
(R) pyrazolyl,
(S) oxazolyl,
(T) thiazolyl,
(U) indolizinyl,
(V) indazolyl,
(W) benzothiazolyl,
(X) benzimidazolyl,
(Y) benzofuranyl,
(Z) furanyl,
(AA) thienyl,
(BB) pyrrolyl,
(CC) oxadiazolyl,
(DD) thiadiazolyl,
(EE) triazolyl,
(FF) tetrazolyl,
(GG) 1,4-benzodioxan,
(HH) purinyl,
(II) oxazolopyridinyl,
(JJ) imidazopyridinyl,
(KK) isothiazolyl,
(LL) naphthyridinyl,
(MM) cinnolinyl,
(NN) carbazolyl,
(OO) β-carbolinyl,
(PP) isochromanyl,
(QQ) chromanyl,
(RR) furazanyl,
(SS) tetrahydroisoquinoline,
(TT) isoindolinyl,
(UU) isobenzotetrahydrofuranyl,
(VV) isobenzotetrahydrothienyl,
(WW) isobenzothiophenyl,
(XX) benzoxazolyl, or
(YY) pyridopyridinyl,
where the $R_{1-heteroaryl}$ group is bonded to -alkyl- by any ring atom of the parent $R_{1-heteroaryl}$ group substituted by hydrogen such that the new bond to the $R_{1-heteroaryl}$ group replaces the hydrogen atom and its bond, where $R_{1-heteroaryl}$ is unsubstituted or substituted with:

(1) $C_1$–$C_3$ alkyl,
(2) —$CF_3$,
(3) —F, Cl, —Br, or I,
(4) $C_1$–$C_3$ alkoxy,
(5) —O—$CF_3$,
(6) —$NH_2$,
(7) —OH, or
(8) —C≡N, (VI) —($R_{1\text{-}heteroaryl}$) where $R_{1\text{-}heteroaryl}$ is as defined above, (VII) —$C_1$–$C_5$ alkyl-($R_{1\text{-}heterocycle}$) where $R_{1\text{-}heterocycle}$ is:
(A) morpholinyl,
(B) thiomorpholinyl,
(C) thiomorpholinyl S-oxide,
(D) thiomorpholinyl S,S-dioxide,
(E) piperazinyl,
(F) homopiperazinyl,
(G) pyrrolidinyl,
(H) pyrrolinyl,
(I) tetrahydropyranyl,
(J) piperidinyl,
(K) tetrahydrofuranyl, or
(L) tetrahydrothiophenyl,
where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where $R_{1\text{-}heterocycle}$ is unsubstituted or substituted with:
(1) =O,
(2) $C_1$–$C_3$ alkyl,
(3) —$CF_3$,
(4) —F, Cl, —Br or —I,
(5) $C_1$–$C_3$ alkoxy,
(6) —O—$CF_3$,
(7) —$NH_2$,
(8) —OH, or
(9) —C≡N, or (VIII) —$R_{1\text{-}heterocycle}$, where $R_{1\text{-}heterocycle}$ is as defined above;

When $R_1$ is $R_{1\text{-}heteroaryl}$ or $R_{1\text{-}heterocycle}$ the bond from the $R_{1\text{-}heteroaryl}$ or $R_{1\text{-}heterocycle}$ group to the —$(CH_2)_{n1}$— group can be from any ring atom which has an available valence provided that such bond does not result in formation of a charged species or unstable valence. This means that the $R_{1\text{-}heteroaryl}$ or $R_{1\text{-}heterocycle}$ group is bonded to —$(CH_2)_{n1}$— by any ring atom of the parent $R_{1\text{-}heteroaryl}$ or $R_{1\text{-}heterocycle}$ group which was substituted by hydrogen such that the new bond to the $R_{1\text{-}heteroaryl}$ or $R_{1\text{-}heterocycle}$ group replaces the hydrogen atom and its bond.

It is preferred that $R_1$ is $C_1$–$C_6$ alkyl. It is more preferred that $R_1$ is —$C_4$ alkyl. It is even more preferred that $R_1$ is —$CH_2CH(CH_3)_2$.

The first step of the process is to protect the free amino group of the (S)-amino acid (I) with an amino protecting group to produce the (S)-protected amino acid (II) by methods well known to those skilled in the art. Amino protecting groups are well known to those skilled in the art. See for example, "Protecting Groups in Organic Synthesis", John Wiley and sons, New York, N.Y., 2nd ed., 1991, Chapter 7; "Protecting Groups in Organic Chemistry", Plenum Press, New York, N.Y., 1973, Chapter 2. The function of the amino protecting group is to protect the free amino functionality (—$NH_2$) during subsequent reactions on the (S)-amino acid (I) which would not proceed well either because the amino group would react and be functionalized in a way that is inconsistent with its need to be free for subsequent reactions or the free amino group would interfere in the reaction. When the amino protecting group is no longer needed, it is removed by methods well known to those skilled in the art. By definition the amino protecting group must be readily removable as is known to those skilled in the art by methods well known to those skilled in the art. Suitable amino PROTECTING GROUPs include t-butoxycarbonyl, benzyloxycarbonyl, formyl, trityl, phthalimido, trichloroacetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcycoopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxazoylmethoxycarbonyl, 4-acetoxybenzyloxycarbonyl, 2,2,2-trichloroethoxycarbonyl, 2-ethynyl-2-propoxycarbonyl, cyclopropylmethoxyearbonyl, 4-(decyloxyl)benzyloxycarbonyl, isobornyloxycarbonyl, -phenyl-C(=N)—H, and 1-piperidyloxycarbonyl. It is preferred that the protecting group be t-butoxycarbonyl (BOC) and benzyloxycarbonyl (CBZ), it is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry, John Wiley and Sons, 2nd ed., 1991, at 327–335 for guidance.

The (S)-protected amino acid (II) is transformed to the corresponding (S)-protected amide compound (III) by means well known to those skilled in the art for the production of an amide from a carboxylic acid and an amine or hydroxylamine. The means and reaction conditions for producing the (S)-protected amide compound (III) include, for example, the use of a coupling agent such as, for example, dicyclohexylcarbodiimide, 1,1-carbonyldiimidazole, $POCl_3$, $TiCl_4$, $SO_2ClF$, benzotriazol-1-yl diethyl phosphate, or N,N,N',N'-tetramethyl(succinimido)uronium tetrafluoroborate in the presence of an amine or hydroxylamine. 1,1-Carbonyldiimidazole is a preferred coupling agent and N-methyl-O-methylhydroxylamine is a preferred hydroxylamine. The reaction is carried out for a period of time between 1 hour and 3 days at temperatures ranging from −78 degrees to elevated temperature up to the reflux point of the solvent employed. It is preferred to conduct the reaction between 0 degrees and 50 degrees.

The (S)-protected amide compound (III) is then reduced by means well known to those skilled in the art for reduction of a amide to the corresponding aldehyde, affording the corresponding aldehyde (IV). The means and reaction conditions for reducing the (S)-protected amide compound (III) to the corresponding aldehyde (IV) include, for example, sodium borohydride, lithium borohydride, borane, diisobutylaluminum hydride, and lithium aluminium hydride.

Lithium aluminium hydride is the preferred reducing agent. The reductions are carried out for a period of time between 1 hour and 3 days at temperatures ranging from −78 degrees to room temperature. It is preferred to conduct the reduction between −20 degrees and room temperature. The preferred combination of reducing agents and reaction conditions needed are known to those skilled in the art, see for example, Larock, R. C. in Comprehensive Organic Transformations, VCH Publishers, 1989.

The aldehyde (IV) is transformed to the corresponding olefin (V) by means known to those skilled in the art. An example of such a reaction is the reaction of the aldehyde (IV) with a phosphorous ylide to produce the desired olefin. Such phosphorous ylides include methyltriphenylphosphonium bromide. Reaction conditions include temperatures ranging from −100 degrees up to the reflux temperature of the solvent employed; preferred temperature ranges are between −100 degrees and 0 degrees.

Peracid epoxidation of the olefin (V) affords the epoxide (VI). Other methods for the conversion of an olefin to an epoxide are known to those skilled in the art. The means for producing the epoxide (VI) include, for example, the use of a peracid such as, for example, peracetic acid, perbenzoic, trifluoroperacetic acid, 3,5-dinitroperoxybenzoic acid, and m-chloroperbenzoic acid.

The epoxide (VI) is then reacted with the appropriate amide (VII) by means known to those skilled in the art which opens the epoxide to produce the desired corresponding protected alcohol (VIII). Reaction of the epoxide (VI) with the amide (VII) produces a mixture of enantiomers. This enantiomeric mixture is then separated by means known to those skilled in the art such as selective low-temperature recrystallization or chromatographic separation, most preferably by HPLC, employing commercially available chiral columns. The enantiomer that is used in the remainder of the process of CHART A is the (S,S,R)-alcohol (VIII).

The protected-alcohol (VIII) is transformed to the corresponding protected lactone (IX) by means known to those skilled in the art. A preferred means is by reaction with an acid catalyst, for example, but not limited to, p-toluenesulfonic acid and the like. Reactions are conducted at temperatures ranging from −78 degrees up to the reflux temperature of the solvent employed; preferred temperature ranges are between 0 degrees and 50 degrees.

The amine moiety or the protected lactone (IX) is deprotected to the corresponding amine (X) by means known to those skilled in the art for removal of amine protecting group. Suitable means for removal of the amine protecting group depends on the nature of the protecting group. Those skilled in the art, knowing the nature of a specific protecting group, know which reagent is preferable for its removal. For example, it is preferred to remove the preferred protecting group, BOC, by dissolving the protected lactone (IX) in a trifluoroacetic acid/dichloromethane mixture. When complete, the solvents are removed under reduced pressure to give the corresponding lactone (as the corresponding salt, i.e. trifluoroacetic acid salt) which is used without further purification. However, if desired, the lactone can be purified further by means well known to those skilled in the art, such as for example, recrystallization. Further, if the non-salt form is desired that also can be obtained by means known to those skilled in the art, such as for example, preparing the free base amine via treatment of the salt with mild basic conditions. Additional BOC deprotection conditions and deprotection conditions for other protecting groups can be found in T. W. Green and P. G. M. Wuts in "Protective Groups in Organic Chemistry, John Wiley and Sons, 1991, p. 309 and following. Chemically suitable salts include trifluoroacetate, and the anion of mineral acids such as chloride, sulfate, phosphate; preferred is trifluoroacetate.

The amine (X) is then reacted with an appropriately substituted-amide-forming-agent such as anhydride, acyl halide, or acid of the formula $(R_{N-1}-X_N)_2O$ or $R_{N-1}-X_N-X_2$ or $R_{N-1}-X_N-OH$ by nitrogen-acylation means known to those skilled in the art to produce the corresponding lactone (XI). Nitrogen acylation conditions for reaction of the amine (X) with an amide forming agent to produce the corresponding lactone (XI) are known to those skilled in the art and can be found in R. C. Larock in Comprehensive Organic Transformations, VCH Publishers, 1989, p. 981, 979, and 972. $R_N$ includes:

(I) $R_{N-1}-X_N-$ where $X_N$ is:
  (A) —CO—,
  (B) —SO$_2$—,
  (C) —(CR'R")$_{1-6}$ where R' and R" are the same or different and are —H or C$_1$–C$_4$ alkyl,
  (D) —CO—(CR'R")$_{1-6}$—X$_{N-1}$ where X$_{N-1}$ is —O—, —S— or —NR'R"— and where R' and R" are as defined above, or
  (E) a single bond;
where $R_{N-1}$ is:
  (A) $R_{N-aryl}$ where $R_{N-aryl}$ is phenyl, biphenyl, 1-naphthyl, 2-naphthyl, indanyl, indenyl, dihydronaphthyl, or tetralinyl and is unsubstituted or substituted with:
    (1) C$_1$–C$_6$ alkyl,
    (2) —F, —Cl, —Br, or —I,
    (3) —OH,
    (4) —NO$_2$,
    (5) —CO—OH,
    (6) —C≡N,
    (7) —CO—NR$_{N-2}$R$_{N-3}$ where R$_{N-2}$ and R$_{N-3}$ are the same or different and are:
      (a) —H,
      (b) —C$_1$–C$_6$ alkyl unsubstituted or substituted with
        (i) —OH, or
        (ii) —NH$_2$,
      (c) —C$_1$–C$_6$ alkyl unsubstituted or substituted with —F, —Cl, —Br, or —I,
      (d) —C$_3$–C$_7$ cycloalkyl,
      (e) —(C$_1$–C$_2$ alkyl)—(C$_3$–C$_7$ cycloalkyl),
      (f) —(C$_1$–C$_6$ alkyl)—O—(C$_1$–C$_3$ alkyl),
      (g) —C$_1$–C$_6$ alkenyl with one or two double bonds,
      (h) —C$_1$–C$_6$ alkynyl with one or two triple bonds,
      (i) —C$_1$–C$_6$ alkyl chain with one double bond and one triple bond,
      (j) —R$_{1-aryl}$ where R$_{1-aryl}$ is as defined above, or
      (k) R$_{1-heteroaryl}$ where R$_{1-heteroaryl}$ is as defined above,
    (8) —CO—(C$_3$–C$_{12}$ alkyl),
    (9) —CO—(C$_3$–C$_6$ cycloalkyl),
    (10) CO—R$_{1-heteroaryl}$ where R$_{1-heteroaryl}$ is as defined above,
    (11) —CO—R$_{1-heterocycle}$ where R$_{1-heterocycle}$ is as defined above,
    (12) —CO—R$_{N-4}$ where R$_{N-4}$ is morpholinyl, thiomorpholinyl, piperazinyl, piperidinyl or pyrrolidinyl where each group is unsubstituted or substituted with C$_1$–C$_3$ alkyl,

(13) —CO—O—$R_{N-5}$ where $R_{N-5}$ is:
  (a) alkyl, or
  (b) —$(CH_2)_{0-2}$—$(R_{1-aryl})$ where $R_{1-aryl}$ is as defined above,
(14) —$SO_2$—$NR_{N-2}R_{N-3}$ where $R_{N-2}$ and $R_{N-3}$ are as defined above,
(15) —SO—($C_1$-$C_8$ alkyl),
(16) —$SO_2$—($C_3$-$C_{12}$ alkyl),
(17) —NH—CO—O—$R_{N-5}$ where $R_{N-5}$ is as defined above,
(18) —NH—CO—N($C_1$-$C_3$ alkyl)$_2$,
(19) —N—CS—N($C_1$-$C_3$ alkyl)$_2$,
(20) —N($C_1$-$C_3$ alkyl)—CO—$R_{N-5}$ where $R_{N-5}$ is as defined above,
(21) —$NR_{N-2}R_{N-3}$ where $R_{N-2}$ and $R_{N-3}$ can be the same or different and are as defined above,
(22) —$R_{N-4}$ where $R_{N-4}$ is as defined above,
(23) —O—CO—($C_1$-$C_6$ alkyl),
(24) —O—CO—N($C_1$-$C_3$ alkyl)$_2$,
(25) —O—CS—N($C_1$-$C_3$ alkyl)$_2$,
(26) —O—($C_1$-$C_6$ alkyl),
(27) —O—($C_2$-$C_5$ alkyl)—COOH,
(28) —S—($C_1$-$C_6$ alkyl),
(29) $C_1$-$C_6$ alkyl unsubstituted or substituted with halo,
(30) —O—($C_1$-$C_6$ alkyl unsubstituted or substituted with halo), or
(31) —O-phenyl,
(32) ($C_1$-$C_6$ alkyl) substituted with —CO—NH—C(=O)—,
(B) —$R_{N-heteroaryl}$ where $R_{N-heteroaryl}$ is:
(1) pyridinyl,
(2) pyrimidinyl,
(3) quinolinyl,
(4) indenyl,
(5) indanyl,
(6) benzothiophenyl,
(7) indolyl,
(8) indolinyl,
(9) pyridazinyl,
(10) pyrazinyl,
(11) isoindolyl,
(12) isoquinolyl,
(13) quinazolinyl,
(14) quinoxalinyl,
(15) phthalazinyl,
(16) imidazolyl,
(17) isoxazolyl,
(18) pyrazolyl,
(19) oxazolyl,
(20) thiazolyl,
(21) indolizinyl,
(22) indazolyl,
(23) benzothiazolyl,
(24) benzimidazolyl,
(25) benzofuranyl,
(26) furanyl,
(27) thienyl,
(28) pyrrolyl,
(29) oxadiazolyl,
(30) thiadiazolyl,
(31) triazolyl,
(32) tetrazolyl,
(33) 1,4-benzodioxan
(34) purinyl,
(35) oxazolopyridinyl,
(36) imidazopyridinyl,
(37) isothiazolyl,
(38) naphthyridinyl,
(39) cinnolinyl,
(40) carbazolyl,
(41) β-carbolinyl,
(42) isochromanyl,
(43) chromanyl,
(44) furazanyl,
(45) tetrahydroisoquinoline,
(46) isoindolinyl,
(47) isobenzotetrahydrofuranyl,
(48) isobenzotetrahydrothienyl,
(49) isobenzothiophenyl,
(50) benzoxazolyl, or
(51) pyridopyridinyl,
where the $R_{N-heteroaryl}$ group is bonded by any atom of the parent $R_{N-heteroaryl}$ group substituted by hydrogen such that the new bond to the $R_{N-heteroaryl}$ group replaces the hydrogen atom and its bond, where $R_{N-heteroaryl}$ is unsubstituted or substituted with:
  (1) $C_1$-$C_6$ alkyl,
  (2) —F, —Cl, —Br, or —I,
  (3) —OH,
  (4) —$NO_2$,
  (5) —CO—OH,
  (6) —C≡N,
  (7) —CO—$NR_{N-2}R_{N-3}$ where $R_{N-2}$ and $R_{N-3}$ are as defined above,
  (8) —CO—($C_3$-$C_{12}$ alkyl),
  (9) —CO—($C_3$-$C_6$ cycloalkyl),
  (10) —CO—$R_{1-heteroaryl}$ where $R_{1-heteroaryl}$ is as defined above,
  (11) —CO—$R_{1-heterocycle}$ where $R_{1-heterocycle}$ is as defined above,
  (12) —CO—$R_{N-4}$ where $R_{N-4}$ is as defined above,
  (13) —CO—O—$R_{N-5}$ where $R_{N-5}$ is as defined above,
  (14) —$SO_2$—$NR_{N-2}R_{N-3}$ where $R_{N-2}$ and $R_{N-3}$ are as defined above,
  (15) —SO—($C_1$-$C_8$ alkyl),
  (16) —$SO_2$—($C_3$-$C_{12}$ alkyl),
  (17) —NH—CO—O—$R_{N-5}$ where $R_{N-5}$ is as defined above,
  (18) —NH—CO—N($C_1$-$C_3$ alkyl)$_2$,
  (19) —N—CS—N($C_1$-$C_3$ alkyl)$_2$,
  (20) —N($C_1$-$C_3$ alkyl)—CO—$R_{N-5}$ where $R_{N-5}$ is as defined above,
  (21) —$NR_{N-2}R_{N-3}$ where $R_{N-2}$ and $R_{N-3}$ can be the same or different and are as defined above,
  (22) —$R_{N-5}$ where $R_{N-4}$ is as defined above,
  (23) —O—CO—($C_1$-$C_6$ alkyl),
  (24) —O—CO—N($C_1$-$C_3$ alkyl)$_2$,
  (25) —O—CS—N($C_1$-$C_3$ alkyl)$_2$,
  (26) —O—($C_1$-$C_6$ alkyl),
  (27) —O—($C_2$-$C_5$ alkyl)—COOH, or
  (28) —S—($C_1$-$C_6$ alkyl),
  (29) ($C_1$-$C_6$ alkyl) substituted with —CO—OH and —NH—C(=O)—,
(C) $R_{N-aryl}$—$R_{N-aryl}$ where —$R_{N-aryl}$ is as defined above,
(D) —$R_{N-aryl}$—$R_{N-heteroaryl}$ where —$R_{N-aryl}$ and —$R_{N-heteroaryl}$ are as defined above,
(E) —$R_{N-heteroaryl}$—$R_{N-aryl}$ where —$R_{N-aryl}$ and $R_{N-heteroaryl}$ are as defined above,
(F) —$R_{N-heteroaryl}$—$R_{N-heteroaryl}$ where $R_{N-heteroaryl}$ is as defined above, (G) —$R_{N\text{-}aryl}$—O—$R_{N\text{-}aryl}$ where —$R_{N\text{-}aryl}$ is as defined above,
(H) —$R_{N\text{-}aryl}$—S—$R_{N\text{-}aryl}$ where —$R_{N\text{-}aryl}$ is as defined above,
(I) —$R_{N\text{-}heteraryl}$-13 O—$R_{N\text{-}heteroaryl}$ where $R_{N\text{-}heteroaryl}$ is as defined above,
(J) —$R_{N\text{-}heternaryl}$—S—$R_{N\text{-}heteroaryl}$ where $R_{N\text{-}heteroaryl}$ is as defined above,
(K) —$R_{N\text{-}aryl}$—CO—$R_{N\text{-}aryl}$ where —$R_{N\text{-}aryl}$ is as defined above,
(L) —$R_{N\text{-}aryl}$—CO—$R_{N\text{-}heteroaryl}$ where —$R_{N\text{-}aryl}$ and $R_{N\text{-}heteroaryl}$ are as defined above,
(M) —$R_{N\text{-}aryl}$—SO$_2$—$R_{N\text{-}aryl}$ where —$R_{N\text{-}aryl}$ is as defined above,
(N) —$R_{N\text{-}heteroaryl}$—CO—$R_{N\text{-}heteroaryl}$ where $R_{N\text{-}heteroaryl}$ is as defined above,
(O) —$R_{N\text{-}heteroaryl}$—SO$_2$—$R_{N\text{-}heteroaryl}$ where $R_{N\text{-}heteroaryl}$ is as defined above,
(P) —$R_{N\text{-}aryl}$—O—(C$_1$–C$_8$ alkyl)-phenyl, where $R_{N\text{-}aryl}$ is as defined above,
(Q) —$R_{N\text{-}aryl}$—S—(C$_1$–C$_8$ alkyl)-phenyl, where $R_{N\text{-}aryl}$ is as defined above,
(R) —$R_{N\text{-}beteroaryl}$—O—(C$_1$–C$_8$ alkyl)-phenyl, where $R_{N\text{-}heteroaryl}$ is as defined above, or
(S) —$R_{N\text{-}heteroaryl}$—S—(C$_1$–C$_9$ alkyl)-phenyl, where $R_{N\text{-}heteroaryl}$ is as defined above, or (II) —CO—(C$_1$–C$_6$ alkyl) where alkyl is unsubstituted or substituted with:
(A) —OH,
(B) —C$_1$–C$_6$ alkoxy,
(C) —C$_1$–C$_6$ thioalkoxy,
(D) —CO—O—$R_{N\text{-}8}$ where $R_{N\text{-}8}$ is —H, C$_1$–C$_6$ alkyl or -phenyl,
(E) —CO—NR$_{N\text{-}2}$R$_{N\text{-}3}$ where R$_{N\text{-}2}$ and R$_{N\text{-}3}$ are the same or different and are as defined above,
(F) —CO—R$_{N\text{-}4}$ where R$_{N\text{-}4}$ is as defined above,
(G) —SO$_2$—(C$_1$–C$_8$ alkyl),
(H) —SO$_2$—NR$_{N\text{-}2}$R$_{N\text{-}3}$ where R$_{N\text{-}2}$ and R$_{N\text{-}3}$ are the same or different and are as defined above,
(I) —NH—CO—(C$_1$–C$_6$ alkyl),
(J) —NH—CO—O—R$_{N\text{-}8}$ where R$_{N\text{-}8}$ is as defined above,
(K) —NR$_{N\text{-}2}$R$_{N\text{-}3}$ where R$_{N\text{-}2}$ and R$_{N\text{-}3}$ are the same or different and are as defined above,
(L) —R$_{N\text{-}4}$ where R$_{N\text{-}4}$ is as defined above,
(M) —O—CO—(C$_1$–C$_6$ alkyl),
(N) —O—CO—NR$_{N\text{-}8}$R$_{N\text{-}8}$ where R$_{N\text{-}8}$ are the same or different and are as defined above, or
(O) —O—(C$_1$–C$_5$ alkyl)—COOH;

In an embodiment of the present invention it is preferred that R$_N$ is R$_{N\text{-}1}$X$_N$, where X$_N$ is —CO—, and R$_N$—, is substituted or unsubstituted R$_{N\text{-}aryl}$.

In one embodiment, it is preferred that R$_{N\text{-}aryl}$ is substituted or unsubstituted phenyl. It is more preferred that phenyl is substituted with —CONPr$_2$. It is most preferred, in this embodiment that R$_N$ is:

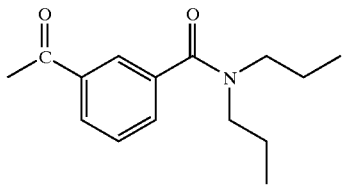

In another embodiment of the invention, it is preferred that R$_{N\text{-}aryl}$ is substituted or unsubstituted 1-naphthyl. It is more preferred that 1-naphthyl is substituted with —CH OH. It is most preferred, in this embodiment, that R$_N$ is:

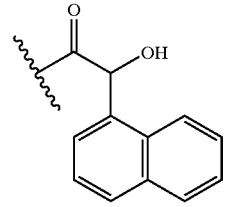

In yet another embodiment of the invention, it is preferred that R$_{N\text{-}aryl}$ is substituted or unsubstituted biphenyl. It is more preferred that biphenyl is substituted with —CH OH. It is most preferred, in this embodiment that R$_N$ is:

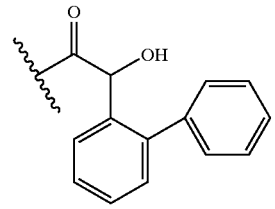

In even yet another embodiment of the invention, it is preferred that R$_{N\text{-}aryl}$ is substituted or unsubstituted phenyl. It is more preferred that phenyl be substituted with —CH OH and —Br. It is most preferred, in this embodiment, that R$_N$ is:

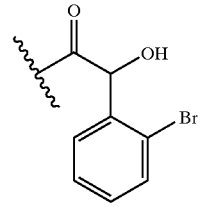

In other embodiments of the invention, it is preferrerd that R$_N$ is chosen from:
(II) —CO—(C$_1$–C$_6$ alkyl) where alkyl is unsubstituted or substituted with:
(A) —OH,
(B) —C$_1$–C$_6$ alkoxy,
(C) —C$_1$–C$_6$ thioalkoxy,
(D) —CO—O—R$_{N\text{-}8}$ where R$_{N\text{-}8}$ is —H, C$_1$–C$_6$ alkyl or -phenyl,
(E) —CO—NR$_{N\text{-}2}$R$_{N\text{-}3}$ where R$_{N\text{-}2}$ and R$_{N\text{-}3}$ are the same or different and are as defined above,
(F) —CO—R$_{N\text{-}4}$ where R$_{N\text{-}4}$ is as defined above,
(G) —SO$_2$—(C$_1$–C$_8$ alkyl),
(H) —SO$_2$—NR$_{N\text{-}2}$R$_{N\text{-}3}$ where R$_{N\text{-}2}$ and R$_{N\text{-}3}$ are the same or different and are as defined above,
(I) —NH—CO—(C$_1$–C$_6$ alkyl),
(J) —NH—CO—O—R$_{N\text{-}8}$ where R$_{N\text{-}8}$ is as defined above,
(K) —NR$_{N\text{-}2}$R$_{N\text{-}3}$ where R$_{N\text{-}2}$ and R$_{N\text{-}3}$ are the same or different and are as defined above,
(L) —R$_{N\text{-}4}$ where R$_{N\text{-}4}$ is as defined above,
(M) —O—CO—(C$_1$–C$_6$ alkyl),
(N) —O—CO—NR$_{N\text{-}8}$R$_{N\text{-}8}$ where R$_{N\text{-}8}$ are the same or different and are as defined above, or
(O) —O—(C$_1$–C$_5$ alkyl)—COOH.

In one embodiment, $R_N$ is substituted —CO—($C_1$-$C_6$ alkyl). It is preferred that $R_N$ is substituted with —OH, —$C_1$-$C_6$ thioalkoxy, —CO—O—$R_{N-8}$, where $R_{N-8}$ is —H, $C_1$-$C_6$ alkyl or —phenyl, or —CO—$NR_{N-2}R_{N-3}$, where $R_{N-2}$ and $R_{N-3}$ are the same or different and are as defined above. It is more preferred that $R_N$ is substituted —CO—($C_2$ alkyl). It is even more preferred that —CO—($C_2$ alkyl) is substituted with —CO—$NR_{N-2}R_{N-3}$. In this embodiment, it is most preferred that —CO—$NR_{N-2}R_{N-3}$ is —CO—$NH_2$. In this embodiment, the most preferred structure of $R_N$ is:

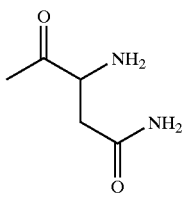

In another embodiment, $R_N$ is doubly substituted —CO—($C_1$-$C_6$ alkyl). In this embodiment, it is preferred that one of the substituents is —OH, —$C_1$-$C_6$ thioalkoxy, 13 CO—O—$R_{N-8}$, where $R_{N-8}$ is —H, $C_1$-$C_6$ alkyl or -phenyl, or —CO—$NR_{N-2}R_{N-3}$, where $R_{N-2}$ and $R_{N-3}$ are the same or different and are as defined above; and the other substituent is —NH—CO—($C_1$-$C_6$ alkyl). It is more preferred that —NH—CO—($C_1$-$C_6$ alkyl) is substituted. It is even more preferred that $C_1$-$C_6$ alkyl is doubly substituted $C_2$,alkyl, with one substituent —$CONH_2$ and the other substituent —NH—CO—$C_4$ alkyl. It is also most preferred that $C_4$ alkyl is substituted with —$NH_2$. In this embodiment, the most preferred structure of $R_N$ is

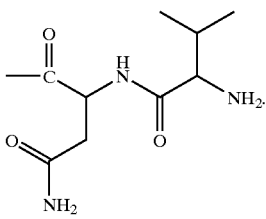

The nitrogen-acylation of primary amines to produce secondary amides is one of the oldest known reactions. The amide forming agents, ($R_{N-1}$—$X_N$)$_2$O or $R_{N-1}$—$X_N$—$X_2$ or $R_{N-1}$—$X_N$—OH are known to those skilled in the art and are commercially available or can be readily prepared from known starting materials by methods known in the literature. $X_2$ includes —Cl, —Br; it is preferred that $X_2$ is —Cl. It is preferred to use an isophthalic acid acylating agent of the formula $R_{N-2}R_{N-3}$N—CO-phenyl-CO— or a methylisophthalic acid acylating agent $R_{N-2}R_{N-3}$N—CO—($CH_3$—) phenyl-CO— where the substitution is 5-methyl-1,3-isophthalic acid. The more preferred 5-methyl-1,3-isophthalic acid is 3-[(N,N-dipropylamino)carbonyl]-5-methylbenzoic acid. These compounds are preferably prepared as set forth as follows. An ester, preferably the methyl ester of isophthalate or methyl 5-methyl-1,3-isophthalate is dissolved in a THF/DMF mixture. 1,1'-Carbonyldiimidazole is then added at 0–100 degrees. Next the desired amine (H—$NR_{N-2}R_{N-3}$) is added. After stirring at 0–100 degrees the reaction mixture is partitioned between a saturated aqueous solution with a pH of 3 to 9 and a water immiscible organic solvent. The aqueous layer is separated and extracted twice more with the organic solvent. The organic extracts are combined and then washed with an aqueous solution and dried. Filtration of the drying agent and removal of solvents by reduced pressure gives crude ester of the desired $R_{N-2}R_{N-3}$N—CO-phenyl-CO—O—$CH_3$ or a methylisophthalic acid acylating agent $R_{N-2}R_{N-3}$N—CO—($CH_3$—) phenyl-CO—O—$CH_3$. Purification of the ester can be achieved via chromatography on silica gel eluting with a suitable solvent The isophthalate ester or methylisophthalate ester of the mono-alkyl or di-alkyl amide is then treated with an aqueous solution of base such as alkali hydroxide in a minimum amount of THF/methanol/water and stirred at 20–70 degrees with monitoring. The solvents are removed under reduced pressure and subsequently partitioned between water and a water immiscible organic solvent. The aqueous phase is separated and extracted once more with a water immiscible organic solvent. The aqueous phase was then acidified to pH≦3. The mixture obtained is then extracted three times with ethyl acetate. These combined organic extracts are then dried. The drying agent is removed by filtration and the organic solvent remove under reduced pressure to gave crude product. The crude mono- or di-alkyl amide isophthalate/methylisophthalate is used as such in the next reaction with the amine (X) to produce the lactone (XI).

When it is desired to produce a primary amide, $R_{N-2}$ and $R_{N-3}$ are both —H, the following procedure is preferred. An ester of isophthalate or methyl 5-methyl-1,3-isophthalate is dissolved in a THF/DMF mixture. CDI is then added at 0–100 degrees. Ammonia gas is then bubbled into the mixture with monitoring. The reaction is cooled to 0° for the duration of the ammonia addition. The reaction is left stirring under a balloon of ammonia at 0–100° with monitoring. The reaction is partitioned between a aqueous solution with a pH of 3 to 9 and a water immiscible organic solvent. The phases are separated and the aqueous phase is extracted twice more with a water immiscible organic solvent. The organic extracts are washed with an aqueous solution and dried. Removal of solvents under reduced pressure gives crude ester of the desired $H_2N$—CO-phenyl-CO—O(Alkyl) or a methylisophalic acid acylating agent $H_2N$—CO—($CH_3$—) phenyl-CO—O(Alkyl). Purification of the crude ester can be achieved via chromatography on silica gel eluting with isopropanol/chloroform. The isophthalate ester or methylisophthalate ester of the primary amide is then treated with an aqueous solution of base such as alkali hydroxide in a minimum amount of THF/methanol/water and stirred at 0–100 degrees with monitoring. The solvents are removed under reduced pressure and subsequently partitioned between water and a water immiscible organic solvent. The aqueous phase is separated and extracted once more with a water immiscible organic solvent. The aqueous phase is then acidified until pH≦3. The mixture obtained is then extracted three times with a water immiscible organic solvent. These combined organic extracts are dried and the organic solvent removed under reduced pressure to gave crude product. The primary amide isophthalate/methylisophthalate is used as such in the next reaction with (X) to produce (XI).

When it is desired that the amine be cyclized to be a group such as morpholinyl, piperazinyl, piperidinyl and pyrrolidinyl, etc the following procedure is followed. An ester of isophthalate or methyl 5-methyl-1,3-isophthalate is dissolved in a suitable organic solvent and a catalytic amount or DMF is added. The mixture is cooled to −20 degrees to below room temperature and then oxalyl chloride is added. The mixture is stirred with monitoring and the solvents removed under reduced pressure. The acid chloride is left under vacuum overnight. The crude acid chloride is dissolved in a suitable organic solvent and cooled to −20 degrees to below rt before the addition of the cyclic amine and N-methyl piperidine. The reaction mixture is stirred at −20° to below rt with monitoring before the solvents are removed. The residue is diluted with water and water immiscible organic solvent and the phases are separated. The aqueous phase is extracted twice more with water immiscible organic solvent, and the combined organic extracts are washed with an aqueous solution and dried. Removal of solvents under reduced pressure gives the crude product. The crude cyclicamide is then treated with an aqueous base such as alkali hydroxide a minimum amount of THF/methanol/water and stirred overnight at 0–100°. The solvents are removed under reduced pressure and subsequently partitioned between water and a water immiscible organic solvent. The aqueous phase is extracted once more with a water immiscible organic solvent. Removal of water from the aqueous phase under reduced pressure gives the desired cyclic amide product.

The lactone (XI) may then be reacted with the appropriately substituted C-terminal amine, $R_C$—$NH_2$ by means known to those skilled in the art which opens the lactone to produce the desired hydroxyethylene end product (XII). The substituted C-terminal amines, $R_C$—$NH_2$ of this invention are commercially available or are known to those skilled in the art and can be readily prepared from known compounds. $R_C$ includes:

(I) $C_1$–$C_8$ alkyl unsubstituted or substituted with —OH, —O-phenyl, halo, or ($C_1$–$C_6$ alkoxy unsubstituted or substituted with halo), or (II) —C($R_{C-1}$)($R_{C-2}$)—CO—NH—$R_{C-3}$ where $R_{C-1}$ and $R_{C-2}$ are the same or different and are:
 (A) —H,
 (B) —$C_1$–$C_6$ alkyl,
 (C) —($C_1$–$C_4$ alkyl)—$R_{C'-aryl}$ where $R_{C'-aryl}$ is as defined for $R_{N-aryl}$,
 (D) —($C_1$–$C_4$ alkyl)—$R_{C-heteroaryl}$ where $R_{C-heteroaryl}$ is as defined for $R_{N-heteroaryl}$, and $R_{N-heteroaryl}$ is as defined above,
 (E) —($C_1$–$C_4$ alkyl)—$R_{C-heterocycle}$ where $R_{C-heterocycle}$ is as defined for $R_{N-heterocycle}$, and $R_{N-heterocycle}$ is as defined above,
 (F) —$R_{C-heteroaryl}$ where $R_{C-heteroaryl}$ is as defined above,
 (G) —$R_{C-heterocycle}$ where $R_{C-heterocycle}$ is as defined above,
 (H) —$(CH_2)_{1-4}$—OH,
 (I) —$(CH_2)_{1-4}$—$R_{C-4}$—$(CH_2)_{1-4}$-$R_{C-aryl}$ where $R_{C-4}$ is —O—, —S—, —NH—, or —$NR_{C-5}$— where $R_{C-5}$ is $C_1$–$C_6$ alkyl, and where $R_C$ aryl is as defined above,
 (J) —$(CH_2)_{1-4}$—$R_{C-4}$—$(CH_2)_{1-4}$—$R_{C-heteroaryl}$ where $R_{C-4}$ and $R_{C-heteroaryl}$ are as defined above, or
 (K) —$R_{C-aryl}$ where $R_{C'-aryl}$ is as defined above,
and where $R_{C-3}$ is:
 (A) —H,
 (B) —$C_1$–$C_6$ alkyl, substituted or unsubstituted with:
  (1) —H,
  (2) —$C_1$–$C_6$ alkyl,
  (3) —($C_1$–$C_4$ alkyl)—$R_{C'-aryl}$ where $R_{C'-aryl}$ is as defined for $R_{N-aryl}$,
  (4) —($C_1$–$C_4$ alkyl)—$R_{C-heteroaryl}$ where $R_{C-heteroaryl}$ is as defined for $R_{N-heteroaryl}$, and $R_{N-heteroaryl}$ is as defined above,
  (5) —($C_1$–$C_4$ alkyl)—$R_{C-heterocycle}$ where $R_{C-heterocycle}$ is as defined for $R_{N-heterocycle}$, and $R_{N-heterocycle}$ is as defined above,
  (6) —$R_{C-heteroaryl}$ where $R_{C-heteroaryl}$ is as defined above,
  (7) —$R_{C-heterocycle}$ where $R_{C-heterocycle}$ is as defined above,
  (8) —$(CH_2)_{1-4}$—OH,
  (9) —$(CH_2)_{1-4}$—$R_{C-4}$—$(CH_2)_{1-4}$—$R_{C'-aryl}$ where $R_{C-4}$ is —O—, —S—, —NH—, or —$NR_{C-5}$— where $R_{C-5}$ is $C_1$–$C_6$ alkyl, and where $R_{C'-aryl}$ is as defined above,
  (10) —$(CH_2)_{1-4}$-$R_{C-4}$—$(CH_2)_{1-4}$-$R_{C-heteroaryl}$ where $R_{C-4}$ and $R_{C-heteroaryl}$ are as defined above, or
  (11) —$R_{C-aryl}$ where $R_{C'-aryl}$ is as defined above,
  (12) —CO—OH and —NH—C (═O)—,
 (C) —$R_{C'-aryl}$ where $R_{C'-aryl}$ is as defined above,
 (D) —$R_{C-heteroaryl}$ where $R_{C-heteroaryl}$ is as defined above,
 (E) —$R_{C-heterocycle}$ where $R_{C-heterocycle}$ is as defined above,
 (F) —($C_1$–$C_4$ alkyl)—$R_{C-aryl}$ where $R_{C'-aryl}$ is as defined above,
 (G) —($C_1$–$C_4$ alkyl)—$R_{C-heteroaryl}$ where $R_{C-heteroaryl}$ is as defined above,
 (H) —($C_1$–$C_4$ alkyl)—$R_{C-heterocycle}$ where $R_{C-heterocycle}$ is as defined above, or
 (J) —C($R_{C-5}$)($R_{C-6}$)—CO—NH—C($R_{C-7}$)($R_{C-8}$)—COOH, where $R_{C-5}$, $R_{C-6}$, $R_{C-7}$, and $R_{C-8}$ are the same or different, and are as defined for $R_{C-1}$ and $R_{C-2}$ and where $R_{C-1}$ and $R_{C-2}$ are as defined above.

It is preferred that $R_C$ is:
(II) —C($R_{C-1}$)($R_{C-2}$)—CO—NH—$R_{C3}$ where $R_{C-1}$ and $R_{C-2}$ are the same or different and are:
 (A) —H,
 (B) —$C_1$–$C_6$ alkyl,
 (C) —($C_1$–$C_4$ alkyl)—$R_{C'-aryl}$ where $R_{C'-aryl}$ is as defined for $R_{N-aryl}$,
 (D) —($C_1$–$C_4$ alkyl)—$R_{C-heteroaryl}$ where $R_{C-heteroaryl}$ is as defined for $R_{N-heteroaryl}$, and $R_{N-heteroaryl}$ is as defined above,
 (E) —($C_1$–$C_4$ alkyl)—$R_{C-heterocycle}$ where $R_{C-heterocycle}$ is as defined for $R_{N-heterocycle}$, and $R_{N-heterocycle}$ is as defined above,
 (F) —$R_{C-heteroaryl}$ where $R_{C-heteroaryl}$ is as defined above,
 (G) —$R_{C-heterocycle}$ where $R_{C-heterocycle}$ is as defined above,
 (H) —$(CH_2)_{1-4}$—OH,
 (I) —$(CH_2)_{1-4}$—$R_{C-4}$'$(CH_2)_{1-4}$—$R_{C-aryl}$ where $R_{C4}$ is —O—, —S—, —NH—, or —$NR_{C-5}$— where $R_{C-5}$ is $C_1$–$C_6$ alkyl, and where $R_{C'-aryl}$ is as defined above,
 (J) —$(CH_2)_{1-4}$—$R_{C-4}$—$(CH_2)_{1-4}$—$R_{C-heteroaryl}$ where $R_{C-4}$ and $R_{C-heteroaryl}$ are as defined above, or
 (K) —$R_{C'-aryl}$ where $R_{C'-aryl}$ is as defined above,
and where $R_{C-3}$ is:
 (A) —H,
 (B) —$C_1$–$C_6$ alkyl,
 (C) —$R_{C-aryl}$ where $R_{C'-aryl}$ is as defined above,
 (D) —$R_{C-heteroaryl}$ where $R_{C-heteroaryl}$ is as defined above,
 (E) —$R_{C-heterocycle}$ where $R_{C-heterocycle}$ is as defined above,
 (F) —($C_1$–$C_4$ alkyl)—$R_{C-aryl}$ where $R_{C-aryl}$ is as defined above,
 (G) —($C_1$–$C_4$ alkyl)—$R_{C-heteroaryl}$ where $R_{C-heteroaryl}$ is as defined above,
 (H) —($C_1$–$C_4$ alkyl)—$R_{C-heterocycle}$ where $R_{C-heterocycle}$ is as defined above, or (J) —C(R$_{C-5}$)(R$_{C-6}$)—CO—NH—C(R$_{C-7}$)(R$_{C-8}$)—COOH, where R$_{C-5}$, R$_{C-6}$, R$_{C-7}$, and R$_{C-8}$ are the same or different, and are as defined for R$_{C-1}$ and R$_{C-2}$ and where R$_{C-1}$ and R$_{C-2}$ are as defined above.

In one embodiment, it is preferred that R$_{C-1}$ is —H, R$_{C-2}$ is —CH$_3$, and R$_{C-3}$ is —H. In this embodiment, R$_C$ has the structure:

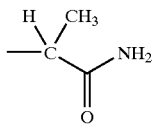

In another embodiment it is preferred that R$_C$—, is —H, R$_{C-2}$ is —CH$_3$, and R$_{C-3}$ is a substituted C$_2$ alkyl. It is more preferred that R$_{C-3}$ is a C$_2$ alkyl substituted with —COOH. It is most preferred that R$_C$ is:

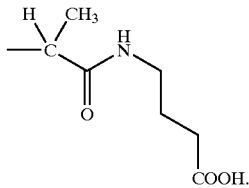

In another embodiment of the invention, R$_{C-3}$ is is —C(R$_{C-5}$)(R$_{C-6}$)—CO—NH—C(R$_{C-7}$)(R$_{C-8}$)—COOH, where R$_{C-5}$, R$_{C-6}$, R$_{C-7}$, and R$_{C-8}$ are the same or different, and are as defined for R$_{C-1}$ and R$_{C-2}$ and where R$_{C-1}$ and R$_{C-2}$ are as defined above. It is preferred that R$_{C-5}$ is —H, and R$_{C-6}$ is —CH$_2$CH$_2$CO$_2$H. It is more preferred that R$_{C-7}$ is —H and R$_{C-8}$ is —CH$_2$-phenyl.

It is most preferred that R$_C$ is:

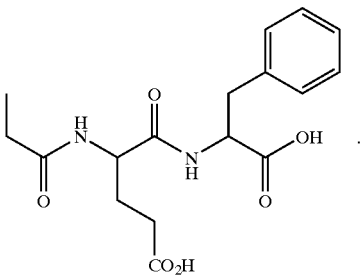

Suitable reaction conditions for opening the lactone (XI) to produce the desired hydroxyethylene end product (XII) include those of the AlMe$_3$-mediated coupling reaction disclosed in the literature procedure of S. F. Martin et al., *Tetrahedron Lett.* 1998, 39, 1517–1520. When the substituted C-terminal amine is a 1-amino-3,5-cis-dimethyl cyclohexyldicarboxylate it is preferrably prepared as follows. To dimethyl-5-isophthalate in acetic acid and methanol, is added rhodium in alumina in a high-pressure bottle. The bottle is saturated with hydrogen at 55 psi and shaken for one week of time. The mixture is then filtered through a thick layer of celite cake and rinsed with methanol three times, the solvents are removed under reduced pressure (with heat) to give a concentrate. The concentrate is triturated with ether and filtered again to give the desired C-terminal amine. When the substituted C-terminal amine is 1-amino-3,5-cis-dimethoxy cyclohexane it is preferably following the general procedure above and making non-critical variations but starting wth 3,5-dimethoxyaniline. When the substituted C-terminal amine is an aminomethyl group where the substituent on the methyl group is an aryl group, for example NH$_2$—CH$_2$—R$_{C-aryl}$, and NH$_2$—CH$_2$—R$_{C-aryl}$ is not commercially available it is preferably prepared as follows. A suitable starting material is the (appropriately substituted) aralkyl compound. The first step is bromination of the alkyl substitutent via methods known to those skilled in the art, see for example R. C. Larock in Comprehensive Organic Transformations, VCH Publishers, 1989, p. 313. Next the alkyl halide is reacted with azide to produce the aryl-(alkyl)-azide. Last the azide is reduced to the corresponding amine by hydrogen/catalyst to give the C-terminal amine of formula NH$_2$—CH$_2$—R$_{C-aryl}$.

CHART B, as defined within, sets forth a process for production of the amide (VII). Preparation of the amide (VIII) starts with the reaction of an appropriate aminoindanol (XIV) with an appropriate haloketone (XII) to afford the hydroxy indane (XV). The amino-indanol (XIV) and haloketone (XII) are well known to those skilled in the art or can be readily prepared from known compounds by methods well known to those skilled in the art. The X substituent of the haloketone is typically F, Cl, Br, or I. Preferably X is Cl. For the amino haloketone (XII), R$_2$ is:

(I) —H, (II) C$_1$–C$_6$ alkyl, or (III) —(CH$_2$)$_{0-4}$—R$_{2-1}$ where R$_{2-1}$ is (C$_3$–C$_6$)cycloalkyl, R$_{1-aryl}$ or R$_{1-heteroaryl}$ where R$_{1-aryl}$ and R$_{1-heteroaryl}$ are as defined above. It is preferred that R$_2$ is C$_1$–C$_6$ alkyl. It is more preferred that R$_2$ is C$_1$ alkyl. It is most preferred that R$_2$ is —CH$_3$.

The compounds of the invention may contain geometric or optical isomers as well as tautomers. Thus, the invention includes all tautomers and pure geometric isomers, such as the E and Z geometric isomers, as well as mixtures thereof. Furthermore, the invention includes pure enantiomers and diastereomers as well as mixtures thereof, including racemic mixtures. The individual geometric isomers, enantiomers, or diastereomers may be prepared or isolated by methods known in the art.

Compounds of the invention of designated stereochemistry may be included in mixtures, including racemic mixtures, with other enantiomers, diastereomers, geometric isomers or tautomers. Compounds of the invention with designated stereochemistry are typically present in these mixtures in excess of 50 percent. Preferably, compounds of the invention with designated stereochemistry are present in these mixtures in excess of 80 percent. Most preferably, compounds of the invention with designated stereochemistry are present in these mixtures in excess of 90 percent.

The compounds of formulas (XII), (XIII), and (XIV) are amines, and as such form salts when reacted with acids. Pharmaceutically acceptable salts are preferred over the corresponding amines of formulas (XII), (XIII), and (XIV) since they produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include acid addition salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dibydrogen phosphoric, phthalic, polygalactouronic, propionic, salicylic, stearic, succinic. succinic, sulfamic, sulfanilic, sulfonic, sulfuric, tannic, tartaric, teoclic and toluenesulfonic. For other acceptable salts, see *Int. J. Pharm.,* 33, 201–217 (1986) and *J. Pharm. Sci.,* 66(1), 1, (1977).

Preferred hydroxyethylene compounds of formulas (XII), (XIII), and (XIV), include, for example,

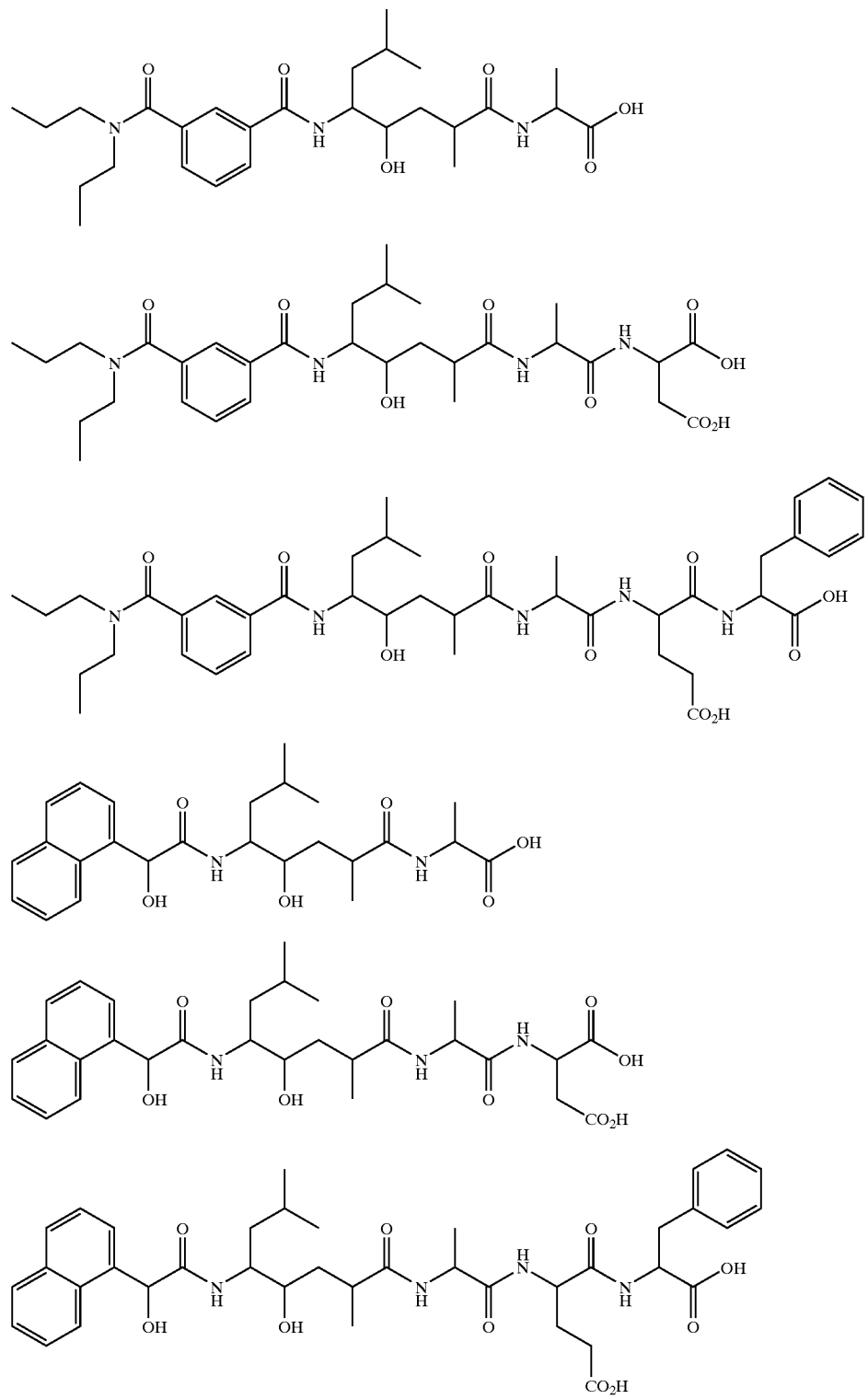

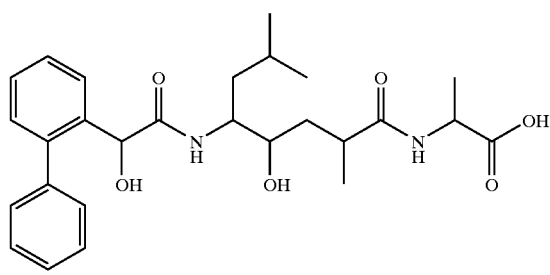
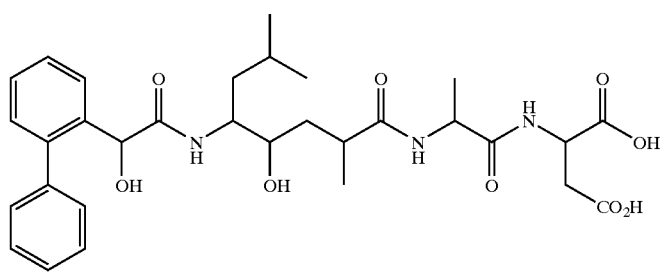
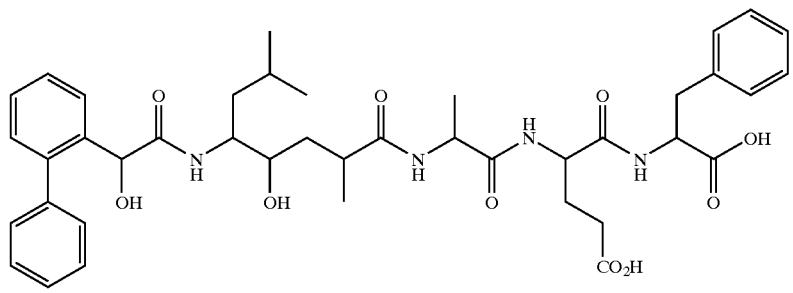
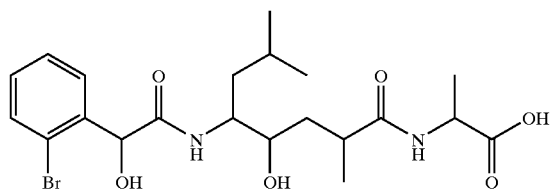
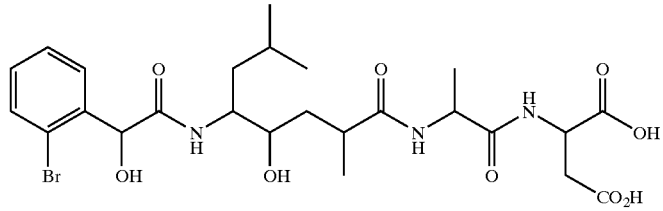
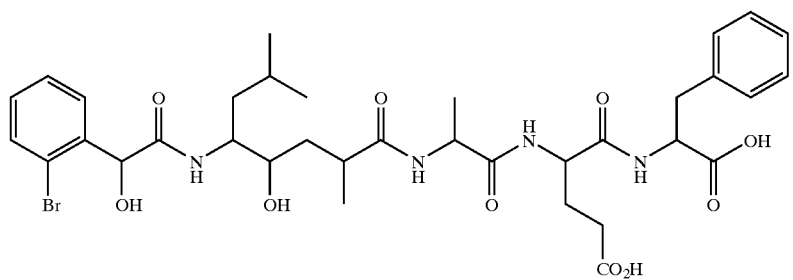

-continued

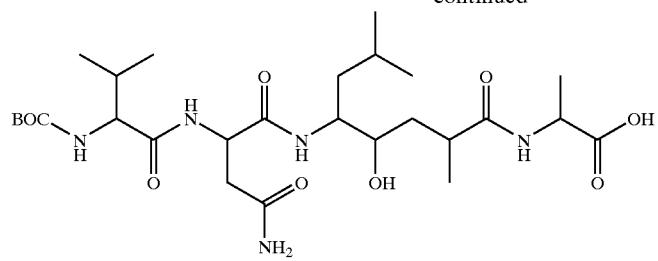

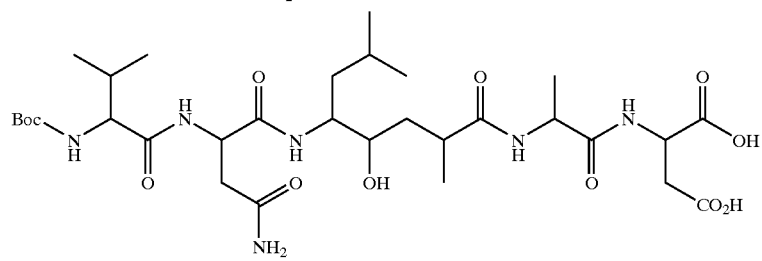

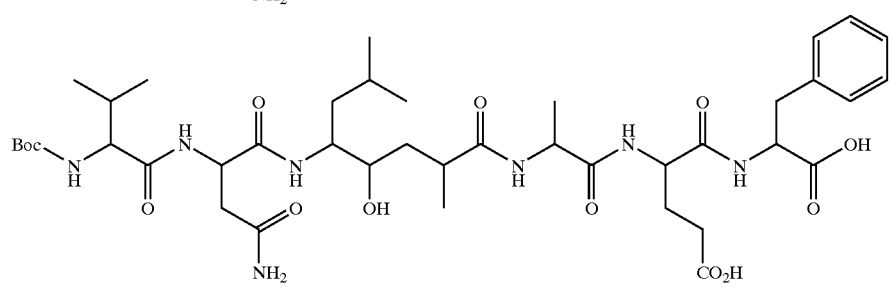

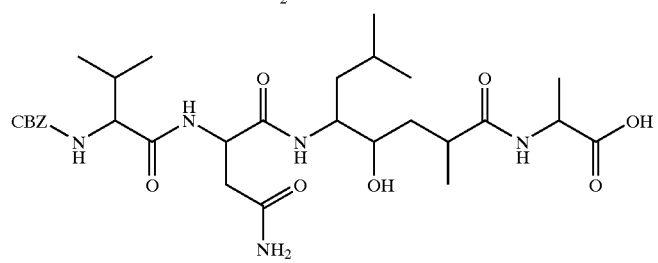

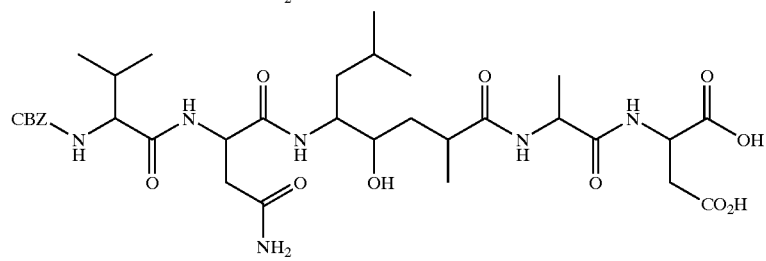

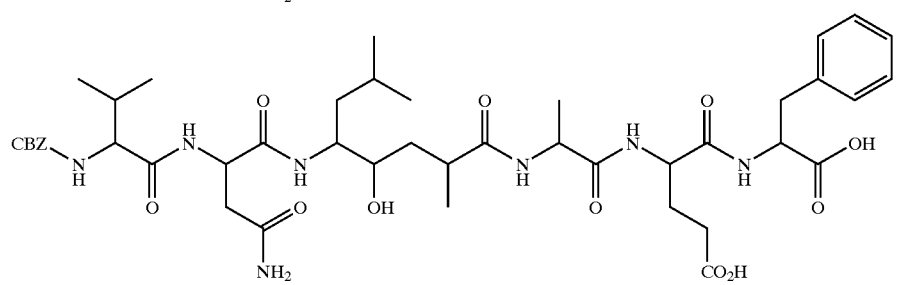

The hydroxyethylene compounds of formulas (XII), (XIII), and (XIV), and pharmaceutically acceptable salts thereof, are useful for treating humans suffering from Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type Alzheimer's disease. It is preferred the the disease is Alzheimer's disease.

When treating these diseases, the hydroxyethylene compounds of formulas (XII) (XIII), and (XIV) can either be used individually or in combination as is best for the patient.

With regard to these diseases the term "treating" means that the hydroxyethylene compounds of formulas (XII) (XIII), and (XIV) can be used in humans with existing disease. The hydroxyethylene compounds of formulas (XII) (XIII), and (XIV) will delay or slow the progression of the disease thereby giving the individual a more useful life span.

The term "preventing" means that if the compounds of the present invention are administered to those who do not now have the disease but who would normally get the disease or be at increased risk for the disease, they will not get the disease. In addition, "preventing" also includes delaying the development of the disease in an individual who will ultimately get the disease or would be at risk for the disease. By delaying the onset of the disease, the hydroxyethylene compounds of formulas (XII) (XIII), and (XIV) have prevented the individual from getting the disease during the period in which the individual would normally have gotten the disease or reduce the rate of development of the disease or some of its effects but for the administration of the hydroxyethylene compounds of formulas (XII) (XIII), and (XIV) up to the time the individual ultimately gets the disease. Preventing also includes administration of the compounds of the invention to those individuals thought to be predisposed to the disease due to familial history and/or due to the presence of one or more biological markers for the disease such as a known genetic mutation of APP or by analysis of APP cleavage products in body tissues or fluids.

In treating or preventing the above diseases the hydroxyethylene compounds of formulas (XII) (XIII), and (XIV) are administered in a therapeutically effective amount. The therapeutically effective amount will vary depending on the particular compound used and the route of administration as is known to those skilled in the art.

In treating a patient with any of the diagnosed above conditions a physician may administer hydroxyethylenes of formulas (XII) (XIII), and (XIV) immediately and continue indefinitely.

In treating patients who do not at the present have Alzheimer's disease but who are believed to be at substantial risk for Alzheimer's disease, the physician should start treatment when the patient first experiences early pre-Alzheimer's symptoms such as, memory or cognitive problems associated with aging. In addition, there are some patients who may be diagnosed with Alzheimer's through the detection of the genetic marker APOE4 or other biological indicators that are predictive for Alzheimer's disease. In these situations, even though the patient does not have symptoms of the disease, the administration of the hydroxyethylene compounds of formulas (XII) (XIII), and (XIV) may be started before they appear and treatment continued indefinitely to prevent or delay the outset of the disease.

The hydroxyethylene compounds of formulas (XII) (XIII), and (XIV) can be administered orally, parenterally (IV, IM, depo-IM, SQ and depo-SQ), sublingually, intranasally (inhalation), intrathecally, topically and rectally. The invention here is the novel hydroxyethylene compounds of formulas (XII) (XIII), and (XIV). Dosage forms known to those skilled in the art are suitable for delivery of the novel hydroxyethylene compounds of formulas (XII) (XIII), and (XIV).

Hydroxyethylene compounds of formulas (XII) (XIII), and (XIV) may be administered enterally or parenterally. When administered orally, hydroxyethylene compounds of formulas (XII) (XIII), and (XIV) can be administered in usual dosage forms for oral administration as is well known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the hydroxyethylene compounds of formulas (XII) (XIII), and (XIV) need to be administered only once or twice daily.

The oral dosage forms are administered to the patient 1, 2, 3, or 4 times daily. It is preferred that the hydroxyethylene compounds of formulas (XII) (XIII), and (XIV) be administered either three or fewer times, more preferably once or twice daily. Hence, it is preferred that the hydroxyethylene compounds of formulas (XII) (XIII), and (XIV) be administered in oral dosage form. It is preferred that whatever oral dosage form is used, that it be designed so as to protect the hydroxyethylene compounds of formulas (XII) (XIII), and (XIV) from the acidic environment of the stomach. Enteric coated tablets are well known to those skilled in the art. In addition, capsules filled with small spheres each coated to protect from the acidic stomach, are also well known to those skilled in the art. When administered orally the therapeutically effective amount is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started on one dose, that dose may have to be varied over time as the patient's condition changes.

Hydroxyethylene compounds of formulas (XII) (XIII), and (XIV) may also be advantageously delivered in a nano crystal dispersion formulation. Preparation of such formulations is described in U.S. Pat. No. 5,145,684. And nano crystalline dispersions of, for example, HIV protease inhibitors and their method of use are described in U.S. Pat. No. 6,045,829. The nano crystalline formulations typically afford greater bioavailability of drug compounds.

In addition, the hydroxyethylene compounds of formulas (XII) (XIII), and (XIV) can be administered parenterally. When administered parenterally they can be administered IV, IM, depo-IM, SC or depo-SC. When administered parenterally, the hydroxyethylene compounds of formulas (XII) (XIII), and (XIV) should deliver a therapeutically effective amount about 0.5 to about 100 mg/day, preferably from about 5 to about 50 mg daily. When a depo formulation is used for injection once a month or once every two weeks, the dose should be about 0.5 mg/day to about 50 mg/day or on a monthly amount the dose for one month should be from about 15 mg to about 1,500 mg. Because of the forgetfulness of the patients with Alzheimer's disease, it is preferred that the parenteral dosage form be a depo-IM injection.

The hydroxyethylene compounds of formulas (XII) (XIII), and (XIV) can be given sublingually. When given sublingually, the hydroxyethylene compounds of formulas (XII) (XIII), and (XIV) should be given one thru four times daily in the same amount as for IM administration.

The hydroxyethylene compounds of formulas (XII) (XIII), and (XIV) can be given intranasally. When given by this route of administration, the appropriate dosage forms are a nasal spray or dry powder as is known to those skilled in the art. The dosage of the hydroxyethylene compounds of formulas (XII) (XIII), and (XIV) for intranasal administration is the same as for IM administration.

The hydroxyethylene compounds of formulas (XII) (XIII), and (XIV) can be given intrathecally. When given by this route of administration the appropriate dosage form can be a parenteral dosage form as is known to those skilled in the art. The dosage of the hydroxyethylene compounds of formulas (XII) (XIII), and (XIV) for intrathecal administration is the same as for IM administration.

The hydroxyethylene compounds of formulas (XII) (XIII), and (XIV) can be given topically. When given by this route of administration, the appropriate dosage form is a cream, ointment or patch. Because of the amount of the hydroxyethylene compounds of formulas (XII) (XIII), and (XIV) needed to administered the patch is preferred. Further, two or more patches may be needed. When administered topically, the dosage is from about 0.5 mg/day to about 200 mg/day. However, the amount that can be delivered by a patch is limited. Therefore, two or more patches may be required. The number and size of the patch is not important, what is important is that a therapeutically effective amount of the hydroxyethylene compounds of formulas (XII) (XIII), and (XIV) be delivered as is known to those skilled in the art. The hydroxyethylene compounds of formulas (XII) (XIII), and (XIV) can be administered rectally by suppository as is known to those skilled in the art. When administered by suppository, the therapeutically effective amount is from about 0.5 mg to about 500 mg.

The hydroxyethylene compounds of formulas (XII) (XIII), and (XIV) can be administered by implants as is known to those skilled in the art. When administering a hydroxyethylene compound of formulas (XII) (XIII), and (XIV) by implant, the therapeutically effective amount is the same as for depot administration.

The invention includes a new method of using hydroxyethylene compounds of formulas (XII) (XIII), and (XIV) and hydroxyethylene compounds of formulas (XII) (XIII), and (XIV). Given a particular hydroxyethylene compound of formulas (XII) (XIII), and (XIV), and a desired dosage form, one skilled in the art would know how to prepare the appropriate dosage form for the hydroxyethylene compounds of formulas (XII) (XIII), and (XIV).

The hydroxyethylene compounds of formulas (XII) (XIII), and (XIV) are used in the same manner by the same routes of administration using the same pharmaceutical dosage forms and at the same dosing schedule for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease. The hydroxyethylene compounds of formulas (XII) (XIII), and (XIV) can be used with each other or with other agents used to treat or prevent the conditions listed above. Such agents include gamma-secretase inhibitors, anti-amyloid vaccines and pharmaceutical agents such as donepezil hydrochloride (ARICEPT™ Tablets), tacrine hydrochloride (COGNEX™ Capsules) or other acetylcholine esterase inhibitors and with direct or indirect neurotropic agents of the future.

Inhibition of APP Cleavage

The compounds of the invention inhibit cleavage of APP at the beta-secretase cleavage site, Met595-Asp596 for the APP695 isoform. While not wishing to be bound by a particular theory, inhibition of beta-secretase acitivity is thought to inhibit production of beta amyloid beta peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. No. 5,942,400.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-secretase

Various forms of beta-secretase (beta-secretase) enzyme are known, and are available and useful for assay of enzyme activity and inhibition of enzyme activity. These include native, recombinant, and synthetic forms of the enzyme. Human ASP2a and Asp2b has been characterized, for example, in published PCT patent applications WO98/22597 and WO00/17369, as well as synthetic forms of the enzyme.

The comounds of the invention inhibit 50% of the beta-secretase enzymatic acitivity at a concentration of from about 0.1 nM to about 200 TM, preferably at a concentration of from about 10 nM to about 100 TM, more preferably from about 100 nM to about 50 TM, and most preferably from about 1 TM to about 10 TM.

APP Substrate

Assays that demonstrate inhibition of beta-secretase-mediated cleavage of APP can utilize any of the known forms of APP, including the 695 amino acid "normal" isotype described by Kang et.al., 1987, Nature 325:733–6, the 770 amino acid isotype described by Kitaguchi et. al., 1981, Nature 331:530–532, and variants such as the Swedish Mutation (KM670–1NL) (APP-SW), the London Mutation (V7176F), and others. See, for example, U.S. Pat. No. 5,766,846 and also Hardy, 1992, *Nature Genet.* 1:233–234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400.

The APP substrate may also be a fusion peptide, formed of a peptide having the beta-secretase cleavage site fused to a peptide that confers a characteristic useful for enzymatic assay, for example, isolation and/or detection properties.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Cells expressing an APP substrate and an active beta-secretase can be incubated in the presence of a compound inhibitor to demonstrate inhibition of enzymatic activity as compared with a control. Activity of beta-secretase can be measured by analysis of one or more APP cleavage products. For example, cellular inhibition of beta-secretase activity would be expected to decrease release of the cleavage product, A beta.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immoassay (EIA or ELISA).

Primary neuronal cell cultures from human brain or from brain tissue obtained from transgenic animals expressing APP, particuly human APP, and capable of processing APP to detectable A beta are also useful cells for assay of beta-secretase cleavage activity. For example, primary human neuronal cell cultures derived from human embryonic tissues express endogenous beta-secretase and endogenous APP. Enzymatic activity is assayed in the presence of the inhibitory compound, and cleavage products, such as A beta, are measured. Another useful primary cell culture system employs cells derived from brain tissue of transgenic mice, for example, from PD-APP mice expressing a transgenic APP having a mutation at V717 or the Swedish mutation.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

Antibodies

Products characteristic of APP cleavage can be measured by immunoassay using various antibodies, as described, for example, in Pirttila et.al., 1999, *Neuro.Lett.* 249:21–4, and in U.S. Pat. No. 5,612,486. Useful antibodies to detect A beta include, for example, the monoclonal antibody 6E10 (Senetek, St. Louis, Mo.) that specifically recognizes an epitope on amino acids 1–16 of the A beta peptide; antibodies 162 and 164 (New York State Insititute for Basic Research, Staten Island, N.Y.) that are specific for hA beta 1–40 and 1–42, respectively. Another useful antibody is SW192, as discussed above, that recognizes an epitope uncovered on the C-termial cleavage fragment following APP-SW cleavage mediated by beta-secretase.

Animal Models

Animal models useful in testing the compounds of the invention include those expressing elevated levels of A beta, demonstrating an enhanced amount of A beta deposits, and/or increased number or size of beta amyloid plaques as compared with control animals. Such animal models include transgenic mammals. Suitable transgenic animals include rodents transformed with a variant or modified APP that results in a measured amount A beta in the animal that is greater than that produced in a non-transformed control. Examples of suitable transgenic animal models include a mouse transformed with APP-SW, described, for example, in U.S. Pat. Nos. 5,877,399, 5,612,486, and 5,850,003. Other suitable animals are transformed with V717 APP, as described, for example, in U.S. Pat. No. 5,877,015, and in Ganes et.al., 1995, *Nature* 373:523.

Cleavage of APP at the beta-secretase cleavage site can be analyzed in these animals by measure of cleavage fragments in the animal's brain tissues, and possibly cerebral fluids, as well as by analysis of beta amyloid plaques and assessment of necrosis in the animal's brain tissues.

On contacting an APP substrate with a beta-secretase enzyme in the presence of an inhibitory compound of the invention and under conditions sufficient to permit enzymatic mediated cleavage of APP and/or release of A beta from the substrate, the of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369 and U.S. Pat. No. 5,942,400. Such assays can be performed in cell-free incubations or in cellular incubations using cells expressing a beta-secretase and an APP substrate having a beta-secretase cleavage site.

An APP substrate containing the beta-secretase cleavage site of APP, for example, a complete APP or variant, an APP fragment, or a recombinant or synthetic APP substrate containing the amino acid sequence: KM-DA or NL-DA, is incubated in the presence of a beta-secretase enzyme, for example human (h) Asp2a, hAsp2b, a fragment thereof, or a synthetic or recombinant polypeptide variant of hAsp2a or hAsp2b having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nM–10 TM substrate, approximately 10–200 pM enzyme, and approximately 0.1 nM–10 TM inhibitor compound, in aqueous solution, at an approximate pH of 4–7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-enzyme used and its pH optimum, any additional enzymes and/or markers that might be used in the assay, and the like. Such optimization is routine and will not require undue experimentation.

Cellular Assays

Numerous cell-based assays to analyze beta-secretase activity and/or processing of APP to release A beta. In one embodiment, cells that naturally express beta-secretase are used. Alternatively, cells are modified to express a recombinant beta-secretase, for example, hAsp2a, hAsp2b, or a recombinant or synthetic variant enzyme as discussed above.

The APP substrate may be added to the culture medium or expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Contact of an APP substrate with a beta-secretase enzyme within the cell and in the presence or absence of a compound inhibitor of the invention can be used to demonstrate the inhibitory activity. Beta-secretase activity or function, for example, as measured by cleavage of the APP substrate and detection of fragments and/or markers, can take numerous forms, as discussed above for non-cellular assays. Preferably, assay in the presence of a useful inhibitory compound provides at least about 30%, most preferably at least about 50% inhibition of the enzymatic activity, as compared with a non-inhibited control.

In such assays, for example, the cells expressing APP and beta-secretase are incubated in a culture medium under conditions to permit processing of the APP by the enzyme and release of A beta into the medium and accumulation of other fragments of APP in cell lysates. The inhibitory activity of the compounds of the invention can be demonstrated by incubating the cells in the presence and absence of the compound. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells, where the transgene is APP, and other cells such as those of a stable 293 cell line expressing APP, for example, APP-SW. In the cellular assay, cells are incubated in the presence or absence of the inhbitor, under conditions suitable for beta-secretase enzymatic activity at it's cleavage site on the APP substrate. Cell supernatant is harvested, and analyzed for cleavage fragments, for example using immunoassay.

In Vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the comounds of the invention. Preferred are animals that exhibit characteristics associated with the pathophysiology of AD. Certain transgenic animal models for AD have been described, for example, in U.S. Pat. Nos. 5,877,399, 5,612,486, 5,387,742, 5,720,936, and 5,811,633.

Administration of the compound inhibitors of the invention to the transgenic mice described herein provides an alternative method for demonstrating the inhibitory activity of the compound inhibitors. Administration of the compound inhibitor in a pharmaceutly effective carrier and via an administrative route that reaches the target tissue in an appropriate therapeutic amount is preferred. Inhibition of beta-secretase-mediated cleavage of APP and of A beta release can be measured by analysis of the cleavage products in the body fluids or tissues of the animal. Analysis of brain tissues for A beta deposits or plaques is also made.

It should be apparent to one skilled in the art that the exact dosage and frequency of administration will depend on the particular hydroxyethylene compounds of formulas (XII) (XIII), and (XIV) administered, the particular condition being treated, the severity of the condition being treated, the age, weight, general physical condition of the particular patient, and other medication the individual may be taking as is well known to administering physicians who are skilled in this art.

Definitions and Conventions

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$," where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)$ $(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-I-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents $\alpha$—$R_{i-j}$ and $\beta$—$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —C($\alpha$-$R_{i-j}$)($\beta$-$R_{i-k}$)—. For example, when the bivalent variable $R_6$, —C(=$R_6$)— is defined to consist of two monovalent variable substituents, the two monovalent variable substituents are $\alpha$-$R_{6-1}$:$\beta$-$R_{6-2}$, . . . $\alpha$-$R_{6-9}$:$\beta$-$R_{6-10}$, etc, giving —C($\alpha$-$R_{6-1}$)($\beta$-$R_{6-2}$)—, . . . —C($\alpha$-$R_{6-9}$)($\beta$-$R_{6-10}$)—, etc. Likewise, for the bivalent variable $R_{11}$, —C(=$R_{11}$)—, two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O—CO— . . . " means a lactone in which the carbonyl is bonded to $C_2$. However, when designated " . . . $R_j$ and $R_i$ are taken together to form —CO—O—$CH_2$—$CH_2$-the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—($CH_2$)$_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$) alkoxy ($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

It is to be understood that the recitation of numerical ranges by endpoints includes all numbers and fractions subsumed within that range (e.g. 1 to 5 includes 1, 1.5, 2, 2.75, 3, 3.80, 4, and 5).

It is to be understood that a substituent or a group can be attached to another atom or group of atoms by any member of the substituent, unless designated otherwise.

It is to be understood that all numbers and fractions thereof are presumed to be modified by the term "about."

It is to be understood that "a" as used herein includes both the singular and plural.

The general definitions used herein have the following meanings within the scope of the present invention.

II. Definitions

All temperatures are in degrees Celsius.

TLC refers to thin-layer chromatography.

psi refers to pounds/in$^2$.

HPLC refers to high pressure liquid chromatography.

THF refers to tetrahydrofuran.

DMF refers to dimethylformamide.

EDC refers to ethyl-1-(3-dimethylaminopropyl) carbodiimide or 1-(3-dimethylaminopropyl)-3-ethylcarbodiimide hydrochloride.

NBS refers to N-bromosuccinimide.

TEA refers to triethylamine.

BOC refers to 1,1-dimethylethoxy carbonyl or t-butoxycarbonyl, —CO—O—C(CH$_3$)$_3$.

CBZ refers to benzyloxycarbonyl, —CO—O—CH$_2$—φ

TFA refers to trifluoracetic acid, CF$_3$—COOH.

CDI refers to 1,1'-carbonyldiimidazole.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (d) downfield from TMS.

–φ refers to phenyl (C$_6$H$_5$).

MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.

HRMS refers to high resolution mass spectrometry.

Ether refers to diethyl ether.

"APP", amyloid precursor protein, is defined as any APP polypeptide, including APP variants, mutations, and isoforms, for example as disclosed in U.S. Pat. No. 5,766,846.

"A beta", beta amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

"beta-secretase" is an aspartyl protease that mediates cleavage of APP at the amino-terminal edge of A beta. Human beta-secretase is described, for example, in WO00/17369.

A compound of the invention is any compound described herein having inhibitory activity against a beta-secretase enzyme; against the production of A beta; against the production of beta amyloid deposits or plaques; or against the development or progression of neurodegenerative disease such as AD, measured, for example, by one or more of the assays described herein.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

BOP refers to benzotriazol-1-yloxy-tris(dimethylamino) phosphonium hexafluorophosphate.

TBDMSCl refers to t-butyldimethylsilyl chloride.

TBDMSOTf refers to t-butyldimethylsilyl trifluosulfonic acid ester.

Trisomy 21 refers to Down's Syndrome.

Ac=acetyl (methylcarbonyl)

aq.=aqueous bd=broad doublet bs=broad singlet c=concentration (g/mL)

cc=cubic centimeter d=doublet

DCM=dichloromethane=methylene chloride=CH$_2$Cl$_2$ de=diastereomeric excess

EDTA=ethylene diamine tetraacetic acid eq.=equivalents

EtOAc=ethyl acetate

EtOH=ethanol g=grams

HOBT=1-hydroxybenzotriazole h=hour

IC$_{50}$=inhibitory concentration of a compound that reduces enzyme activity by half.

iso=an alkyl chain having the ending group 2-methylpropyl, i.e. —CH(CH$_3$)$_2$.

IM=intramuscularly

IV=intravenously

SC=subcutaneously

L=liter

LDA=lithium diisopropyl amide m=multiplet max=maximum mg=milligram mL=milliliter mm=millimeter mM=millimolar mmol=millimole mp=melting point MeOH=methanol meq=milliequivalent MsOH=methanesulfonic acid n=normal, i.e. unbranched, e.g. n-Pr is —CH$_2$—CH$_2$—CH$_3$ N=normal ng=nanogram nm=nanometers OD=optical density PEPC=1-(3-(1-pyrrolidinyl)propyl)-3-ethylcarbodiimide pg=picogram pM=picoMolar Rf=ratio of movement of a substance on a thin layer chromatogram in comparison to the movement of the solvent front.

δ=units of measurement in nuclear magnetic resonance spectroscopy which are relative to a standard, e.g. tetramethyl silane.

q=quartet quint.=quintet rpm=rotations per minute s=singlet t=triplet t or tert=tertiary in an alkyl chain, e.g. t-butyl is —C(CH$_3$)$_3$.

μL=microliter

μM=micromolar (an expression of concentration in micromoles/liter)

s=singlet t=triplet

UV=ultraviolet

Unless otherwise indicated, all functional group radicals (e.g., alkyl, aryl, cycloalkyl, cyclic heteroaryl, heterocycle, etc.) can be substituted or unsubstituted. Substituted functional group radicals can be substituted with one or more substituents, unless indicated otherwise. Suitable substituents for substituted functional group radicals generally include halogen, hydroxy, alkoxy, alkyl, aryl, arylalkyl, alkylaryl, arylalkoxy, and the like. It will be understood that the terminology "X radical substituted by a/an Y" includes the "X" radical being substituted by two or more "Y", unless indicated otherwise.

"Alkyl" refers to linear or branched, saturated aliphatic hydrocarbon radicals, such as, for example, methyl, ethyl, propyl, butyl, octyl, isopropyl, tert-butyl, sec-pentyl, and the like.

"Cycloalkyl" refers to cyclic aliphatic hydrocarbon radicals, such as, for example, 3- to 8-member hydrocarbon rings (e.g., cyclohexyl or cyclopentyl), bicyclic 4- to 10-member hydrocarbon ring systems, and a tricyclic 8- to 14-member hydrocarbon ring systems. Monocyclic cycloalkyl groups include, for example, cyclohexane and cyclopentane. Multicyclic cycloalkyl groups include cyclohexyl, cyclopentyl, and 1,2,3,4-tetrahydrohaphthyl for example.

"Heterocycle" refers to cyclic, non-aromatic radicals containing at least two carbon atoms and 1 to 3 heteroatoms selected from O, N, and S as members of at least one ring. Examples of such radicals include 3- to 8-member rings; bicyclic 4- to 10-member ring systems, and tricyclic 8- to 14-member ring systems, where at least one ring (and in some instances each of the rings) of any of these examples contains 1 to 3 heteroatoms selected from O, N, and S as members of the ring. Monocyclic heterocyclic groups include morpholinyl, piperazinyl, and tetrahydrofuranyl, for example. Multicyclic heterocyclic groups include decahydroquinoline, cyclohexene oxide, and 3-amino-3-azabicyclo [3.3.0] octane, for example.

"Alkylene' refers to bivalent, linear or branched, saturated aliphatic hydrocarbon radicals, such as, for example, methylene, ethylene, propylene, butylene, octylene, isopropylene, tert-butylene, sec-pentylene, and the like.

"Alkenyl" refers to linear or branched aliphatic hydrocarbon radicals containing at least one double bond, such as, for example, ethenyl, 1-propenyl, 2-propenyl, 1-butenyl, 2-methyl-1-propenyl, and the like.

"Alkynyl" refers to linear or branched aliphatic hydrocarbon radicals containing at least one triple bond, such as, for example, ethynyl (acetyl), 1-propynyl, 2-propynyl, 1-butynyl, and the like.

"Aryl" refers to cyclic aromatic hydrocarbon radicals having a single ring, such as phenyl, multiple rings, such as biphenyl, and multiple condensed rings, such as naphthyl and anthryl. Monocyclic aryl groups include phenyl, for example. Multicyclic aryl groups include naphthyl and anthryl, for example.

"Amine" includes primary, secondary and tertiary amines which may be in straight or branched chains or, in the case of secondary and tertiary amines within rings (e.g. morpholine and piperazine).

"Heteroaryl" refers to a cyclic aromatic rings having 1 to 4 hetero atoms selected from S, O, and N; and aromatic 7 to 10 membered organic stable bicyclic rings having 1 to 5 hetero atoms selected from S, O, and N. Examples of such radicals include 3- to 8-member rings; bicyclic 4- to 10-member ring systems; and tricyclic 8- to 14-member ring systems, where at least one ring (and in some instances each of the rings) of any of these examples contains 1 to 3 heteroatoms selected from O, N, and S as members of the ring.

"Acyloxy" refers to the groups R—C(O)O—, substituted R—C(O)O—, cycloalkyl-C(O)O—, aryl-C(O)O—, and heterocyclic-C(O)O where R=alkyl, and alkyl, cycloalkyl, aryl, and heterocyclic are as defined herein.

"Acylamino" refers to the groups R—C(O)N—, substituted R—C(O)N—, cycloalkyl-C(O)N—, aryl-C(O)N—, and heterocyclic-C(O)N— where R=alkyl, and alkyl, cycloalkyl, aryl, and heterocyclic are as defined herein.

"Amide" and "amido" refer to a functional group containing a carbon atom double-bonded to an oxygen atom and additionally singly bonded to a nitrogen atom [—C(O)—N]. "Primary" amide describes an unsubstituted amide group [—C(O)—NH$_2$]. "Secondary" and "tertiary" amides are amides in which nitrogen is substituted with one and two non-hydrogen groups respectively. The term "lactam" refers to a cyclized amide, i.e. a secondary or tertiary amide wherein the carbonyl carbon and the nitrogen atom are adjacent members of a ring.

"Halogen" refers to fluoro, chloro, bromo, and iodo radicals.

"Lactone" refers to cyclized ester of a carboxylic acid.

"Thio" refers to the replacement of oxygen by sulfur in a defined radical. Examples of thio compound include alkylthioxy compounds (e.g. alkyl-S—).

"Thioxyalkyl" refers to the divalent radical —S-alkyl-, where alkyl is as defined above. Examples of thioxyalkyl moietites include alkyl-S-alkyl moieties, such as CH$_3$—S—CH$_2$CH$_2$—.

"Alkoxy" refers to the radical —O-alkyl with alkyl as defined above. Alkoxy groups include, for example, methoxy, ethoxy, propoxy, isopropoxy, and the like.

"Arylalkyl" and "aralkyl" refer to an alkyl radical substituted with an aryl.

"Alkylaryl" refers to an aryl radical substituted with an alkyl.

All the terms "carboxyl", "carboxylic acid", "carboxylate" and "carbamoyl" are terms referring to functional groups containing a carbon atom double-bonded to an oxygen atom [C=O, also called an acyl or a carbonyl group, represented in linear notation as —C(O)—] and additionally single- bonded to another oxygen atom [—C(O)—O—], and in the case of carbamoyl, additionally a nitrogen atom is also bonded to the carbonyl carbon to give —N—C(O)—O—. Carboxyl, carboxylate and carbamate include the corresponding pharmaceutically acceptable $C_1$-$C_6$ alkyl and $C_6$-$C_{10}$ aryl esters and secondary and tertiary amides.

Combinations of these terms for functional group radicals are also used. Typically, the last term in the designation contains the radical that bonds to the remainder of the chemical structure. For example, "haloalkyl" refers to an alkyl radical substituted by a halogen, "cycloalkylalkyl" refers to alkyl radical substituted by a cycloalkyl, and "alkylcycloalkyl" refers to a cycloalkyl radical substituted by an alkyl.

Chart A

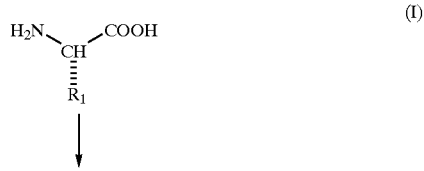

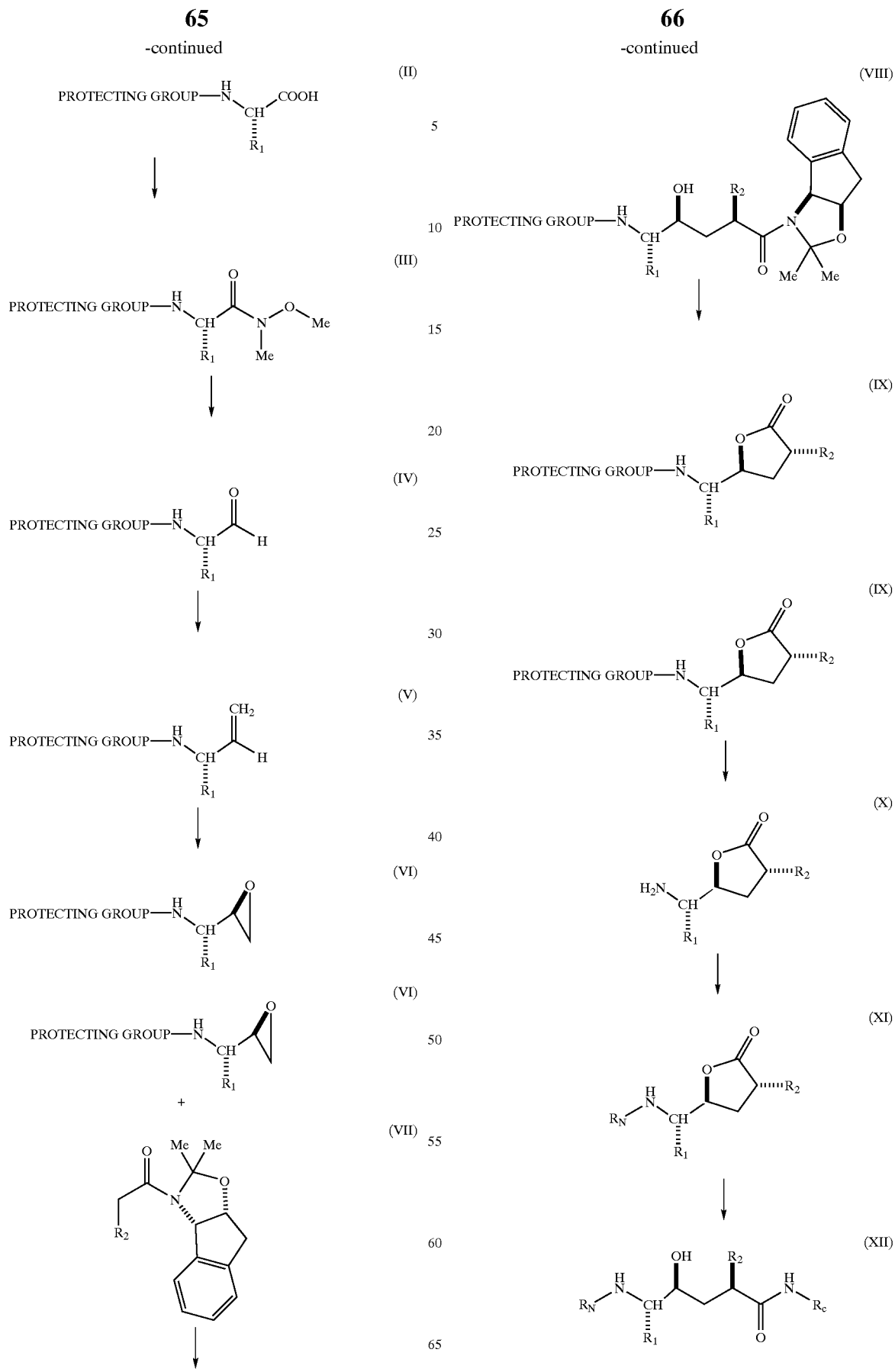

-continued
Chart B

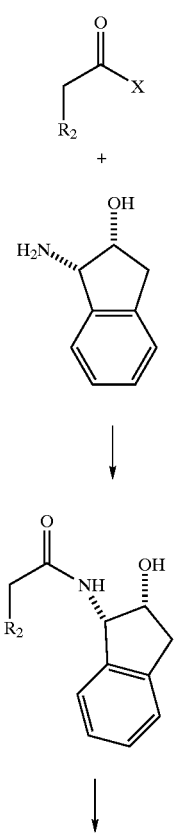

(XIII)

(XIV)

(XV)

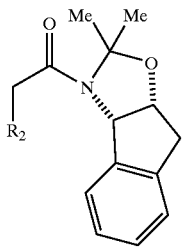

(VII)

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparations of the novel compounds of the present invention utilizing the hydroxyethylene isostere are illustrated in the following examples, which are not, however, intended to be any limitation thereof.

Methods of Synthesis

The following reaction schemes illustrate methods of construction of the hydroxyethylene dipeptide isosteres provided in examples 1–13. Variations of starting materials may be used in these reactions to prepare hydroxyethylene cores having other side chain groups. Substitutions of available starting materials to achieve the desired side chain variants will be apparent to one of ordinary skill in the art.

Scheme I

Synthesis of a protected hydroxyethylene moiety suitable for C-terminal coupling

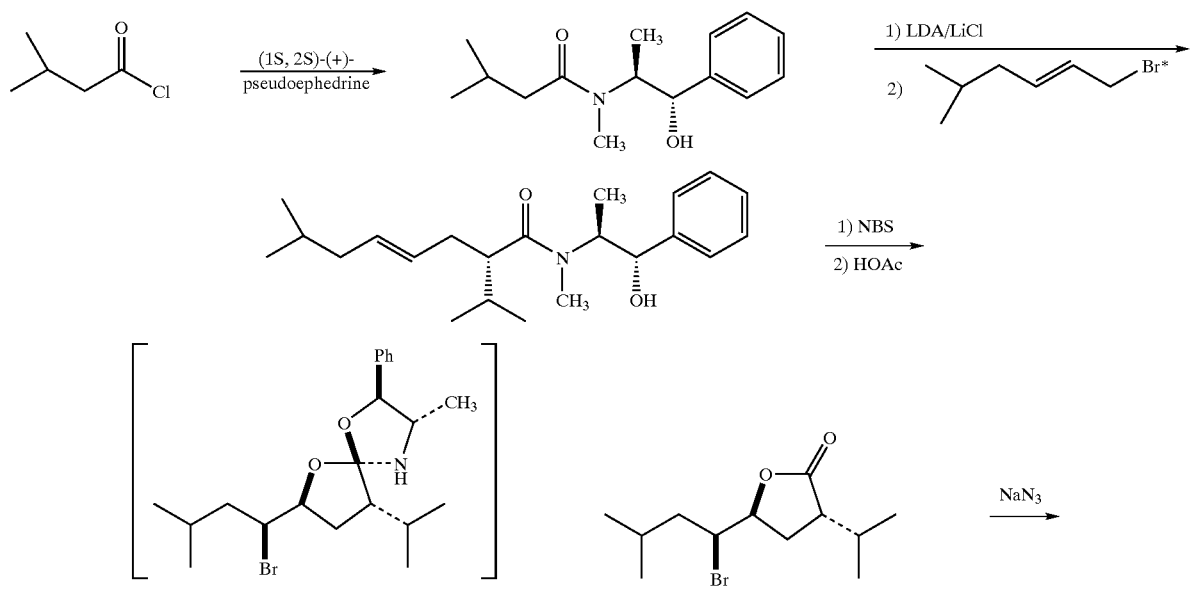

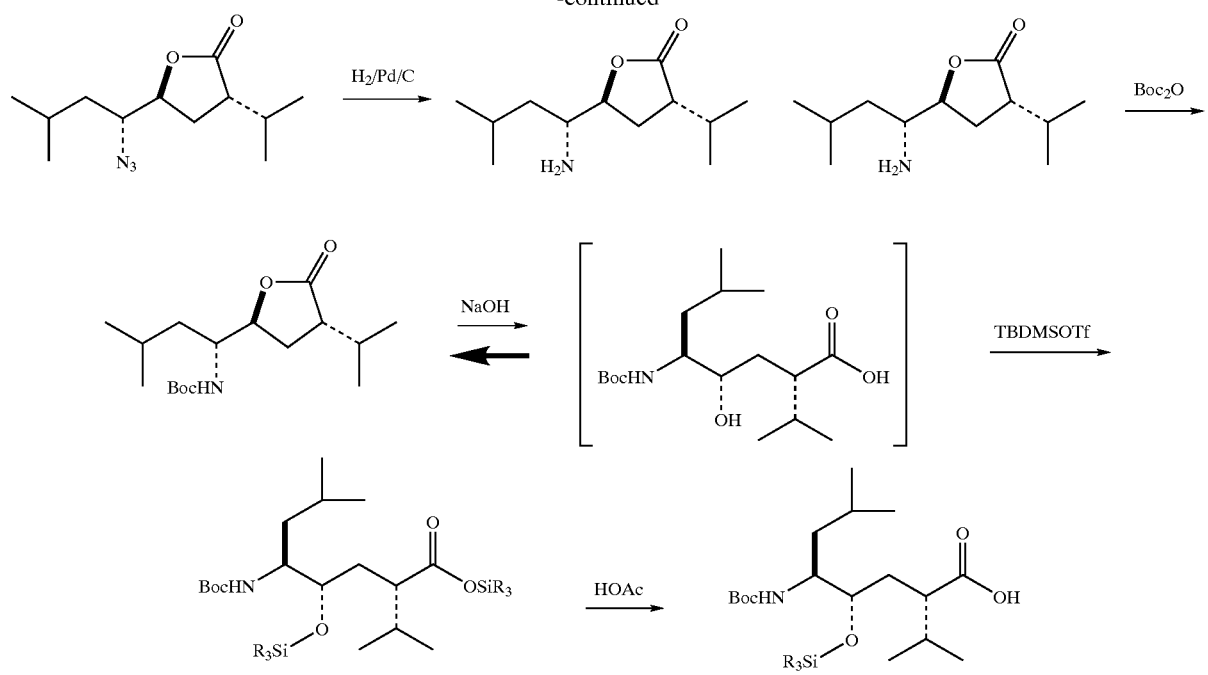

*Procedure for preparation of 1-bromo-5-methylhex-2-ene:

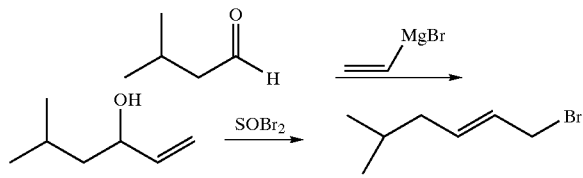

Alternatively hydroxyethylenes may be prepared by the method described below. Synthesis of the Boc-3,5-difluorophenylalanine threo epoxide starting material was adapted from the procedure of Luly, J R, et al. *J. Org. Chem.* 1987, 52, 1487–1492 for the synthesis of Boc-phenylalanine threo epoxide (Scheme II). The starting material utilized in the preparation of Boc-3,5-difluorophenylalanine threo epoxide was Boc protected 1-3,5-difluorophenylalanine available from Synthetech, Inc. (1290 Industrial Way, P. O. Box 646, Albany, Oreg. 97321 USA).

Scheme II

Formation of a representative chiral epoxide precursor

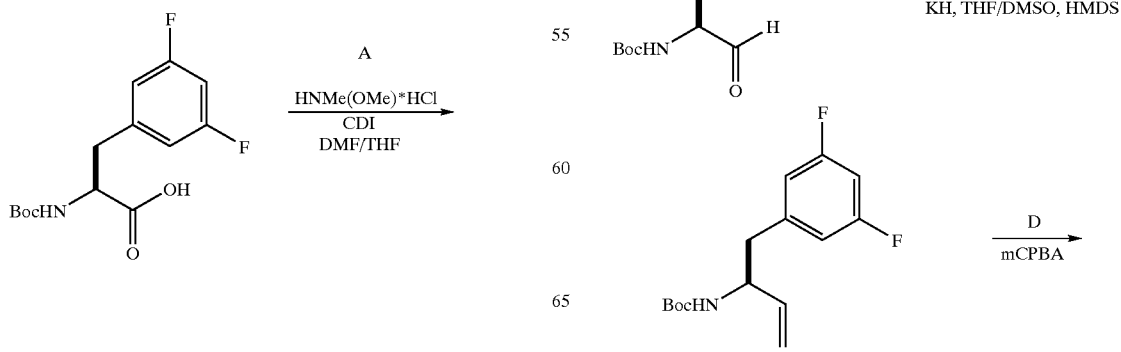

-continued

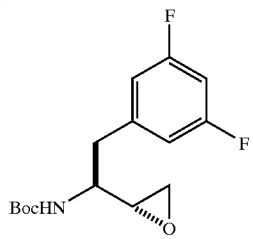

The chiral amine synthesis, the initial alkylation step and further manipulation to the lactone were accomplished based on literature procedures as follows: Dragovich, P S, et al. *J. Med. Chem.* 1999, 42, 1203–1222; Askin, D., et al. *J. Org. Chem.* 1992, 57, 2771–2773. Cleavage of the Boc protecting group and subsequent coupling of the acid was accomplished using the procedures for deprotection of the amine and EDC coupling given below. Ring-opening of the lactone to the final product was accomplished using a AlMe$_3$-mediated coupling step according to the literature procedure of S. F. Martin et al., *Tetrahedron Lett.* 1998, 39,1517–1520. Removal of a Boc-Protecting Group From a Protected Amine to Generate Free Amine:

For example, the Boc-protected alpha-amino lactone intermediate of either Scheme I or II was dissolved in a trifluoroacetic acid/dichloromethane (1/1) solution. The reaction was monitored by TLC to confirm the consumption of starting material at which time the solvents were removed under reduced pressure to yield the free amine, which was used without further purification.

Coupling Deprotected Amine with a Selected N-Terminal Capping Group:

For example, 2-(N,N-dipropyl) amidobenzoic acid (1.0 equiv.) was dissolved in 30 mL of dry dichloromethane, then HOBT (2.0 equiv.), functionalized alpha-amino lactone from the step above (1.0 equiv.) and TEA (5 equiv.) were added and all was stirred for 20 minutes. EDC (1.2 equiv.) was added and the mixture was stirred overnight under an atmosphere of nitrogen. The reaction was then diluted with water and extracted with EtOAc (3×). The organic layers were washed with aqueous citric acid (2×), sat. NaHCO$_3$ (2×), brine, then dried over MgSO$_4$, and the solvent was removed under vacuum. The product of this step may then be subjected to a lactone ring aminolysis to provide the desired amide bond.

TABLE 1

Enzyme inhibition assay results for structures having the peptide backbone:

(XII)

| Example | R$_N$ | R$_C$ |
|---|---|---|
| Examples 1–6: R2 = —CH(CH$_3$)$_2$ and R1 = —CH$_2$CH(CH$_3$)$_2$ | | |
| 1 | | |
| 2 | Boc-Val-Met- | |
| 3 | | |

TABLE 1-continued
Enzyme inhibition assay results for structures having the peptide backbone:
(XII)
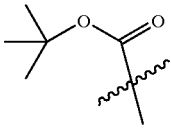
| Example | $R_N$ | $R_C$ |
|---|---|---|
| 4 | 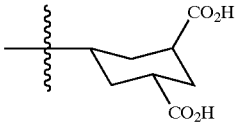 | 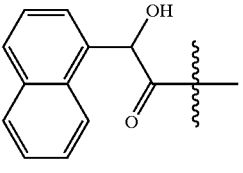 |
| 5 | 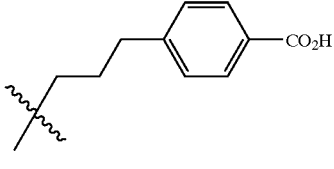 | 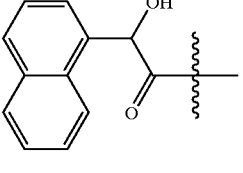 |
| 6 | 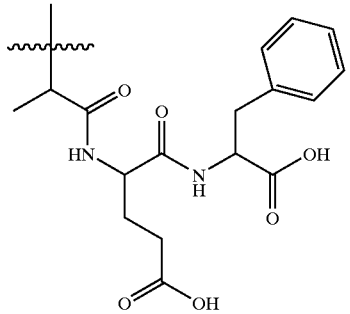 | 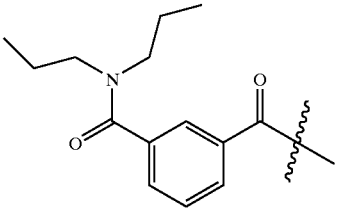 |
*Assay procedure described in the Example 70
Examples 7–10: R2 = —CH$_2$CH$_3$ and R1 = —CH$_2$-3,5-difluorophenyl
| | | |
|---|---|---|
| 7 | 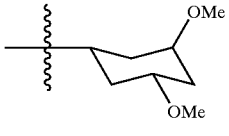 | 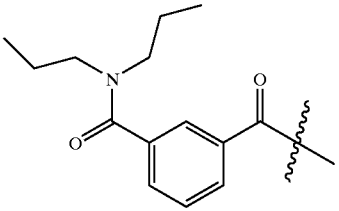 |
| 8 | 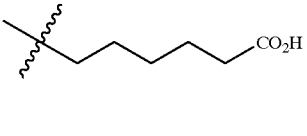 | |

TABLE 1-continued
Enzyme inhibition assay results for structures having the peptide backbone:
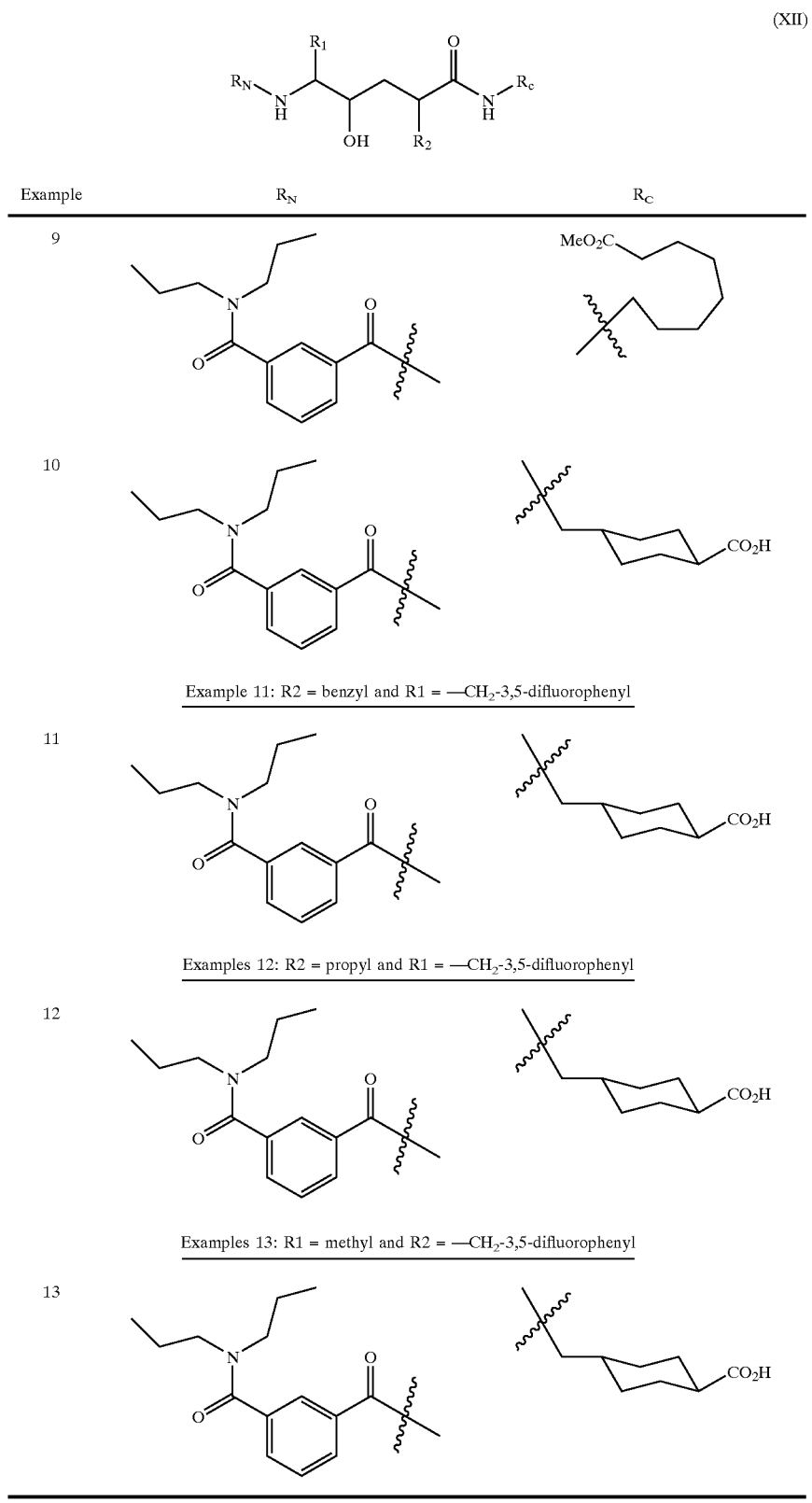
(XII)

Example 1

This compound was prepared employing the amino and hydroxy protected hydroxyethylene prepared via Scheme I. The compound was prepared standard resin supported peptide synthetic methods using standard HOBt, EDC coupling procedures described under Scheme II. Boc-Phe was esterified to the resin support. The Boc protecting group was removed from the Phe by treatment with trifluoroacetic acid in dicloromethane (TFA/DCM) and then coupled with Boc-Glu (mono ester) as described above. The cycle of amino deprotection and HOBt/EDC coupling was repeated with Boc-Ala, then with the protected hydroxyethylene moiety of Scheme I and then Boc-Met and finally Ac-Val. The glutamyl ester was removed via LiOH hydrolysis. The silyl group was removed from the hydroxyl function by treatment with tetra-t-butylammonium fluoride [(t-Bu)$_4$NF] in THF.

| | |
|---|---|
| Molecular Formula | $C_{41}H_{68}N_6O_9S$ |
| Molecular Weight | 821.10 |
| Mass spec (MH+) | 821 |

Example 2 p-Aminomethylbenzoic acid methyl ester (commercially available) was coupled with the hydroxyethylene moiety of Scheme I using standard EDC/HOBt coupling. The Boc protecting group was removed from the N-terminal and then subsequently coupled with Boc-Val-Met. The methyl ester was hydroylzed as described above and silyl group was removed from the hydroxyl function by treatment with tetra-t-butylammonium fluoride [(t-Bu)$_4$NF] in THF.

| | |
|---|---|
| Molecular Formula | $C_{35}H_{58}N_4O_8S$ |
| Molecular Weight | 694.927 |
| tlc Rf (solvent) | Rf = 0.28 in 5% Methanol/dichloromethane |
| Purification: | 5% Methanol/dichloromethane |
| Mass spec (MH+) | 695 |

Example 3

The hydroxyethylene moiety of Scheme I was coupled with the dimethyl ester of 3,5-dicarboxycyclohexylamine as prepared in Scheme VI A. This intermediate was in turn deprotected at the N-terminal with TFA/DCM and then coupled with the alpha-hydroxy-naphthylacetic acid. The methyl esters were hydrolyzed with LiOH and then the silyl group was removed from the hydroxyl function by treatment with tetra-t-butylammonium fluoride [(t-Bu)$_4$NF] in THF.

| | |
|---|---|
| Molecular Weight | 584.7 |
| tlc Rf (solvent) | 0.15 (10% MeOH/CH2Cl2) |
| Purification: | Flash chromatography |
| Mass spec (M + H+) | (CI) 584.7 |

Example 4

The protected hydroxyethylene as produced in Scheme I was coupled with the the dimethyl ester of 3,5-dicarboxycyclohexylamine (Scheme VI A). The diester was hydrolyzed with LiOH and the silyl protecting group removed by treatment with tetra-t-butylammonium fluoride [(t-Bu)$_4$NF] in THF.

| | |
|---|---|
| Molecular Formula | $C_{25}H_{44}N_2O_8$ |
| Molecular Weight | 500.6 |
| tlc Rf (solvent) | 0.15 (5% MeOH/CH$_2$Cl$_2$) |
| Purification: | Acid/base extraction |
| Mass spec (M − H+) | (CI) 498.7 |

Example 5

(Diastereomeric at the Alpha-hydroxy-naphthylacetyl)

The hydroxyethylene moiety of Scheme I was coupled with the methyl 3-(1-aminopropyl)-4-benzoate (commercially available). This intermediate was in turn deprotected at the N-terminus with TFA/DCM (1:1) and then coupled with the alpha-hydroxy-naphthylacetic acid. The methyl ester was hydrolyzed with LiOH and then the silyl group was removed from the hydroxyl function by treatment with tetra-t-butylammonium fluoride [(t-Bu)$_4$NF] in THF.

| | |
|---|---|
| Molecular Formula | $C_{34}H_{44}N_2O_6$ |
| Molecular Weight | 576.73 |
| tlc Rf (solvent) | Rf = 0.12 in 10% Methanol/dichloromethane |
| Purification: | 10% Methanol/dichloromethane |
| Mass spec (MH+) | 577 |

Example 6

This pentapeptide isostere was prepared to test the efficacy of the alpha-hydroxy-naphthylacetic acid as an N-terminal group peptidomimetic in an oligopeptide sequence that demonstrated good activity (see Ex. 1). The hydroxyethylene moiety was prepared via the method of Scheme I. Resin supported synthesis was employed to prepare the molecule by bonding Boc-Phg to a resin support and then sequentially constructed by removal of the Boc protecting group and HOBt/EDC coupling in turn with glutamic acid methyl ester, valine, the hydroxyethylene isostere of Scheme I and finally with alpha-hydroxy-naphthylacetic acid. The product was then cleaved from the solid support and protecting groups were removed as described in the examples above.

| | |
|---|---|
| Molecular Formula | $C_{41}H_{54}N_4O_{10}$ |
| Molecular Weight | 762.9 |
| Purification: | 500 analytical HPLC trace (Gradient: 20–50% [B] in 30 minutes, [A] Buffer = 0.1% TFA/H2O; [B] Buffer = 0.1% TFA/Acetonitrile) revealed two diastereomers eluting at 19.4 and 21.0 minutes |
| Mass spec (M + Na+) [M + K+] | 763.6 (785.6) [801.6] |

The preparation of examples 1–6, as described in Table 1 above, is outlined in Scheme I.

Example 7

After the C-terminal coupling was accomplished as described above, the lactone was subjected to aminolysis at refluxing temperatures with 3,5-dimethylcyclohexylamine in the presence of AlMe$_3$ and a suitable organic solvent to provide the subject compound.

| | |
|---|---|
| Molecular Formula | C36H51F2N3O6 |
| Molecular Weight | 659 |
| tlc Rf (solvent) | 0.15 (5% iPrOH/CHCl3) |
| Purification: | Flash chromatography |
| Mass spec (M + H+) | (CI) 660.4 |

Example 8

After the C-terminal coupling was accomplished as described above, the lactone was subjected to aminolysis at refluxing temperatures with 6-aminohexanoic acid in the presence of AlMe$_3$ and a suitable organic solvent to provide the subject compound.

| | |
|---|---|
| Molecular Formula | $C_{34}H_{47}F_2N_3O_6$ |
| Molecular Weight | 631 |
| tlc Rf (solvent) | 0.15 (5% MeOH/CH2Cl2) |
| Purification: | Flash chromatography |
| Mass spec (M + H+) | (CI) 632.2 |

Example 9

After the C-terminal coupling was accomplished as described above, the lactone was subjected to aminolysis at refluxing temperatures with 8-aminooctanoic acid in the presence of AlMe$_3$ and a suitable organic solvent which was then dissolved in MeOH and treated with HCl gas to provide the desired methyl ester.

| | |
|---|---|
| Molecular Formula | $C_{37}H_{53}F_2N_3O_6$ |
| Molecular Weight | 673 |
| tlc Rf (solvent) | 0.4 (5% iPrOH/CHCl$_3$) |
| Purification: | Flash chromatography |
| Mass spec (M + H+) | (CI) 674.4 |

Example 10

After the C-terminal coupling was accomplished as described above, the lactone was subjected to aminolysis at refluxing temperatures with 4-carboxycyclohexylmethylamine in the presence of AlMe$_3$ and a suitable organic solvent to provide the subject compound.

| | |
|---|---|
| Molecular Formula | $C_{36}H_{49}F_2N_3O_6$ |
| Molecular Weight | 657 |
| tlc Rf (solvent) | 0.3 (10% MeOH/CH$_2$Cl$_2$) |
| Purification: | Flash chromatography |
| Mass spec (M + H+) | (CI) 658.4 |

Example 11

The subject compound was prepared as in Example 10 except that in the first step of preparation of the chiral oxazolidine intermediate, 3-phenylpropionyl chloride (Aldrich Chemical) was substituted for n-butanoyl chloride.

| | |
|---|---|
| Molecular Formula | $C_{41}H_{51}F_2N_3O_6$ |
| Molecular Weight | 719.86 |
| Mass spec (M + Na+) | 743 |

Example 12

The subject compound was prepared as in Example 10 except that in the first step of preparation of the chiral oxazolidine intermediate, n-pentanoyl chloride was substituted for n-butanoyl chloride.

| | |
|---|---|
| Molecular Formula | $C_{37}H_{51}F_2N_3O_6$ |
| Molecular Weight | 671.37 |
| Mass spec (M + Na+) | 694.37 |

Example 13

The subject compound was prepared as in Example 10 except that in the first step of preparation of the chiral oxazolidine intermediate, n-propionyl chloride was substituted for n-butanoyl chloride.

| | |
|---|---|
| Molecular Formula | $C_{35}H_{47}F_2N_3O_6$ |
| Molecular Weight | 643.34 |
| Mass spec (M + Na+) | 666.34 |

The compound formulae referred to in Examples 14–22 correspond to those recited in CHART A. Furthermore, the following examples relate to those compounds recited in CHART A where $R_1$=—(CH$_2$)3,5-difluorobenzyl, $R_2$=Et, $R_N$=N',N'-dipropylisophthalamide, $R_C$=anti-4-aminomethylcyclohexanecarboxylic acid, and PROTECTING GROUP is Boc. The identity of the $R_2$ substituent is determined by the starting material (i.e. compounds of formula (XIII)) used in the synthesis of the intermediate (VII) as is outlined in CHART B. The intermediate (VII), prepared according to CHART B, is then incorporated into the synthetic scheme for the preparation of hydroxyethylene compounds of formula (XII), as outlined in CHART A, by reaction with the epoxide (VI).

Example 14

(L)-[2-(3,5-Difluorophenyl)-1-(methoxymethylcarbamoyl)-ethyl]-carbamic Acid Tert-butyl Ester (III)

(L)-2-tert-Butoxycarbonylamino-3-(3,5-difluorophenyl)-propionic acid (Synthetech Inc., II, 2.66 g, 8.83 mmol) was dissolved in a mixture of dry THF (5 mL) and dry DMF (2 mL) at rt. 1,1-Carbonyldiimidazole (1.71 g, 10.6 mmol) was added in one portion to this solution. After gas evolution ceased, a solution of N-methyl-O-methylhydroxylamine hydrochloride (0.955 g, 9.79 mmol) and diisopropylethylamine (1.6 mL, 9.19 mmol) in DMF (4 mL) was added at rt by syringe. This was stirred at rt for 17 h, whereupon the reaction was quenched with 10% citric acid. The mixture was extracted with EtOAc. The organic extract was washed (saturated NaHCO$_3$, saturated NaCl), dried (MgSO$_4$), filtered, and concentrated under reduced pressure. The residue was purified by flash chromatography (30% EtOAc/hexanes elution) to give an oil as product: M+Na+367.1.

Example 15

(L)-[1-(3,5-Difluorobenzyl)-2-oxoethyl]-carbamic Acid Tert-butyl Ester (IV)

(L)-[2-(3,5-Difluorophenyl)-1-(methoxymethylcarbamoyl)-ethyl]-carbamic acid tert-butyl ester (III, 2.56 g) was dissolved in dry THF (50 mL) and cooled to 0° C. To this mixture was added powder lithium aluminum hydride (285 mg) in portions over 5 min. The resulting suspension was stirred at 0° C. for 1 h. Reaction was quenched at 0° C. by slow addition of saturated citric acid until gas evolution ceased, followed by dropwise addition of 10% aqueous citric acid (30 mL). This was then allowed to warm to rt. The layers were separated and the aqueous extracted with $Et_2O$. The combined organic extracts were washed (saturated $NaHCO_3$, saturated NaCl), dried ($MgSO_4$), filtered, and concentrated under reduced pressure to give a solid, which was used without further purification.

Example 16

(L)-[1-(3,5-Difluorobenzyl)allyl]-carbamic Acid Tert-butyl Ester(V)

Potassium hydride (35% suspension in mineral oil, 1.76 g) was suspended in a mixture of dry THF (20 mL) and DMSO (4 mL), and was cooled to 0° C. 1,1,1,3,3,3-Hexamethyldisilazane (4.0 mL) was added by syringe, and the mixture was stirred for 45 min at 0° C. Methyltriphenylphosphonium bromide (5.57 g) was added, and the resulting yellow slurry was stirred at 0° C. for 1 h, whereupon the mixture was cooled to -78° C. A solution of (L)-[1-(3,5-Difluorobenzyl)-2-oxoethyl]-carbamic acid tert-butyl ester (IV, 2.2 g) in THF (15 mL) at -78° C. was added by cannula. The resulting suspension was stirred at -78° C. for 15 min, then was allowed to warm to rt for 16 h. MeOH (2 mL) and half-saturated sodium bicarbonate solution (100 mL) were added, and the mixture was extracted with EtOAc (2×50 mL). The combined organic extracts were washed (water saturated NaCl) dried ($MgSO_4$), filtered, and concentrated under reduced pressure. The residue was purified by flash chromatography (10–20% $Et_2O$/hexanes) to give a solid as product: M+Na+306.1.

Example 17

(1S, 2R)-[2-(3,5-Difluorophenyl)-1-oxiranylethyl]-carbamic Acid Tert-butyl Ester (VI)

(L)-[1-(3,5-Difluorobenzyl)allyl]-carbamic acid tert-butyl ester(V, 3.3 g) was dissolved in $CH_2Cl_2$ (130 mL) and m-chloroperbenzoic acid (50–55% pure, 16.0 g) was added with stirring at rt. After 23 h, the reaction mixture was diluted with $Et_2O$, washed (10% $Na_2SO_3$, saturated $NaHCO_3$, saturated NaCl), dried ($MgSO_4$), filtered, and concentrated under reduced pressure to give a solid: M+Na+ 322.1.

Example 18

(1S,2S, 4R)-[1-(3,5-Difluorobenzyl)-4-((3aS, 8aR)-2,2-dimethyl-8,8a-dihydro-3aH-indeno[[1,2-d]oxazole-3-Carbonyl)-2-hydroxyhexyl]-carbamic Acid Tert-butyl Ester (VIII)

(1S, 2S)-[2-(3,5-Difluorophenyl)-1-oxiranylethyl]-carbamic acid tert-butyl ester (VI, 113 mg) and 1-((3aS, 8aR)-2,2-Dimethyl-8,8a-dihydro-3aH-indeno[1,2-d]oxazol-3-yl)-butan-1-one (VII, 94 mg) were combined in dry THF (3 mL), and cooled to -78° C. To this solution was added BuLi (2.5 M in hexanes, 0.32 mL) over 5 min., whereupon the solution was allowed to warm to 0° C. for 1.5 h. The reaction mixture was partitioned between 0.5 N HCl (4 mL) and 1:1 EtOAc/hexanes (2×4 mL). The combined organic layers were dried ($MgSO_4$), filtered, and concentrated under reduced pressure. The residue was purified by flash chromatography (20–30% EtOAc/hexanes) to give an oil: MH+559.1.

Example 19

[2-(3,5-Difluorophenyl)-1—(S)—(4-(R)-ethyl-5-oxo-tetrahydrofuran-2-(S)-yl)-ethyl]-carbamic Acid Tert-butyl Ester (IX)

(1S,2S, 4R)-[1-(3,5-Difluorobenzyl)-4-((3aS, 8aR)-2,2-dimethyl-8,8a-dihydro-3aH-indeno[1,2-d]oxazole-3-carbonyl)-2-hydroxyhexyl]-carbamic acid tert-butyl ester (VIII, 60 mg) was dissolved in 5:1 toluene/$CH_2Cl_2$ (3 mL), and p-toluenesulfonic acid monohydrate (23 mg) was added. This was stirred at rt for 18 h. The mixture was then filtered, and partitioned between half-saturated $NaHCO_3$ (3 mL) and 1:1 EtOAc/hexanes (2×3 mL). The combined organic layers were dried ($MgSO_4$), filtered, and concentrated under reduced pressure. Flash chromatography of the residue afforded desired product as a solid: MH+370.2.

Example 20

5S-[1S-Amino-2-(3,5-difluorophenyl)ethyl]-3R-ethyldihydrofuran-2-one (X)

[2-(3,5-Difluorophenyl)-1-(S)-(4-(R)-ethyl-5-oxo-tetrahydrofuran-2-(S)-yl)-ethyl]-carbamic acid tert-butyl ester (IX, 313 mg) was dissolved in $CH_2Cl_2$ (1 mL) at rt, whereupon $CF_3COOH$ (1 mL) was added. This was stirred at rt for 1 h, then concentrated under reduced pressure. This was used in the next reaction without further purification.

Example 21

N-{2-(3,5-Difluorophenyl)-(1S, 2S, 4R)-[1-(4-ethyl-5-oxotetrahydrofuran-2-yl)]ethyl}-N',N'-dipropylisophthalamide (XI)

5S-[1S-Amino-2-(3,5-difluorophenyl)ethyl]-3R-ethyldihydrofuran-2-one (X, 228 mg theoretical) was combined with triethylamine (0.7 mL) in dry DMF (2 mL) at 0° C. N,N-Dipropylisophthalamic acid (242 mg) was added and dissolved. 1-Hydroxybenzotriazole (224 mg) and 1-(3-dimethylaminopropyl)-3-ethylcarbodiimide hydrochloride (320 mg) were added in succession. The mixture was stirred at 0° C. for 5 min., then allowed to warm to rt for 4 h. This was then diluted with 10% citric acid, and extracted 3× with EtOAc. The combined organic extracts were washed (saturated $NaHCO_3$, saturated NaCl), dried ($MgSO_4$), filtered, and concentrated under reduced pressure. The residue was purified by flash chromatography (40% EtOAc/hexanes elution) to give a solid: MH+501.3.

Example 22

4-(anti)-{[6-(3,5-Difluorophenyl)-5-(S)-(3-dipropylcarbamoylbenzoylamino)-2-(R)-ethyl-4-(S)-hydroxyhexanoylamino]-methyl}cyclohexanecarboxylic acid (XII)

Anti-4-Aminomethylcyclohexanecarboxylic acid (57 mg) was suspended in 1,2-dichloroethane (2 mL), and cooled to 0° C. Trimethylaluminum (2.0 M in toluene, 0.21 mL) was added, followed by a solution of N-{2-(3,5-Difluorophenyl)-(1S, 2S, 4R)-[1-(4-ethyl-5-oxotetrahydrofuran-2-yl)]ethyl}-N',N'-dipropylisophthalamide (XI, 30 mg) in 1,2-dichloroethane (1 mL). This was then warmed to reflux for 1.5 h, whereupon the reaction mixture was cooled to 0° C., and the reaction quenched with 3 N HCl (2 mL). The slurry was stirred at 0° C. for 30 min, and then extracted with 3×5 mL 10% iPrOH/CHCl₃. The combined organic extracts were dried (MgSO₄), filtered, and concentrated under reduced pressure. The residue was purified by flash chromatography (5–10% MeOH/CH₂Cl₂ elution) to give a solid: MH+ 658.4.

The compound formulae referred to in Examples 23–24 correspond to those recited in CHART B. Furthermore, the following examples relate to those compounds recited in CHART B R₂=Et.

Example 23

N-(1S, 2R)-(2-Hydroxyindan-1-yl)-butyramide (XV)

(1S, 2R)-cis-1-Amino-2-indanol (XIV, 1.5 g) was dissolved with triethylamine (1.5 mL) in dry THF (45 mL), and cooled to 0° C. Butyryl chloride (XIII, 1.05 mL) was added by syringe, and the resultant solution stirred 0° C. for 20 min, whereupon the reaction mixture was partitioned between half-saturated NH₄Cl (45 mL) and EtOAc (2×45 mL). The combined organic layers were dried dried (MgSO₄), filtered, and concentrated under reduced pressure to give a solid, which was taken to the next reaction without further purification.

Example 24

1-((3aS, 8aR)-2,2-Dimethyl-8,8a-dihydro-3aH-indeno [1,2-d]oxazol-3-yl)-butan-1-one (VII)

N-(1S, 2R)-(2-Hydroxyindan-1-yl)-butyramide (XV, 2.2 g) and 2-methoxypropene (5 mL) were combined with CH₂Cl₂ (70 mL) at rt, and methanesulfonic acid (0.05 mL) was added. After 20 min at rt, the reaction mixture was partitioned between half-saturated NaHCO₃ (30 mL) and CH₂Cl₂ (2×30 mL). The combined organic layers were dried dried (MgSO₄), filtered, and concentrated under reduced pressure to give an oil as product: MH+ 260.1.

Examples 25–30 recited below relate to the synthesis for N-terminus capping groups.

Example 25

Hydroxylated and Benzylated N-Terminal Capping Groups

The making of hydroxylated and benzylated N-terminal capping groups from aromatic acetic acid starting materials is illustrated in Scheme III below. Moersch, G W and Zwiesler, M L. (*Synthesis,* 1971, 647–648, ref. 1 in Scheme III) demonstrate a synthesis useful for preparing an arylalkylhydroxycarboxylic acid N-terminus capping group. The procedure here provides alpha hydroxylation of 1-naphthylacetic acid, using lithium diethylamine and oxygen. Hon, Yung-Son, Chang, Rong-Chi, Chau, Tay-Yuan (*Heterocycles,* 1990, Vol. 31, No. 10, 1745–1750, ref. 2 in Scheme III) demonstrate a synthesis of the corresponding benzyl ether from the α-hydroxyaromatic by esterification of the carboxy function and etherification with benzyl bromide. Either the alpha-hydroxy acid or the benzyl ether derivative is suitable as a N-terminal cap.

Scheme III

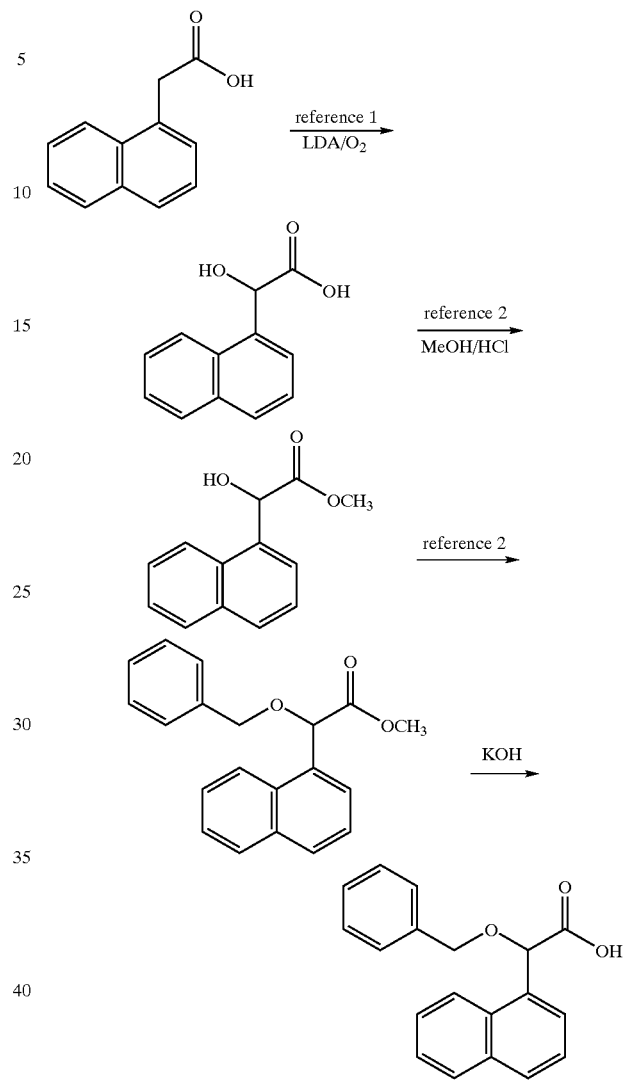

Example 26

Preparation of Carboxybenzamides

Scheme IVA

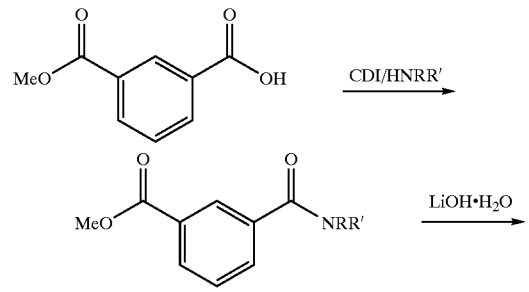

-continued

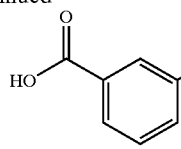

Methyl isoplithalate (Aldrich Chemical, Milwaukee, Wis., (1 equiv, 11.1 mmol) was dissolved in 50:50 THF:DMF (20 mL) before the addition of 1,1' carbonyl-duimidazole (CDI) (1.2 equiv, 13.3 mmol) at ambient temperature. Upon addition of CDI, an evolution of gas ($CO_2$), was observed. After gas evolution subsided (approximately one minute or less), the amine (1.2 equiv, 1.3 mmol) was added. After 12 h of stirring at ambient temperature, the reaction was partitioned between saturated aqueous $NH_4Cl$ and ethyl acetate, and the aqueous layer was extracted twice more with ethyl acetate. The organic extracts were then washed with saturated aqueous solutions of $NaHCO_3$ and NaCl, and dried over anhydrous $MgSO_4$ or $NaSO_4$. Filtration of the drying agent and removal of solvents in vacuo gave the crude white solid or clear oil. Purification of these compounds if needed was achieved via chromatography on silica gel with 30–40% ethyl acetate in hexanes.

The methyl isophthalate mono-alkyl or di-alkyl amide was then treated with $LiOH.H_2O$ (3 equiv, 33.3 mmol) in a minimum amount of 1:2:1 $THF:MeOH:H_2O$ and allowed to stir overnight at ambient temperature. After 12 h, the solvents were removed in vacuo and subsequently partitioned between $H_2O$ and ethyl acetate. If emulsions prohibit separation of the two layers, a small amount of brine was added to aid in separation. The aqueous layer was extracted once more with ethyl acetate (to remove any unreacted starting material). The aqueous layer was then acidified with concentrated HCl until pH≦3. The cloudy-white acidic aqueous solution thus obtained was then extracted three times with ethyl acetate. These combined organic extracts were dried over anhydrous $MgSO_4$ or $NaSO_4$. Filtration of the drying agent and removal of solvents in vacuo gave a solid. The mono- or di-alkyl amide isophthalate was used crude in the next reaction.

Example 27

Preparation of Carboxybenzamides

Scheme IVB

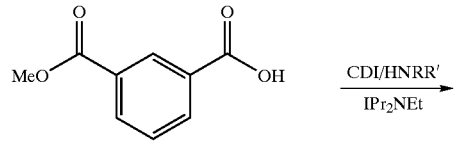

-continued

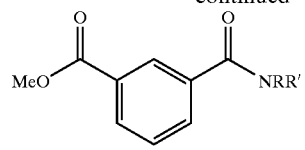

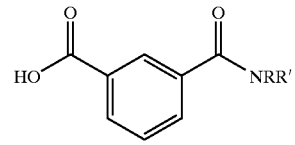

Methyl isophthalate (1 equiv, 11.1 mmol) was dissolved in 50:50 THF:DMF (20 mL) before the addition of 1,1' carbonyldiimidazole (CDI) (1.2 equiv, 13.3 mmol) at ambient temperature. Upon addition of CDI, evolution of gas ($CO_2$), was observed. After gas evolution subsided (approximately one minute or less), the amine (1.2 equiv, 13.3 mmol) dissolved in DMF and diisopropylethyl amine (1.2 equiv, 13.3 mmol) was added. After 12 h of stirring at ambient temperature, the reaction was partitioned between saturated aqueous $NH_4Cl$ and ethyl acetate, and the aqueous layer was extracted twice more with ethyl acetate. The organic extracts were then washed with saturated aqueous solutions of $NaHCO_3$ and NaCl, and dried over anhydrous $MgSO_4$ or $NaSO_4$. Filtration of the drying agent and removal of solvents in vacuo gave a solid or oil. Purification of these compounds if needed was achieved via chromatography on silica gel with 30–40% ethyl acetate in hexanes.

The methyl isophthalate mono-alkyl or di-alkyl amide (1 equiv, 11.1 mmol) was then treated with $LiOH.H_2O$ (3 equiv, 33.3 mmol) in a minimum amount of 1:2:1 $THF:MeOH:H_2O$ and allowed to stir overnight at ambient temperature. After 12 h, the solvents were removed in vacuo and subsequently partitioned between $H_2O$ and ethyl acetate. If emulsions prohibit separation of the two layers, a small amount of brine was added to aid in separation. The aqueous layer was extracted once more with ethyl acetate (to remove any unreacted starting material). The aqueous layer was then acidified with concentrated HCl until pH≦3. The cloudy-white acidic aqueous solution thus obtained was then extracted three times with ethyl acetate. These combined organic extracts were dried over anhydrous $MgSO_4$ or $Na_2SO_4$. Filtration of the drying agent and removal of solvents in vacuo gave a solid. The mono- or di-alkyl amide isophthalate was used crude in the next reaction.

Example 28

Preparation of Primary Amide

Scheme IVC

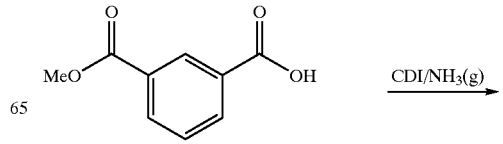

-continued

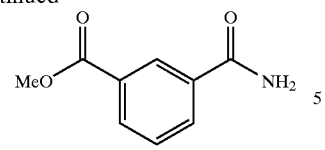

Methyl isophthalate (1 equiv, 11.1 mmol) was dissolved in 50:50 THF:DMF (20 mL) before the addition of 1,1' carbonyldiimidazole (CDI) (1.2 equiv, 13.3 mmol) at ambient temperature. Upon addition of CDI, an evolution of gas ($CO_2$), was observed. After five minutes, ammonia gas was bubbled into the solution through a syringe needle for 1 h. Since the reaction was heating up due to an exotherm, the reaction was cooled to 0° C. for the duration of the hour. The reaction was then left stirring under a balloon of ammonia overnight at ambient temperature. After 12 h, the reaction was partitioned between saturated aqueous $NH_4Cl$ and ethyl acetate, and the aqueous layer was extracted twice more with ethyl acetate. The organic extracts were then washed with saturated aqueous solutions of $NaHCO_3$ and NaCl, and dried over anhydrous $MgSO_4$ or $NaSO_4$. Filtration of the drying agent and removal of solvents in vacuo gave a solid or oil. Purification via chromatography on silica gel with 5% isopropanol in chloroform gave the desired primary amide.

The methyl isophthalate primary amide (7.26 mmol) was then treated with $LiOH.H_2O$ (3 equiv, 21.8 mmol) in a minimum amount of 1:2:1 $THF:MeOH:H_2O$ and allowed to stir overnight at ambient temperature. After 12 h, the solvents were removed in vacuo and subsequently partitioned between $H_2O$ and ethyl acetate. The aqueous layer was extracted once more with ethyl acetate (to remove any unreacted starting material). The aqueous layer was then acidified with concentrated HCl until pH≦3. The cloudy-white acidic aqueous solution thus obtained was then extracted three times with ethyl acetate. These combined organic extracts were dried over anhydrous $MgSO_4$ or $NaSO_4$. Filtration of the drying agent and removal of solvents in vacuo gave a solid. The mono- or di-alkyl amide isophthalate was used crude in the next reaction.

Example 29

Preparation of Heterocyclic Amides

Scheme IVD

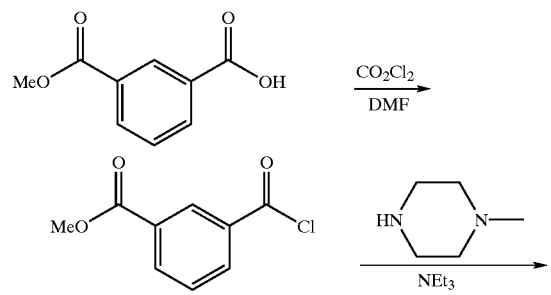

-continued

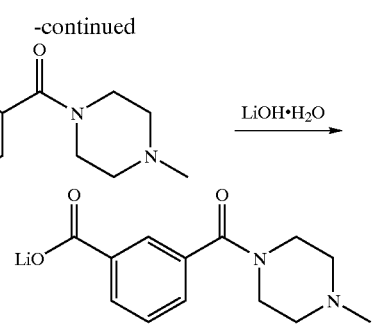

Methyl isophthalate (1.2 equiv, 2.78 mmol) was dissolved in dry CH2Cl2 and three drops of DMF (catalytic). The solution was cooled to 0° C. before the drop-wise addition of oxalyl chloride (2 equiv, 4.63 mmol). The mixture was stirred at 0° C. for 1 h. The mixture never dissolved. After 1 h, the solvents were removed in vacuo. The acid chloride was left under vacuum overnight.

The crude acid chloride (1 equiv, 2.78 mmol) was dissolved in dry $CH_2Cl_2$ and cooled to 0° C. before the addition of $NEt_3$ (5 equiv, 11.6 mmol) and N-methyl piperidine (6 equiv, 13.9 mmol). The reaction was stirred at 0° C. for 2 h before the solvents were removed in vacuo. The residue was diluted with $H_2O$ and ethyl acetate and the layers were separated. The aqueous layer was extracted twice more with ethyl acetate, and the combined organic extracts were washed with saturated aqueous $NaHCO_3$, and dried over anhydrous $MgSO_4$. Filtration of the drying agent and removal of solvents in vacuo gave the crude product.

The crude amide (1 equiv, 2.19 mmol) was then treated with $LiOH-H_2O$ (1 equiv, 2.19 mmol) in a minimum amount of 1:2:1 $THF:MeOH:H_2O$ and allowed to stir overnight at ambient temperature. After 12 h, the solvents were removed in vacuo and subsequently partitioned between $H_2O$ and ethyl acetate. The aqueous layer was extracted once more with ethyl acetate (to remove any unreacted starting material.) Removal of $H_2O$ from aqueous layer in vacuo gave a solid.

Example 30

Preparation of Aromatic Alpha-hydroxy acids (Illustrated by the Preparation with (α-hydroxy-α-(2-biphenyl)acetic Acid)

Scheme V

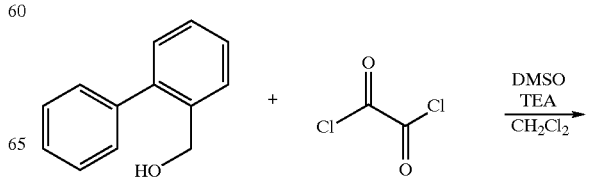

89

-continued

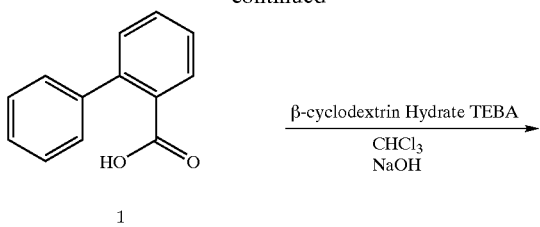

A solution of CH$_2$Cl$_2$ (25 mL) and oxalyl chloride (2 mL, 21.16 mmol) was placed in a 100-mL round bottom flask kept under nitrogen. The oxalyl chloride solution was stirred at −50 to −60° C. Me$_2$SO (2.5 mL, 35.82 mmol) was dissolved in CH$_2$Cl$_2$ (5 mL). The Me$_2$SO was added dropwise to the stirred oxalyl chloride solution at −50 to −60 degrees C. The reaction mixture was stirred for 2 min and the 2-phenylbenzyl alcohol (16.28 mmol in 10 mL CH$_2$Cl$_2$) was added within 5 min; stirring was continued for an additional 60 min. TEA (11.30 mL, 81.4 mmol) was added and the reaction mixture was stirred for 60 min and then allowed to warm to room temperature. Water (60 mL) was then added and the aqueous layer was reextracted with additional CH$_2$Cl$_2$ (60 mL). The organic layers were combined, washed with saturated NaCl solution (120 mL), and dried over anhydrous MgSO$_4$. The filtered solution was concentrated in a rotary evaporator to dryness. The oil was chromatographed on silica gel (98:2 hexanes:EtOAc) to give 1.

A mixture of 5.46 mmol of aromatic aldehyde (1) in 10 mL of CHCl$_3$ and beta-cyclodextrins (CDs) (0.11 mmol) and triethylbenzylammonium chloride (TEBA) (0.273 mmol) in a flask equipped with a magnetic stirrer and dropping funnel was stirred for 20 minute at 50 degrees C. Then 10 g of sodium hydroxide dissolved in 10 mL of water was added dropwise to the flask with stirring. After completion of this addition, the reaction was continued for 8 h with the temperature maintained at 50 degrees C. Then enough of distilled water was added to dissolve the precipitate formed during the reaction, and the resulting solution was thoroughly washed with ether, adjusted to pH 3 with dilute hydrochloric acid and extracted with 3×30 mL of ether. The extract was dried with anhydrous sodium sulfate, then evaporated to dryness and the remaining precipitate was subjected to column chromatography on silica gel using DCM:MeOH:AcOH (95:5:1) to give 2.

Examples 31 and 32 recited below relate to the synthesis for N-terminus capping groups.

90

Example 31

1-Amino-3,5-cis,cis-dimethyl Cyclohexyldicarboxylate

To 10 g (47.85 mmole) of dimethyl-5-isophthalate in 25 ml of acetic acid and 50 ml of methanol was added 5 g of 5% rhodium in alumina in a high-pressure bottle, which was saturated with hydrogen at 55 psi and shaken for one week of time.

Scheme VI A

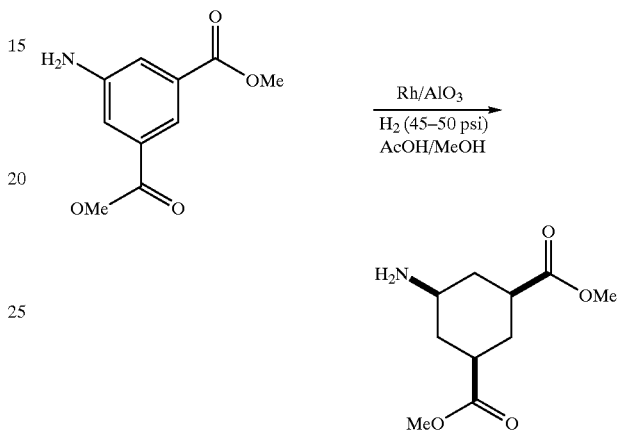

The mixture was then filtered through a thick layer of Celite cake and rinse with methanol three times, the solvents was concentrated and the crude solid was triturated with diethyl ether and filtered again, it afforded 1-amino-3,5-cis, cis-dimethyl cyclohexyldicarboxylate, reverse phase HPLC has shown a purity of 94.4%.

Example 32

1-Amino-3, 5-cis,cis-dimethoxy Cyclohexane

To 10 g (65.36 mmole) of 3,5-dimethoxyaniline was reacted as described in the procedure above and afforded 1-amino-3,5- cis,cis-dimethoxy cyclohexane.

Scheme VI B

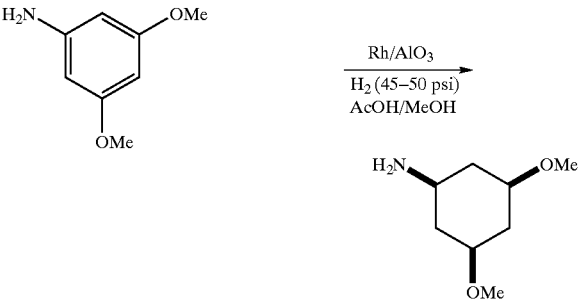

Following the general procedure as outlined in Examples 14–22 and making non-critical variations the following substitute amines of formula (XII) are obtained. These substitute amines of formula (XII) are listed in Tables 2, 3, and 4 as Examples.

TABLE 2

[Structure: N,N-dipropyl isophthalamide with (S)-benzylamide bearing 3,5-difluorobenzyl, (S)-OH, (R)-ethyl, and C-terminal C(O)X group]

| | Example | MH+ | C-terminus (X) |
|---|---|---|---|
| N-[(1S, 2S, 4R)-1-(3,5-Difluorobenzyl)-4-(syn, syn)-(3,5-dimethoxy-cyclohexylcarbamoyl)-2-hydroxyhexyl]-N,N-dipropylisophathalamide | 33 | 660.4 | HN—(3,5-dimethoxycyclohexyl) |
| 6-[6-(3,5-Difluorophenyl)-5-(S)-(3-dipropylcarabamoylbenzoylamino)-2-(R)-ethyl-4-(S)-hydroxy-hexanoylamino]-hexanoic acid | 34 | 632 | NH(CH$_2$)$_5$CO$_2$H |
| 5-[6-(3,5-Difluorophenyl)-5-(S)-(3-dipropyl-carbamoylbenzoylamino)-2-(R)-ethyl-4-(S)-hydroxy-hexanoylamino]-pentanoic acid | 35 | 618.3 | NH(CH$_2$)$_4$CO$_2$H |
| 4-[6-(3,5-Difluorophenyl)-5-(S)-(3-dipropyl-carbamoylbenzoylamino)-2-(R)-ethyl-4-(S)-hydroxy-hexanoylamino]-butyric acid | 36 | 603.7 | NH(CH$_2$)$_3$CO$_2$H |
| 3-[6-(3,5-Difluorophenyl)-5-(S)-(3-dipropyl-carbamoylbenzoylamino)-2-(R)-ethyl-4-(S)-hydroxyhexanoyl-amino]-propionic acid | 37 | 590.3 | NH(CH$_2$)$_2$CO$_2$H |
| 8-[6-(3,5-Difluorophenyl)-5-(S)-(3-dipropyl-carbamoylbenzoylamino)-2-(R)-ethyl-4-(S)-hydroxy-hexanoylamino]-ocatanoic acid | 38 | 660.4 | NH(CH$_2$)$_7$CO$_2$H |
| 8-[6-(3,5-Difluoro-phenyl)-5-(S)-(3-dipropyl-carbamoyl-benzoylamino)-2-(R)-ethyl-4-(S)-hydroxy-hexanoyl-amino]-octanoic acid methyl ester | 39 | 674.4 | NH(CH$_2$)$_7$CO$_2$Me |
| N-[4-(R)-Butylcarbamoyl-1-(S)-(3,5-di-fluoro-benzyl)-2-(S)-hydroxy-hexyl]-N,N-dipropyl-isophthalamide | 40 | 574.3 | NHBu |
| N-[1-(S)-(3,5-Difluoro-benzyl)-2-(S)-hy-droxy-4-(R)-isobutylcarbamoyl-hexyl]-N,N-dipropyl-isophthalamide | 41 | 574.5 | NHiBu |
| N-[4-(R)-Benzylcarbamoyl-1-(S)-(3,5-di-fluoro-benzyl)-2-(S)-hydroxy-hexyl]-N,N-dipropyl-isophthalamide | 42 | 608.3 | NHBn |
| N-[4-(R)-(Cyclohexylmethyl-carba-moyl)-1-(S)-(3,5-difluoro-benzyl)-2-(S)-hy-droxy-hexyl]-N,N-dipropyl-iso-phthalamide | 43 | 614.3 | HN-CH$_2$-cyclohexyl |
| N-[1-(S)-(3,5-Difluoro-benzyl)-2-(S)-hy-droxy-4-(R)-(piperidine-1-carbo-nyl)-hexyl]-N,N-dipropyl-isophthalamide | 44 | 586.3 | piperidin-1-yl |
| N-[1-(S)-(3,5-Difluoro-benzyl)-4-(R)-(2-dimethyl-amino-ethylcarbamoyl)-2-(S)-hy-droxy-hexyl]-N,N-dipropyl-isophthalamide | 45 | 589.3 | HN-CH$_2$CH$_2$-N(CH$_3$)$_2$ |
| N-[4-(R)-(Butyl-methyl-carbamoyl)-1-(S)-(3,5-di-fluoro-benzyl)-2-(S)-hy-droxy-hexyl]-N,N-dipropyl-iso-phthalamide | 46 | 588.1 | N(Me)(Bu) |
| N-[1-(S)-(3,5-Difluoro-benzyl)-2-(S)-hydroxy-4-(R)-(3-hy-droxy-propylcarbamoyl)-hexyl]-N,N-di-propyl-isophthalamide | 47 | 576.3 | HN-CH$_2$CH$_2$CH$_2$-OH |

TABLE 2-continued

| | Example | MH+ | C-terminus (X) |
|---|---|---|---|
| 4-([6-(3,5-Difluoro-phenyl)-5-(S)-(3-dipropyl-carbamoyl-benzoylamino)-2-(R)-ethyl-4-(S)-hydroxy-hexanoylamino]-methyl)-cyclohexanecarboxylic acid methyl ester | 48 | 672.0 | H₂N-CH₂-cyclohexyl-CO₂Me |
| N-[1-(S)-(3,5-Difluoro-benzyl)-4-(R)-(3-dimethyl-amino-propylcarbamoyl)-2-(S)-hydroxy-hexyl]-N,N-dipropyl-isophthalamide | 49 | 608.0 | HN-CH₂CH₂CH₂-N(CH₃)₂ |

TABLE 3

| | Example | MH+ | X |
|---|---|---|---|
| 4-(anti)-([6-(3,5-Difluoro-phenyl)-5-(S)-(3-dipropylcarbamoyl-benzoyl-amino)-2-(R)-ethyl-4-(S)-hydroxy-hexanoylamino]-methyl)-cyclohexanecarboxylic acid | 50 | 658.4 | Et |
| 4-(anti)-([6-(3,5-Difluoro-phenyl)-5-(S)-(3-dipropylcarbamoyl-benzoyl-amino)-4-(S)-hydroxy-2-(R)-methyl-hexanoylamino]-methyl)-cyclohexanecarboxylic acid | 51 | 644.3 | Me |
| 4-(anti)-([6-(3,5-Difluoro-phenyl)-5-(S)-(3-dipropylcarbamoyl-benzoyl-amino)-4-(S)-hydroxy-2-(R)-propyl-hexanoylamino]-methyl)-cyclohexanecarboxylic acid | 52 | 672.3 | nPr |
| 4-(anti)-([6-(3,5-Difluoro-phenyl)-5-(S)-(3-dipropylcarbamoyl-benzoyl-amino)-4-(S)-hydroxyl-2-(R)-isobutyl-hexanoylamino]-methyl)-cyclohexanecarboxylic acid | 53 | 686.3 | iBu |
| 4-(anti)-([6-(3,5-Difluoro-phenyl)-5-(S)-(3-dipropylcarbamoyl-benzoyl-amino)-4-(S)-hydroxy-hexanoylamino]-methyl)-cyclohexanecarboxylic acid | 54 | 630.3 | H |
| 4-(anti)-([2-(R)-Benzyl-6-(3,5-difluoro-phenyl)-5-(S)-(3-dipropyl-carbamoyl-benzoylamino)-4-(S)-hydroxy-hexanoylamino]-methyl)-cyclohexanecarboxylic acid | 55 | 720.3 | Bn |

TABLE 4

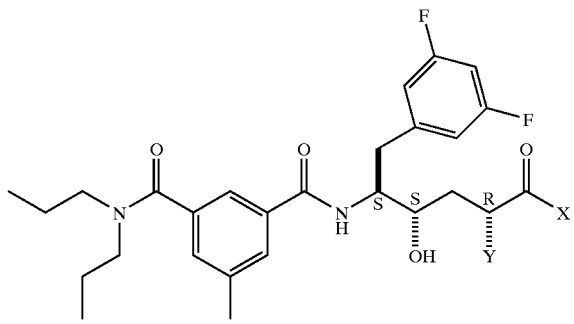

| | Example | MH+ | X | Y |
|---|---|---|---|---|
| 4-(anti)-([6-(3,5-Difluoro-phenyl)-5-(S)-(3-dipropyl-carbamoyl-5-methyl-benzoylamino)-2-(R)-ethyl-4-(S)-hydroxy-hexanoylamino]-methyl)-cyclohexanecarboxylic acid | 56 | 672.2 | H₂N-CH₂-cyclohexyl-CO₂Me | Et |
| 4-(anti)-([6-(3,5-Difluoro-phenyl)-5-(S)-(3-dipropyl-carbamoyl-5-methyl-benzoylamino)-2-(R)-ethyl-4-(S)-hydroxy-hexanoylamino]-methyl)-cyclohexanecarboxylic acid methyl ester | 57 | 686 | H₂N-CH₂-cyclohexyl-CO₂Me | Et |
| N-[1-(S)-(3,5-Difluoro-benzyl)-2-(S)-hydroxy-4-(R)-(2-morpholin-4-yl-ethylcarbamoyl)-pentyl]-5-methyl-N,N-dipropyl-isophthalamide | 58 | 631.2 | HN-CH₂CH₂-morpholine | Me |
| N-[1-(S)-(3,5-Difluoro-benzyl)-2-(S)-hydroxy-4-(R)-iso-butylcarbamoyl-pentyl]-5-methyl-N,N-dipropyl-isophthalamide | 59 | 574.3 | HN-iBu | Me |
| N-[4-(R)-(2-Diethylamino-ethylcarbamoyl)-1-(S)-(3,5-difluoro-benzyl)-2-(S)-hydroxy-pentyl]-5-methyl-N,N-dipropyl-isophthalamide | 60 | 617.3 | HN-CH₂CH₂-NEt₂ | Me |
| N-[1-(S)-(3,5-Difluoro-benzyl)-2-(S)-hydroxy-4-(R)-[(tetrahydro-furan-2-ylmethyl)-carbamoyl]-pentyl]-5-methyl-N,N-dipropyl-isophthalamide | 61 | 602.3 | HN-CH₂-tetrahydrofuran | Me |
| N-[4-(R)-(Adamantan-2-ylcarbamoyl)-1-(S)-(3,5-difluoro-benzyl)-2-(S)-hydroxy-pentyl]-5-methyl-N,N-dipropyl-isophthalamide | 62 | 652.3 | HN-adamantyl | Me |
| N-[1-(S)-(3,5-Difluoro-benzyl)-2-(S)-hydroxy-4-(R)-methyl-5-morpholin-4-yl-5-oxo-pentyl]-5-methyl-N,N-dipropyl-isophthalamide | 63 | 588.3 | morpholino | Me |
| N-[4-(R)-Benzylcarbamoyl-1-(S)-(3,5-difluoro-benzyl)-2-(S)-hydroxy-pentyl]-5-methyl-N,N-dipropyl-isophthalamide | 64 | 608.3 | NHBn | Me |
| N-[1-(S)-(3,5-Difluoro-benzyl)-4-(R)-(4-fluoro-benzylcarbamoyl)-2-(S)-hydroxy-pentyl]-5-methyl-N,N-dipropyl-isophthalamide | 65 | 626.3 | NH-(4-F)—Bn | Me |

TABLE 5

| | Example | MH+ | X |
|---|---|---|---|
| N-[1-(S)-(3,5-Difluoro-benzyl)-2-(S)-hydroxy-4-(R)-phenethyl-carbamoyl-pentyl]-5-methyl-N,N-di-propyl-isophthalamide | 66 | 622.3 | HN-CH₂CH₂-Ph |
| N-[1-(S)-(3,5-Difluoro-benzyl)-4-(R)-[(furan-2-ylmethyl)-carba-moyl]-2-(S)-hydroxy-pentyl]-5-methyl-N,N-di-propyl-isophthalamide | 67 | 598.3 | HN-CH₂-furan |
| N-[1-(S)-(3,5-Difluoro-benzyl)-2-(S)-hydroxy-4-(R)-(prop-2-ynylcarba-moyl)-pentyl]-5-methyl-N,N-di-propyl-isophthalamide | 68 | 556.3 | HN-CH₂-C≡CH |

Example 69

Benzyl (1S)-2-(3,5-difluorophenyl)-1-[(2R)-oxiranyl]ethylcarbamate (VI)

Following the general procedure of EXAMPLE 17 and making non critical variations but starting with the alcohol (IV) Benzyl (1S, 2R)-3-chloro-1-(3,5-difluorobenzyl)-2-hydroxypropylcarbamate, the title compound is obtained.

Example 70

Enzyme Inhibition Assay

The compounds of the invention were analyzed for inhibitory activity by use of the MBP-C125 assay. This assay determines the relative inhibition of beta-secretase cleavage of a model APP substrate, MPB-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. Human brain beta-secretase was prepared from partially purified concentrated human brain tissue as described in Sindha et.al., 1999, Nature 402:537–554 and maintained in 0.20% Triton. Alternatively, recombinant full length enzyme (amino acids 1–501) was prepared from 293 cells expressing the transgenic enzyme.

Inhibition data was obtained from an ELISA which uses an anti-MBP capture antibody deposited on precoated and blocked 96-well high binding plates, followed by incubation with diluted enzyme reaction supernatant, incubation with the anti-SWI 92 specific biotinylated reporter antibody, and incubation with streptavidin/alkaline phosphatase. Cleavage of the intact MBP-C125SW fusion protein results in the generation of a truncated amino-terminal fragment, with the new SW-192 antibody-positive epitope exposed at the carboxy terminus. Detection was effected by a fluorescent substrate signal on cleavage by the phosphatase. ELISA only detected cleavage following Leu 596 at the substrate's APP-SW 751 mutation site.

Compounds were diluted in a 1:1 dilution series to a six-point concentration curve (two wells per concentration) which took up one 96-plate row per compound tested. Procedure:

Each of the test compounds was weighed out into a vial and DMSO was added to make up a 10 mM solution. To obtain a final compound concentration of 200 µM at the high point of a 6-point dilution curve, 100 µL of the 10 mM solution was added to well C1 of a 96-well V-bottom plate. Fifty µL of DMSO was added to odd wells of row C across the plate and 1:1 serial dilutions were made. 10 µL of each dilution was added to each of two wells on row C of a corresponding V-bottom plate to which 190 µL of 52 mM NaOAc/7.9% DMSO, pH 4.5 were pre-added. The NaOAc diluted compound plate was spun down to pellet precipitant and 20 µL/well was transferred to a corresponding flat-bottom plate to which 30 µL of ice-cold enzyme-substrate mixture (2.5 µL MBP-C125SW substrate, 0.03 µL enzyme and 24.5 ice cold 0.09% TX 100 per 30 microl) was added. The compound concentration in the final enzyme reaction was thus 50 times less than the starting concentration. The final reaction mixture of 200 microM compound for the highest curve point was in 5% DMSO, 20 mM NaAc, 0.06% TX 100, at pH 4.5. The enzyme reaction was started by warming the plates to 37 degrees C. After 90 minutes at 37 degrees C., 200 µL/well cold specimen diluent was added to stop the reaction and 20 µL/well was transferred to a corresponding anti-MBP antibody coated ELISA plate for capture, containing 80 µL/well specimen diluent. This reaction was incubated overnight at 4 degrees C. and the ELISA was developed the next day after a 2 hr. incubation with anti-192SW antibody, followed by Streptavidin-AP conjugate and flourescent substrate. The signal was read on a fluorescent plate reader.

Results:

Relative compound inhibition potency was determined by calculating the concentration of compound that showed a fifty-percent reduction in detected signal ($IC_{50}$) compared to the enzyme reaction signal in the control wells with no added compound.

For the purpose of grouping inhibitor activities of the compounds of the present invention disclosed in the data tables of this specification, the inhibitory activities have been ranked by their $IC_{50}$ concentrations according to following order:

| | |
|---|---|
| Group I: | compounds having an $IC_{50}$ less than 10 $\mu$M; |
| Group II: | compounds having an $IC_{50}$ of from 10 $\mu$M to and including 100 $\mu$M; |
| Group III: | compounds having an $IC_{50}$ of from 100 $\mu$M to and including 200 $\mu$M; |
| Group IV: | compounds having an $IC_{50}$ of greater than 200 $\mu$M. |

Example 71

Cell Free Inhibition Assay utilizing APP-KK

The synthetic APP substrate, Biotin-KVEANY-EVEGERC (oregon green) KK, having N-terminal biotin and made fluorescent by the covalent attachment of oregon green at the Cys residue was used. The N-terminal biotin is used to anchor the peptide to a substrate assay plate. Incubation was conducted under the following conditions: 10 TM APP substrate; 50 nM enzyme Asp2a), pH 4.5, 37 DEGREES C., for 2 hours. Activity of the beta-secretase enzyme is detected as the loss of oregon green flurophore, on the opposite side of the cleavage site from the Biotin anchor is released on cleavage of the substrate.

Incubation in the presence or absence of compound inhibitor demonstrates specific inhibition of beta-secretase enzymatic cleavage of its APP substrate.

Example 72

Beta-secretase Inhibition: P26-P4'SW Assay

The P26-P4'sw substrate is a peptide of the sequence:
(biotin) CGGADRGLTTRPGSGLTNIK-TEEISEVNLDAEF (SEQ ID NO:1).

The P26-P1 standard has the sequence:
(biotin) CGGADRGLTTRPGSGLTNIKTEEISEVNL (SEQ ID NO: 2).

Peptides were prepared by Anaspec, Inc. (San Jose, Calif.) using solid phase synthesis with boc-amino acids. Biotin was coupled to the terminal cysteine sulfhydryl by Anaspec, Inc. after synthesis of the peptide, using EZ-link Iodoacetyl-LC-Biotin (Pierce). Peptides are stored as 0.8–1.0 mM stocks in 5 mM Tris, with the pH adjusted to around neutral (pH 6.5–7.5) with sodium hydroxide.

For the enzyme assay, the substrate concentration can vary from 0–200 $\mu$M. Specifically for testing compounds for inhibitory activity, substrate concentration can be 1.0 $\mu$M. Compounds to be tested are added in DMSO, with a final DMSO concentration of 5%; in such experiments, the controls also receive 5% DMSO. Concentration of enzyme is varied, to give product concentrations with the linear range of the ELISA assay (125–2000 pM, after dilution).

These components are incubated in 20 mM sodium acetate, pH 4.5, 0.06% Triton X-100, at 37 degrees C. for 1 to 3 hours. Samples are diluted 5-fold in specimen diluent (for example, 145.4 mM sodium chloride, 9.51 mM sodium phosphate, 7.7 mM sodium azide, 0.05% Triton X-405, 6 $\mu$m/liter bovine serum albumin, pH 7.4) to quench the reaction, then diluted further for the ELISA as needed.

For the ELISA, Costar High Binding 96-well assay plates (Corning, Inc., Corning, N.Y.) are coated with SW 192 monoclonal antibody from clone 16A7, or a clone of similar affinity. P26-P1 standards are diluted in specimen diluent to a final concentration of 0 to 2 nM. Diluted samples and standards (100 $\mu$l) are incubated on the SW192 plates at 4 degrees C. for 24 hours. The plates are washed 4 times in TTBS buffer (150 mM sodium chloride, 25 mM Tris, 0.05% Tween 20, pH 7.5), then incubated with 0.1 ml/well of streptavidin—alkaline phosphate (Roche Molecular Biochemicals, Indianapolis, Ind.) diluted 1:3000 in specimen diluent. After incubating for one hour at room temperature, the plate is washed 4 times in TTBS, and incubated with fluorescent substrate solution A (31.2 $\mu$m/liter 2-amino-2-methyl-1-propanol, 30 mg/liter, adjusted to pH 9.5 with HCl). Fluorescent values are read after 30 minutes.

Compounds that are effective inhibitors of beta-secretase activity demonstrate reduced cleavage as compared to a control.

Example 36

Assays using Synthetic Oligopeptide-Substrates

Synthetic oligopeptides are prepared which incorporate the known cleavage site of beta-secretase, and optionally detectable tags, such as fluorescent or chromogenic moieties. Examples of such peptides, as well as their production and detection methods are described in allowed U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL DAEF (SEQ ID NO: 3), and the cleavage site is between residues 5 and 6. Another preferred substrate has the sequence ADRGLTTRPGSGLTNIKTEEISEVNLDAEF (SEQ ID NO: 4), and the cleavage site is between residues 26 and 27.

These synthetic APP substrates are incubated in the presence of beta-secretase under conditions sufficient to result in beta-secretase mediated cleavage of the substrate. Comparison of cleavage results in the presence of the compound inhibitor results to a control provides a measure of the compound's inhibitory activity.

Example 73

Inhibition of Beta-secretase Activity—Cellular Assay

An exemplary assay for the analysis of inhibition of beta-secretase activity utilizes the human embryonic kidney cell line HEKp293 (ATCC Accession No. CRL-1573) stably transfected with APP751 containing the naturally occurring double mutation Lys651Met52 to Asn651Leu652 (numbered for APP751), commonly called the Swedish mutation and shown to overproduce A beta (Citron et.al., 1992, Nature 360:672–674). The cells were plated in 96 well plates and in Dulbecco's Modified Eagle's medium (DMEM, Sigma D-6546) containing 10% fetal bovine serum. After cells are established (1 day post plating), cells are incubated in the presence/absence of the inhibitory compound (diluted in DMSO) at the desired concentration, generally from 0.25 to 5.0 Tg/ml, and with a final concentration of DMSO ranging from 0.1 to 0.5%. After incubation at 37degrees C. for two hours, the media is aspirated from the cells and is replaced with fresh compound for an additional 2 hour incubation. At the end of the treatment period, each cell plate is centrifuged at 1100 rpm for 5 minutes at room temperature.

Conditioned media is analyzed for beta-secretase activity by analysis of release of the peptide fragment A beta into the culture medium by immunoassay. Using specific antibodies to detect cleavage product, for example, A beta, the enzymatic activity is measured in the presence and absence of the compound inhibitors to demonstrate specific inhibition of beta-secretase mediated cleavage of APP substrate.

Example 74

Inhibition of Beta-secretase Activity in Primary Neuronal Cells and Human Fetal Brain Tissue Inhibition of beta-secretase activity in primary neuronal cells in mice and fetal brain tissue in humans is assayed as follows.

Media Preparation

Mouse neuronal media without KCl is supplemented with the following: 25 ml fetal bovine serum (FBS, Sigma F-2422 or JRH Biosciences, 12103-78P), heat inactivated for 1 hour at 56° C.; and 25 ml Chang's supplement (Irvine Scientific C104). Final concentrations in 500 ml of mouse neuronal media without KCl is 5% FBS, 5% Chang's supplement.

Human neuronal media without KCl is supplemented with the following: 10 ml of 50× stock B27 solution (Gibco 17504-036). Final concentration in 500 ml human neuronal media without KCl is 1×B27.

Preparation of Cell Culture Plates

Polyethyleneimine (PEI) solution (50% w/v, obtained from Sigma, P-3143) is diluted 1:10 with tissue culture grade water to yield 5% (w/v) diluted solution. The PEI diluted solution is then filter sterilized, using a 0.45 μm filter. Filter sterilized PEI is further diluted 1:100 with sodium borate buffer (150 mM, pH 8.5, sterile) to yield 0.05% (w/v) working solution.

Cell culture plates (24-well flat-bottom, Coming 25820, or 6-well flat-bottom, Coming 25810) are prepared for culture as follows. PEI working solution is added in an amount of 300 μl/well in 24-well plates, or 1.5 ml/well in 6 well plates to coat at approximately 80 μg/cm$^2$. The coated plates are incubated overnight at room temperature. Next, the plates are aspirated and washed twice with 500 I/well (for 24-well plates) or 2.5 ml/well (for 6-well plates) PBS (IX phosphate-buffered saline, pH 7.5, sterile). The plates are then aspirated and incubated with neuronal media without KCl plus 10% PBS (500 μl/well, 24 well; or 2.5 ml/well, 6-well) at 37° C. for at least one hour. After incubation, the plates can be used immediately, or stored under sterile conditions at 37° C. for up to one week (media should be discarded prior to seeding).

Preparation of PDAPP Mouse Cortical Cultures

Wild type, Swiss Webster female mice are mated with homozygotic PDAPP male mice. Sixteen to seventeen days post mating, pregnant females are euthanized by carbon dioxide suffocation. Under sterile conditions, fetuses are removed and decapitated. Fetal brains are removed, and the cerebral cortices are dissected away from the rest of the brain tissue using a dissecting microscope. Cortical tissues are transferred to a 35 mm tissue culture dish (Corning 25000) containing ice cold Hanks buffered salt solution (HBSS, Sigma H9269).

Cortical tissues from ten mouse brains are pooled by transferring to a 50 ml polypropylene conical tube (Falcon 2070), and washed twice with 25 ml cold HBSS. Tissues are resuspended in 5 ml cold CMF HBSS (Calcium- and magnesium-free HBSS, Sigma H-9394) plus 0.5 ml DNase stock solution (Sigma D-4527, 1 mg/ml in CMF HBSS) to yield approximately 100 μg/ml final concentration of DNase. Tissue is triturated with a 5 ml pipette until the suspension becomes homogeneous (approximately 20–30 times). The cell suspension is centrifuged in a clinical centrifuge for three minutes at approximately 600×g. The cell pellet is resuspended in 2.5 ml trypsin-EDTA (1× trypsin-EDTA, Sigma T-3924), and incubated at 37° C. for five minutes.

Neuronal media plus 10% FBS (Sigma F-2422 or JRH Biosciences 12103-78P) is added in an amount of 10 ml to 1 ml DNase stock solution. The solution is mixed gently and incubated at room temperature for three minutes. The cell suspension is filterd by passage through a sterile nylon screen (100 μm pore size, Falcon 2360). The filtrate is centrifuged in a clinical centrifuge for three minutes at approximately 600×g.

The cell pellet is recovered and resuspended in 5 ml complete mouse media, prepared as described above. Cells are counted with a hemacytometer by mixing 50 μl cell suspension with 450 μl trypan blue solution (0.4%, Sigma T-8154). Cells are diluted to 1.2×10$^6$ cells/ml with mouse media. Cells are then plated 0.5 ml/well in 24-well plates coated with PEI, prepared as described above. Cultures are fed twice per week by complete exchange of media.

Preparation of Human Fetal Cortical Cultures

Human fetal brain tissue is obtained from Advanced Bioscience Resources (Alameda, Calif.). Fetal brain tissue is used promptly upon harvesting, and work is performed in a class II hood. Tissue is processed by identifying the cerebral cortex, and removing all traces of meninges with sterile forceps.

Cortical tissues are pooled by transferring to a 50 ml conical tube. Pooled cortical tissues are then washed twice with 25 ml cold HB SS. Tissues are then rsuspended in 10 ml cold CMF HBSS (Sigma H-9394) plus 1 ml DNase stock solution (Sigma D-4527) to yield approximately 100 μg/ml final concentration of DNase. Tissue is triturated with a 10 ml pipette until the suspension becomes homogeneous (approximately 20–30 times). The cell suspension is centrifuged in a clinical centrifuge for three minutes at approximately 600×g. The cell pellet is resuspended in 10 ml trypsin-EDTA (1× trypsin EDTA, Sigman T-3924), and incubated at 37° C. for five minutes. Neuronal media plus 10% FBS is added in an amount of 10 ml to 1 ml DNase stock solution. The solution is mixed gently and incubated at room temperature for three minutes.

The cell suspension is then filtered by passage through a sterile, nylon screen (as described above). The filtrate is then centrifuged as above. The cell pellet is resuspended in 5 ml human media (prepared as described above). Cells are counted with a hemacytometer by mixing 50 μl cell suspension with 450 μl trypan blue solution. Cells are diluted to 1.2×10$^6$ cells/ml with complete media (prepared as described above). The cell suspension is then plated 2 ml/well in 6-well plates coated with PEI, prepared as described above.

The cells are not disturbed for the first week. After that time, cultures are fed twice per week by complete exchange of media.

Neuronal Culture A Beta Assays

Mature cultures are incubated with 300 μl/well (mouse) or 750 μl/well (human) fresh media for 24 hours to generate baseline A beta values. Conditioned media are collected and stored at −20° C. until assayed.

Cultures are then treated with 300 μl/well (mouse) or 750 μl/well (human) fresh media containing compound at the desired range of concentrations for 24 hours. Conditioned media are collected and stored at −20° C. until assayed.

For total A beta measurements and A $beta_{1-42}$ measurements, 100 μl/well is analyzed by ELISA. Inhibition of production for both total A beta and A $beta_{1-42}$ are determined by the difference between the A beta values for the compound treatment and baseline periods. Dose response curves are plotted as percent inhibition versus compound concentration.

At the end of this treatment period, cell viability is tested by MTT cytotoxicity assay. After conditioned media is removed from cell plates for A beta measurement by ELIA, 25 μl of MTT stock (Sigma M-5655 at 5 mg/ml in 1×PBS, aliquoted and stored at −20° C.) are added to all wells. Cell plates are incubated at 37° C. in a $CO_2$ incubator for 1 hour. MTT lysis buffer is added in an amount of 125 μl to each well, and plates are placed on a titer plate shaker at low setting overnight. Plates are read in a microplate reader at 562–650 nm. Cell viability is calculated by percent of control cell optical density (OD).

Example 75

Inhibition of Beta-secretase in Animal Models of AD

Various animal models can be used to screen for inhibition of beta-secretase activity. Examples of animal models useful in the invention include, but are not limited to, mouse, guinea pig, and the like. The animals used can be wild type, transgenic, or knockout models. Examples of transgenic non-human mammalian models are described in U.S. Pat. Nos. 5,912,410 and 5,811,633. In addition, mammalian models can express mutations in APP, such as APP695-SW and the like described herein.

Aniamls are administered an amount of the compound inhibitor formulated appropriately in PBS. Control animals are untreated, or treated with an inactive compound. Administration is repeated daily for a period of days. Beginning on day 0, brain tissue or fluid is obtained from selected animals and analyzed for the presence of APP cleavage peptides, including A beta, using the specific antibodies to A beta. At the end of the test period, animals are sacrificed and brain tissue or fluid is analyzed for the presence of A beta and/or beta amyloid plaques. The tissue is also analyzed for necrosis.

Animals administered the compound inhibitors are expected to demonstrate reduced A beta in brain tissues and fluids, and reduced beta amyloid plaques in brain tissue, as compared with non-treated controls.

Example 76

Inhibition of A Beta Production in Human Patients

Patients suffering from Alzheimer's Disease (AD) demonstrate an increased amount of A beta in the brain. AD patients are administered an amount of the compound inhibitor diluted in PBS. Administration is repeated daily for the duration of the test period. Beginning on day 0, cognative and memory tests are performed once per week.

Patients administered the compound inhibitors are expected to demonstrate cognative and memory scores are expected to slow and/or stabilize as compared with non-treated patients.

Example 77

Prevention of A Beta Production in patients at Risk for AD

Patients predisposed or at risk for developing AD are identified either by recognition of a familial inheritance pattern, for example, presence of the Swedish Muation, and/or by monitoring diagnostic parameters. Patieints identified as predisposed or at risk for developing AD patients are administered an amount of the compound inhibitor diluted in PBS. Administration is repeated daily for the duration of the test period. Beginning on day 0, cognative and memory tests are performed once per month.

Patients administered the compound inhibitors are expected to demonstrate cognative and memory scores are expected to remain stable as compared with non-treated patients.

While this invention has been described with respect to various specific examples and embodiments, it is to be understood that the invention is not limited thereby and should only be construed by interpretation of the scope of the appended claims.

We claim:

1. A compound of the formula

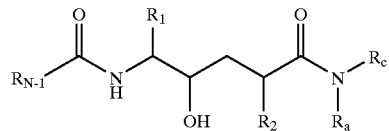

or a pharmaceutically acceptable salt thereof wherein
$R_1$ is:
 (I) $C_1$–$C_6$ alkyl, unsubstituted or unsubstituted with one, two or three $C_1$–$C_3$ alkyl, —F, —Cl, —Br, —I, —OH, —$NH_2$, —C≡N, —$CF_3$, or —$N_3$,
 (II) —$(CH_2)_{1-2}$—S—$CH_3$,
 (III) —$CH_2$—$CH_2$—S—$CH_3$,
 (IV) —$CH_2$—($C_2$–$C_6$ alkenyl) unsubstituted or substituted by one —F,
 (V) —$(CH_2)_{0-3}$—($R_{1-aryl}$) where $R_{1-aryl}$ is phenyl, 1-naphthyl, 2-naphthyl, indanyl, indenyl, dihydronaphthyl, tetralinyl unsubstituted or independently substituted on the aryl ring with one or two of $C_1$–$C_3$ alkyl, —$CF_3$, —F, Cl, —Br, —I, $C_1$–$C_3$ alkoxy, —O—$CF_3$, —$NH_2$, —OH, or —C≡N;
$R_2$ is:
 (I) —H,
 (II) $C_1$–$C_6$ alkyl, or
 (III) —$(CH_2)_{0-4}$—$R_{2-1}$ where $R_{2-1}$ is ($C_3$–$C_6$) cycloalkyl, $R_{1-aryl}$ where $R_{1-aryl}$ is optionally substituted with $R_{100}$, where $R_{100}$ is
  (1) $C_1$–$C_6$ alkyl,
  (2) —F, —Cl, —Br, or —I,
  (3) —OH,
  (4) —$NO_2$,
  (5) —CO—OH,
  (6) —C≡N,
  (7) —CO—$NR_{N-2}R_{N-3}$ where $R_{N-2}$ and $R_{N-3}$ are the same or different and are:
   (a) —H, (b) —$C_1$–$C_6$ alkyl unsubstituted or substituted with one —OH or —$NH_2$, (c) —$C_1$–$C_6$ alkyl unsubstituted or substituted with one to three —F, —Cl, —Br, or —I, (d) —$C_3$–$C_7$ cycloalkyl, (e) —($C_1$–$C_2$ alkyl)-($C_3$–$C_7$cycloalkyl), (f) —($C_1$–$C_6$ alkyl)-O—($C_1$–$C_3$alkyl), (g) —$C_1$–$C_6$ alkenyl with one or two double bonds, (h) —$C_1$–$C_6$ alkynyl with one or two triple bonds, (i) —$C_1$–$C_6$ alkyl chain with one double bond and one triple bond, (8) —CO—($C_3$–$C_{12}$ alkyl), (9) —CO—($C_3$–$C_6$ cycloalkyl),

(11) —CO—$R_{1\text{-}heterocycle}$ where $R_{1\text{-}heterocycle}$ is morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, or tetrahydrothiophenyl, where the $R_{1\text{-}heterocycle}$ group is bonded by any atom of the parent $R_{1\text{-}heterocycle}$ group substituted by hydrogen such that the new bond to the $R_{1\text{-}heterocycle}$ group replace the hydrogen atom and its bond, where heterecycle is unsubstituted or substituted with one or two =O, $C_1$–$C_3$ alkyl, —$CF_3$, —F, Cl, —Br, —I, $C_1$—$C_3$ alkoxy, —$OCF_3$, —$NH_2$, —OH, or —C≡N,

(12) —C-O—$R_{N\text{-}4}$ where $R_{N\text{-}4}$ is morpholinyl, thiomorpholinyl, piperazinyl, piperidinyl, or pyrrolidinyl, where each group is unsubstituted or substituted with one or two $C_1$–$C_3$ alkyl,

(13) —CO—O—$R_{N\text{-}5}$ where $R_{N\text{-}5}$ is:

(a) $C_1$–$C_6$ alkyl, or (b) —$(CH_2)_{0\text{-}2}$—($R_{1\text{-}aryl}$) where $R_{1\text{-}aryl}$ is as defined above,

(14) —$SO_2$—$NR_{N\text{-}2}R_{N\text{-}3}$ where $R_{N\text{-}2}$ and $R_{N\text{-}3}$ are as defined above,

(15) —SO—($C_1$–$C_6$ alkyl),

(16) —$SO_2$—($C_3$–$C_{12}$ alkyl),

(17) —NH—CO—O—$R_{N\text{-}5}$ where $R_{N\text{-}5}$ is as defined above,

(18) —NH—CO—N($C_2$–$C_6$ alkyl)$_2$,

(19) —N—CS—N($C_1$–$C_3$ alkyl)$_2$,

(20) —N($C_1$–$C_3$ alkyl)—CO—$R_{N\text{-}5}$ where $R_{N\text{-}5}$ is as defined above,

(21) —$NR_{N\text{-}2}R_{N\text{-}3}$ where $R_{N\text{-}2}$ and $R_{N\text{-}3}$ can be the same or different and are as defined above,

(22) —$R_{N\text{-}4}$ where $R_{N\text{-}4}$ is as defined above,

(23) —O—CO—($C_1$–$C_6$ alkyl),

(24) —O—CO—N($C_1$–$C_3$ alkyl)$_2$,

(25) —O—CS—N($C_1$–$C_3$ alkyl)$_2$,

(26) —O—($C_1$–$C_6$ alkyl),

(27) —O—($C_2$–$C_5$ alkyl)—COOH,

(28) —S—($C_1$–$C_6$ alkyl),

(29) $C_1$–$C_6$ alkyl unsubustituted or substituted with 1, 2, 3, 4, or 5 —F,

(30) —O—($C_1$–$C_6$ alkyl unsubstituted or substituted with 1, 2, 3, 4, or 5 —F, or

(31) —O-φ, $R_{N\text{-}1}$ is phenyl that is independently substituted with one, two, three or four of $R_{100}$;

$R_a$ is hydrogen or $C_1$–$C_6$ alkyl;

$R_C$ is $R_{CH}$ where $R_{CH}$ is morpholinyl, thiomorpholinyl, thiomorpholinyl S-oxide, thiomorpholinyl S,S-dioxide, piperazinyl, homopiperazinyl, pyrrolidinyl; pyrrolinyl, tetrahydropyranyl, piperidinyl, tetrahydrofuranyl, or tetrahydrothiophenyl, each of which is optionally substituted with oxo, $C_1$–$C_3$ alkyl, —$CF_3$, —F, Cl, —Br or —I, $C_1$–$C_3$ alkoxy, —O—$CF_3$, —$NH_2$, —OH, or —C≡N;

$R_{CY}$ where $R_{CY}$ is pyridinyl, pyrimidinyl, quinolinyl, indenyl, indanyl, benzothiophenyl, indolyl, indolinyl, pyridazinyl, pyrazinyl, isoindolyl, isoquinolyl, quinazolinyl, quinoxalinyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, 1,4-benzodioxanyl, purinyl, oxazolopyridinyl, imidazopyridinyl, isothiazolyl, naphthyridinyl, cinnolinyl, carbazolyl, β-carbolinyl, isochromanyl, chromanyl, furazanyl, tetrahydroisoquinoline, isoindolinyl, isobenzotetrahydrofuranyl, isobenzotetrahydrothienyl, isobenzothiophenyl, benzoxazolyl, or pyridopyridinyl, each of which is optionally substituted with $C_1$–$C_3$ alkyl, —$CF_3$, —F, Cl, —Br, or I, $C_1$–$C_3$ alkoxy, —O—$CF_3$, —$NH_2$, —OH, or —C≡N;

—($C_1$–$C_{10}$)alkyl-$R_{CH}$; or

—($C_1$–$C_{10}$)alkyl-$R_{CY}$.

2. A compound according to claim 1, which is N-[1-(S)-(3,5-Difluoro-benzyl)-2-(S)-hydroxy-4-(R)-(piperidine-1-carbonyl)-hexyl]-N,N-dipropyl-isophthalamide.

3. A compound according to claim 1, which is N-[1-(S)-(3,5-Difluoro-benzyl)-2-(S)-hydroxy-4-(R)-2-morpholin-4-yl-ethylcarbamoyl)-pentyl]-5-methyl-N,N-dipropyl-isophthalamide.

4. A compound according to claim 1, which is N-[1-(S)-(3,5-Difluoro-benzyl)-2-(S)-hydxoxy-4-(R)-[(tetrahydro-furan-2-ylmethyl)-carbamoyl]-pentyl) -5-methyl-N,N-dipropyl-isophthalamide.

5. A compound according to claim 1, which is N-[1-(S)-(3,5-Difluoro-benzyl)-2-(S)-hydroxy-4-(R)-methyl-5-morpholin-4-yl-5-oxo-pentyl]-5-methyl-N,N-dipropyl-isophthalamide.

6. A compound according to claim 1, which is N-[1-(S)-(3,5-Difluoro-benzyl)-4-(R)-[(furan-2-ylmethyl)-carbamoyl]-2-(S)-hydroxy-pentyl)-5-methyl-N,N-dipropyl-isophthalamide.

7. A pharmaceutical composition comprising a compound according to claim 1 in combination with a pharmaceutically acceptable carrier.

8. A method of treating Alzheimer's Disease comprising administering to a subject in need of such treatment an effective amount of a compound according to claim 1.

* * * * *